US012709589B2

(12) United States Patent
Wendlinger

(10) Patent No.: US 12,709,589 B2
(45) Date of Patent: Aug. 18, 2026

(54) METHOD FOR PRODUCING AN IODOFLUOROALKANE COMPOUND

(71) Applicant: ARKEMA FRANCE, Colombes (FR)

(72) Inventor: Laurent Wendlinger, Pierre-Benite Cedex (FR)

(73) Assignee: ARKEMA FRANCE, Colombes (FR)

( * ) Notice: Subject to any disclaimer, the term of this patent is extended or adjusted under 35 U.S.C. 154(b) by 522 days.

(21) Appl. No.: 17/904,379

(22) PCT Filed: Feb. 17, 2021

(86) PCT No.: PCT/FR2021/050283
§ 371 (c)(1),
(2) Date: Aug. 17, 2022

(87) PCT Pub. No.: WO2021/165617
PCT Pub. Date: Aug. 26, 2021

(65) Prior Publication Data

US 2023/0075839 A1 Mar. 9, 2023

(30) Foreign Application Priority Data

Feb. 19, 2020 (FR) ....................................... 2001617
Feb. 19, 2020 (FR) ....................................... 2001618
Feb. 19, 2020 (FR) ....................................... 2001619
Feb. 19, 2020 (FR) ....................................... 2001620
Feb. 19, 2020 (FR) ....................................... 2001622

(51) Int. Cl.
*C07C 17/087* (2006.01)

(52) U.S. Cl.
CPC .................................. *C07C 17/087* (2013.01)

(58) Field of Classification Search
CPC ............................ C07C 17/087; C07C 17/206
See application file for complete search history.

(56) References Cited

U.S. PATENT DOCUMENTS

| | | | |
|---|---|---|---|
| 5,527,975 | A | 6/1996 | Cosserat et al. |
| 2005/0090699 | A1 | 4/2005 | Katsube et al. |
| 2008/0108854 | A1 | 5/2008 | Yang et al. |
| 2017/0204022 | A1 | 7/2017 | Bian et al. |

FOREIGN PATENT DOCUMENTS

| | | | |
|---|---|---|---|
| EP | 1457477 | A1 | 9/2004 |
| FR | 2745286 | A1 | 8/1997 |
| FR | 2794456 | A1 | 12/2000 |
| KR | 20080034414 | A | 4/2008 |
| WO | 03051800 | A1 | 6/2003 |
| WO | 2006112881 | A1 | 10/2006 |

OTHER PUBLICATIONS

ISA/EP; International Search Report and Written Opinion for International Patent Application No. PCT/FR2021/050283 dated Jun. 4, 2021, 13 pages.
Haszeldine, R.N., et al., "Addition of Free Radicals To Unsaturated Systems. Part XII. Free-Radical and Electrophilic Attack On Fluoro-Olefins", Journal of the Chemical Society, Jan. 1, 1956, 11 pages.
Rondestvedt, Christian S., "Methyl-Terminated Perfluoroalkyl Iodides and Related Compounds", J. Org. Chem., vol. 42, No. 11, Jan. 1, 1977, 6 pages.

*Primary Examiner* — Medhanit W Bahta
(74) *Attorney, Agent, or Firm* — Rimon P.C.; Allyn B. Elliott

(57) ABSTRACT

The present invention relates to a process for producing an iodofluoroalkane compound, comprising the steps of: a) placing a fluoroolefin in contact with hydrogen iodide to form a stream A comprising said iodofluoroalkane compound and unreacted hydrogen iodide, b) separating said stream A into a first stream B1 comprising said iodofluoroalkane compound and a stream B2 comprising unreacted hydrogen iodide, c) recycling stream B2 into step a).

20 Claims, No Drawings

METHOD FOR PRODUCING AN IODOFLUOROALKANE COMPOUND

CROSS-REFERENCE TO RELATED APPLICATIONS

This application is a U.S. National Stage application of International Patent Application No. PCT/FR2021/050283, filed on Feb. 17, 2021, which claims the benefit of French Patent Application No. 2001617, filed on Feb. 19, 2020, and the benefit of French Patent Application No. 2001618, filed on Feb. 19, 2020, and the benefit of French Patent Application No. 2001619, filed on Feb. 19, 2020, and the benefit of French Patent Application No. 2001620, filed on Feb. 19, 2020, and the benefit of French Patent Application No. 2001622, filed on Feb. 19, 2020.

TECHNICAL FIELD

The present invention relates to a process for producing haloalkane compounds. In particular, the present invention relates to a process for producing an iodofluoroalkane compound.

TECHNOLOGICAL BACKGROUND OF THE INVENTION

Given the reactivity of the iodine atom, iodofluoro compounds are important synthetic intermediates for the manufacture of pharmaceutical products, plant protection products, fire-extinguishing agents and products for the treatment of various substrates, notably substrates intended for electronic applications.

Iodofluoro compounds also have applications in the field of refrigeration or in air conditioning devices. Compositions comprising $CF_3I$ and HFC-152A intended for use in refrigerant compositions, refrigeration systems, compositions based on swelling agents, aerosol propellants and the like are known from WO 2006/112 881.

Also, patent application FR 2794456 discloses a process for preparing trifluoromethyl iodide or pentafluoroethyl iodide. Also, FR2745286 discloses a process for preparing trifluoromethyl iodide.

Processes for producing iodofluoro compounds can be improved both in terms of conversion and selectivity of the reactions, but also in terms of environmental impact by using more suitable reagents or operating conditions.

The purpose of the present invention is to solve all or some of the drawbacks observed in the processes of the prior art.

INVENTION I

Summary of Invention I

The present invention relates to a process for producing an iodofluoroalkane compound, comprising the steps of:

a) placing a fluoroolefin in contact with hydrogen iodide to form a stream A comprising said iodofluoroalkane compound and unreacted hydrogen iodide, b) separating said stream A into a first stream B1 comprising said iodofluoroalkane compound and a stream B2 comprising unreacted hydrogen iodide, c) recycling stream B2 into step a).

According to a preferred embodiment, the hydrogen iodide is anhydrous.

According to a preferred embodiment, said fluoroolefin is anhydrous.

The fact that the present process is performed under anhydrous conditions makes it possible to obtain better conversion and/or selectivity of the reaction. The anhydrous operating conditions also allow make it possible to limit the corrosion of the facilities.

According to a preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

According to another preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

According to another preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said iodofluoroalkane compound is of formula (II) $(R^1)(R^2)CH$—$C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom; or said iodofluoroalkane compound is of formula (II) $(R^1)(R^2)CH$—$C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above; or said iodofluoroalkane compound is of formula (II) $(R^1)(R^2)CH$—$C(I)(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said fluoroolefin is chosen from the group consisting of $CHF{=}CH_2$, $CF_2{=}CH_2$, $CHF{=}CHF$, $CF_2{=}CHF$, $CF_2{=}CF_2$, $CH_3{-}CF{=}CH_2$, $CH_3{-}CH{=}CHF$, $CH_2F{-}CH{=}CH_2$, $CH_3{-}CF{=}CHF$, $CH_2F{-}CF{=}CH_2$, $CH_3{-}CH{=}CF_2$, $CH_2F{-}CH{=}CHF$, $CHF_2{-}CH{=}CH_2$, $CH_3{-}CF{=}CF_2$, $CH_2F{-}CF{=}CHF$, $CHF_2{-}CF{=}CH_2$, $CH_2F{-}CH{=}CF_2$, $CHF_3{-}CH{=}CHF$, $CF_3{-}CH{=}CH_2$, $CH_2F{-}CF{=}CF_2$, $CHF_2{-}CF{=}CHF$, $CF_3{-}CF{=}CH_2$, $CHF_2{-}CH{=}CF_2$, $CF_3{-}CH{=}CHF$, $CHF_2{-}CF{=}CF_2$, $CF_3{-}CF{=}CHF$, $CF_3{-}CH{=}CF_2$, $CF_3{-}CF{=}CF_2$; preferably from the group consisting of $CF_2{=}CH_2$, $CF_2{=}CHF$, $CF_2{=}CF_2$, $CF_3{-}CH{=}CH_2$, $CF_3{-}CF{=}CH_2$, $CF_3{-}CH{=}CHF$, $CF_3{-}CF{=}CHF$, $CF_3{-}CF{=}CF_2$.

According to a preferred embodiment, said iodofluoroalkane compound is chosen from the group consisting of $CH_2F{-}CH_2I$, $CHFI{-}CH_3$, $CHF_2{-}CH_2I$, $CF_2I{-}CH_3$, $CH_2F{-}CHFI$, $CHF_2{-}CHFI$, $CF_2I{-}CH_2F$, $CHF_2{-}CF_2I$, $CH_3{-}CHF{-}CH_2I$, $CH_3{-}CFI{-}CH_3$, $CH_3{-}CH_2{-}CHFI$, $CH_3{-}CHI{-}CH_2F$, $CH_2F{-}CH_2{-}CH_2I$, $CH_3{-}CHF{-}CHFI$, $CH_3{-}CFI{-}CH_2F$, $CH_2F{-}CHF{-}CH_2I$, $CH_3{-}CH_2{-}CF_2I$, $CH_3{-}CHI{-}CHF_2$, $CH_2F{-}CH_2{-}CHFI$, $CH_2F{-}CHI{-}CH_2F$, $CHF_2{-}CH_2{-}CH_2I$, $CH_3{-}CHF{-}CF_2I$, $CH_3{-}CFI{-}CHF_2$, $CH_2F{-}CHF{-}CHFI$, $CH_2F{-}CFI{-}CH_2F$, $CHF_2{-}CHF{-}CH_2I$, $CH_2F{-}CH_2{-}CF_2I$, $CH_2F{-}CHI{-}CHF_2$, $CHF_2{-}CH_2{-}CHFI$, $CF_3{-}CH_2{-}CH_2I$, $CF_3{-}CHI{-}CH_3$, $CH_2F{-}CHF{-}CF_2I$, $CH_2F{-}CFI{-}CHF_2$, $CHF_2{-}CHF{-}CHFI$, $CF_3{-}CHF{-}CH_2I$, $CF_3{-}CFI{-}CH_3$, $CHF_2{-}CH_2{-}CF_2I$, $CHF_2{-}CHI{-}CHF_2$, $CF_3{-}CH_2{-}CHFI$, $CF_3{-}CHI{-}CH_2F$, $CHF_2{-}CHF{-}CF_2I$, $CHF_2{-}CFI{-}CHF_2$, $CF_3{-}CHF{-}CHFI$, $CF_3{-}CFI{-}CH_2F$, $CF_3{-}CH_2{-}CF_2I$, $CF_3{-}CHI{-}CHF_2$, $CF_3{-}CHF{-}CF_2I$, $CF_3{-}CFI{-}CHF_2$; preferably from the group consisting of $CHF_2{-}CH_2I$, $CF_2I{-}CH_3$, $CHF_2{-}CHFI$, $CF_2I{-}CH_2F$, $CHF_2{-}CF_2I$, $CF_3{-}CH_2{-}CH_2I$, $CF_3{-}CHI{-}CH_3$, $CF_3{-}CHF{-}CH_2I$, $CF_3{-}CFI{-}CH_3$, $CF_3{-}CH_2{-}CHFI$, $CF_3{-}CHI{-}CH_2F$, $CF_3{-}CHF{-}CHFI$, $CF_3{-}CFI{-}CH_2F$, $CF_3{-}CHF{-}CF_2I$, $CF_3{-}CFI{-}CHF_2$.

According to a preferred embodiment, step a) consists in:

converting $CF_2{=}CH_2$ into $CF_2I{-}CH_3$; or
converting $CF_2{=}CHF$ into $CF_2I{-}CH_2F$; or
converting $CF_2{=}CF_2$ into $CHF_2{-}CF_2I$; or
converting $CF_3{-}CH{=}CH_2$ into $CF_3{-}CH_2{-}CH_2I$; or
converting $CF_3{-}CF{=}CH_2$ into $CF_3{-}CFI{-}CH_3$; or
converting $CF_3{-}CH{=}CHF$ into $CF_3{-}CH_2{-}CHFI$; or
converting $CF_3{-}CF{=}CHF$ into $CF_3{-}CHF{-}CHFI$; or
converting $CF_3{-}CF{=}CF_2$ into $CF_3{-}CHF{-}CF_2I$.

According to a preferred embodiment, said fluoroolefin has a boiling point below 100° C. at atmospheric pressure.

According to a preferred embodiment, step a) is performed in the gas phase and in the presence of a catalyst chosen from the group consisting of an oxide, oxyhalide or halide of a metal from columns 4 to 12 of the Periodic Table or of a metal chosen from U, Na, K, Cs, Mg, Ca, Al and Sb.

According to a preferred embodiment, step a) is performed at a temperature from 150° C. to 700° C.

According to a preferred embodiment, step a) is performed in the liquid phase, in the presence of a solvent S1 and a catalyst chosen from alkali metal or alkaline-earth metal salts.

According to a preferred embodiment, step a) is performed in the presence of a solvent S1 with a boiling point of from 20° C. to 250° C.

Detailed Description of Invention I

The present invention relates to a process for producing an iodofluoroalkane compound. In particular, said process comprises placing a fluoroolefin in contact with hydrogen iodide to form a stream A comprising said iodofluoroalkane compound and unreacted hydrogen iodide.

Preferably, said process also comprises steps of separating the compounds contained in stream A. Said process may also comprise a step of recycling the starting reagents.

Thus, said process comprises the steps of:

a) placing a fluoroolefin in contact with hydrogen iodide to form a stream A comprising said iodofluoroalkane compound and unreacted hydrogen iodide,
b) separating said stream A into a first stream B1 comprising said iodofluoroalkane compound and a stream B2 comprising unreacted hydrogen iodide,
c) recycling the stream B2 into step a).

Step a) of the Process

Step a) of the present process requires a fluoroolefin to be placed in contact with hydrogen iodide (HI).

Said fluoroolefin is preferably of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

The term "alkyl" denotes a monovalent radical resulting from a linear or branched alkane comprising the specified number of carbon atoms. The term "cycloalkyl" denotes a monovalent radical resulting from a cycloalkane comprising the specified number of carbon atoms. The term "alkenyl" denotes a monovalent radical comprising the specified number of carbon atoms and at least one carbon-carbon double bond. The term "cycloalkenyl" refers to a monovalent radical resulting from a cycloalkene comprising the specified number of carbon atoms and at least one carbon-carbon double bond in its cyclic part. The term "aryl" denotes a monovalent radical resulting from an arene comprising the specified number of carbon atoms.

Preferably, said alkyl, cycloalkyl, alkenyl, cycloalkenyl or aryl radical is not substituted with functional groups other than fluorine. Said radical may nevertheless comprise several fluorine atoms on its carbon chain, for example, said radical may contain from 1 to 10 fluorine atoms, preferably from 1 to 5 fluorine atoms.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Alternatively, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F and n is an integer from 1 to 5; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F, and n is an integer from 1 to 10; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F, and n is an integer from 1 to 5; provided that at least one of the substituents $R^1$, $R^2$, $R^3$, $R^4$, $Y^1$, $Y^2$ or $Y^3$ is F.

In particular, said fluoroolefin is chosen from the group consisting of $CHF{=}CH_2$, $CF_2{=}CH_2$, $CHF{=}CHF$, $CF_2{=}CHF$, $CF_2{=}CF_2$, $CH_3{-}CF{=}CH_2$, $CH_3{-}CH{=}CHF$, $CH_2F{-}CH{=}CH_2$, $CH_3{-}CF{=}CHF$, $CH_2F{-}CF{=}CH_2$, $CH_3{-}CH{=}CF_2$, $CH_2F{-}CH{=}CHF$, $CHF_2{-}CH{=}CH_2$, $CH_3{-}CF{=}CF_2$, $CH_2F{-}CF{=}CHF$, $CHF_2{-}CF{=}CH_2$, $CH_2F{-}CH{=}CF_2$, $CHF_2{-}CH{=}CHF$, $CF_3{-}CH{=}CH_2$, $CH_2F{-}CF{=}CF_2$, $CHF_2{-}CF{=}CHF$, $CF_3{-}CF{=}CH_2$, $CHF_2{-}CH{=}CF_2$, $CF_3{-}CH{=}CHF$, $CHF_2{-}CF{=}CF_2$, $CF_3{-}CF{=}CHF$, $CF_3{-}CH{=}CF_2$, $CF_3{-}CF{=}CF_2$.

More particularly, said fluoroolefin is chosen from the group consisting of $CF_2{=}CH_2$, $CF_2{=}CHF$, $CF_2{=}CF_2$, $CF_3{-}CH{=}CH_2$, $CF_3{-}CF{=}CH_2$, $CF_3{-}CH{=}CHF$, $CF_3{-}CF{=}CHF$, $CF_3{-}CF{=}CF_2$.

Preferably, step a) is performed in the presence of an anhydrous fluoroolefin. The term “anhydrous” refers here to a fluoroolefin containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said fluoroolefin is free of water. The use of an anhydrous fluoroolefin in the present process makes it possible to avoid the formation of impurities (reaction by-products, polymers derived from the fluoroolefin, etc.).

Said fluoroolefin may have a boiling point of less than 100° C. at atmospheric pressure. Advantageously, said fluoroolefin has a boiling point of less than 75° C. at atmospheric pressure. Preferably, said fluoroolefin has a boiling point of less than 50° C. at atmospheric pressure. More preferentially, said fluoroolefin has a boiling point of less than 25° C. at atmospheric pressure. In particular, said fluoroolefin has a boiling point of less than 10° C. at atmospheric pressure.

In step a), said fluoroolefin is placed in contact with hydrogen iodide (HI). Preferably, the hydrogen iodide is also anhydrous. The term “anhydrous” refers here to hydrogen iodide containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, the hydrogen iodide is free of water. The use of anhydrous hydrogen iodide in the present process also prevents the formation of impurities as mentioned above. The use of an anhydrous fluoroolefin and of anhydrous hydrogen iodide makes it possible to achieve particularly advantageous selectivities at the industrial level.

Preferably, the hydrogen iodide is placed in contact with the fluoroolefin at stoichiometry or in excess thereof. For example, the HI/fluoroolefin mole ratio is from 1 to 50, preferably from 2 to 25, in particular from 5 to 20.

Preferably, the hydrogen iodide is prepared by placing hydrogen ($H_2$) in contact with iodine ($I_2$). In particular, the hydrogen iodide is prepared by placing anhydrous hydrogen in contact with anhydrous iodine. The term “anhydrous” refers to the same definition as mentioned above in relation to hydrogen iodide.

Alternatively, the hydrogen iodide may be in deficit relative to said fluoroolefin. In this case, said streams A and B2 comprise said unreacted fluoroolefin instead of unreacted hydrogen iodide.

Thus, the compound recycled into step a) is the fluoroolefin.

As mentioned above, step a) results in the formation of a stream A comprising said iodofluoroalkane compound and unreacted hydrogen iodide.

Said iodofluoroalkane compound formed is preferably of formula (II) $(R^1)(R^2)CH{-}C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

According to a preferred embodiment, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

According to another preferred embodiment, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Preferably, said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

Said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F or $Y^1—[—C(Y^2)(Y^3)—]_n—$ in which $Y^1$, $Y^2$ and $Y^3$ are, independently of each other and independently for each n unit, chosen from the group consisting of H and F; and n is an integer from 1 to 10; provided that at least one of the substituents $R^1$, $R^2$, $R^3$, $R^4$, $Y^1$, $Y^2$ or $Y^3$ s F.

Said iodofluoroalkane compound is of formula (II) $(R^1)(R^2)CH—C(I)(R^3)(R^4)$ in which $R^1$, $R^2$, $R^3$ and $R^4$ are, independently of each other, chosen from the group consisting of H, F or $Y^1—[—C(Y^2)(Y^3)—]_n—$ in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

In particular, said iodofluoroalkane compound is chosen from the group consisting of $CH_2F—CH_2I$, $CHFI—CH_3$, $CHF_2—CH_2I$, $CF_2I—CH_3$, $CH_2F—CHFI$, $CHF_2—CHFI$, $CF_2I—CH_2F$, $CHF_2—CF_2I$, $CH_3—CHF—CH_2I$, $CH_3—CFI—CH_3$, $CH_3—CH_2—CHFI$, $CH_3—CHI—CH_2F$, $CH_2F—CH_2—CH_2I$, $CH_3—CHF—CHFI$, $CH_3—CFI—CH_2F$, $CH_2F—CHF—CH_2I$, $CH_3—CH_2—CF_2I$, $CH_3—CHI—CHF_2$, $CH_2F—CH_2—CHFI$, $CH_2F—CHI—CH_2F$, $CHF_2—CH_2—CH_2I$, $CH_3—CHF—CF_2I$, $CH_3—CFI—CHF_2$, $CH_2F—CHF—CHFI$, $CH_2F—CFI—CH_2F$, $CHF_2—CHF—CH_2I$, $CH_2F—CH_2—CF_2I$, $CH_2F—CHI—CHF_2$, $CHF_2—CH_2—CHFI$, $CF_3—CH_2—CH_2I$, $CF_3—CHI—CH_3$, $CH_2F—CHF—CF_2I$, $CH_2F—CFI—CHF_2$, $CHF_2—CHF—CHFI$, $CF_3—CHF—CH_2I$, $CF_3—CFI—CH_3$, $CHF_2—CH_2—CF_2I$, $CHF_2—CHI—CHF_2$, $CF_3—CH_2—CHFI$, $CF_3—CHI—CH_2F$, $CHF_2—CHF—CF_2I$, $CHF_2—CFI—CHF_2$, $CF_3—CHF—CHFI$, $CF_3—CFI—CH_2F$, $CF_3—CH_2—CF_2I$, $CF_3—CHI—CHF_2$, $CF_3—CHF—CF_2I$, $CF_3—CFI—CHF_2$.

More particularly, said iodofluoroalkane is chosen from the group consisting of $CHF_2—CH_2I$, $CF_2I—CH_3$, $CHF_2—CHFI$, $CF_2I—CH_2F$, $CHF_2—CF_2I$, $CF_3—CH_2—CH_2I$, $CF_3—CHI—CH_3$, $CF_3—CHF—CH_2I$, $CF_3—CFI—CH_3$, $CF_3—CH_2—CHFI$, $CF_3—CHI—CH_2F$, $CF_3—CHF—CHFI$, $CF_3—CFI—CH_2F$, $CF_3—CHF—CF_2I$, $CF_3—CFI—CHF_2$.

In a particularly preferred manner, step a) of the present production process consists in converting $CF_2=CH_2$ into $CF_2I—CH_3$; or
converting $CF_2=CHF$ into $CF_2I—CH_2F$; or
converting $CF_2=CF_2$ into $CHF_2—CF_2I$; or
converting $CF_3—CH=CH_2$ into $CF_3—CH_2—CH_2I$; or
converting $CF_3—CF=CH_2$ into $CF_3—CFI—CH_3$; or
converting $CF_3—CH=CHF$ into $CF_3—CH_2—CHFI$; or
converting $CF_3—CF=CHF$ into $CF_3—CHF—CHFI$; or
converting $CF_3—CF=CF_2$ into $CF_3—CHF—CF_2I$.

Step a) may be performed in the liquid phase or in the gas phase. Step a) may be performed in the presence or absence of a catalyst.

When step a) is performed in the gas phase, step a) may be performed in the presence of a catalyst. Preferably, the catalyst is chosen from the group consisting of an oxide, oxyhalide or halide of a metal from columns 4 to 12 of the Periodic Table or of a metal chosen from Li, Na, K, Cs, Mg, Ca, Ai and Sb.

Preferably, the catalyst is a chromium oxide, chromium oxyfluoride or a chromium fluoride. The chromium oxyfluoride preferably has a fluorine content of from 10% to 50% by weight, preferably from 20% to 50% by weight, in particular from 30% to 50% by weight. The fluorine content is measured ionometrically or by weight change of the catalyst or by any other quantitative method known to those skilled in the art. The chromium oxyfluoride or chromium fluoride catalyst preferably has a specific surface area of from 15 to 100 $m^2/g$. The chromium oxide catalyst preferably has a specific surface area of from 100 to 300 $m^2/g$. The specific surface area is measured on a Micromeritics Gemini 2360 machine using the standard 5-point method (BET method).

When the catalyst is a chromium oxide, chromium oxyfluoride or chromium fluoride, it may also contain from 0.5% to 10% by weight of a cocatalyst relative to the total weight of the catalyst.

Said cocatalyst is chosen from Cr, Ni, Zn, Ti, V, Zr, Mo, Ge, Sn, Pb and Mg.

When the metal is chosen from U, Na, K, Cs, Mg, Ca, Al and Sb, the anion associated with the metal is $F^-$, $Cl^-$, $I^-$ or $CO_3^{2-}$. Preferably, the catalyst is NaI or KI. The catalyst preferably has a specific surface area of between 20 and 1000 $m^2/g$, in particular between 20 and 300 $m^2/g$.

The catalyst may be deposited onto a porous support. The porous support may be chosen from activated charcoals, graphite, aluminas and alumina fluorides.

When the metal of the catalyst is chosen from U, Na, K, Cs, Mg, Ca, Al and Sb, the catalyst content is from 1% to 30% by weight relative to said fluoroolefin.

When the catalyst is chosen from the group consisting of an oxide, oxyhalide or halide of a metal from columns 4 to 12 of the Periodic Table, it may be activated prior to its use in step a). For example, said catalyst may be activated in the presence of oxygen, air, hydrogen iodide or HF or a mixture thereof.

The catalyst may also deactivate over time. Thus, step a) may be performed in the presence of oxygen or air or an oxygen-nitrogen mixture. If oxygen is used in step a), it is present in an amount of from 0.005 mol % to 10 mol % relative to the molar amount of fluoroolefin.

The catalyst may also be regenerated after the present process has been performed. The regeneration step may comprise placing the catalyst in contact with a stream of oxygen or air at a temperature of from 200° C. to 700° C.

Alternatively, step a) may be performed in the gas phase in the absence of a catalyst.

In the gas phase, step a) is performed at a temperature of from 150° C. to 700° C., preferably from 250° C. to 600° C.

Irrespective of whether step a) is performed in the gas phase in the presence or absence of a catalyst, the pressure in this step is from 0.1 bar to 30 bar, preferably from 1 bar to 20 bar, in particular from 1 bar to 15 bar.

Alternatively, step a) is performed in the liquid phase. Preferably, when step a) is performed in the liquid phase, it is performed in the presence of a solvent S1. Preferably, the solvent S1 is anhydrous. The term "anhydrous" refers here to a solvent S1 containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said solvent S1 is free of water.

The solvent S1 has a boiling point of from 0° C. to 250° C., preferably from 20° C. to 250° C., in particular from 20° C. to 200° C. Said solvent S1 is chosen from the group consisting of acetic acid, $CCl_4$, chloroform, dichloromethane, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof.

The temperature for performed step a) is from 50° C. to 280° C., preferably from 50° C. to 250° C. Preferably, step a), in the liquid phase, is performed in the presence of a catalyst chosen from alkali metal or alkaline-earth metal salts. Preferably, the catalyst is an alkali metal salt. Any alkali metal iodide may be used, but sodium iodide or potassium iodide is preferably used. The ratio between the catalyst and said fluoroolefin is between 1 and 20, preferably between 1 and 10. The catalyst preferably has a specific surface area of between 20 and 1000 $m^2/g$, in particular between 20 and 300 $m^2/g$. The catalyst may be deposited onto a porous support. The porous support may be chosen from activated charcoals, graphite, aluminas and alumina fluorides. When the metal of the catalyst is chosen from U, Na, K, Cs, Mg, Ca, Al and Sb, the catalyst content is from 1% to 30% by weight relative to said fluoroolefin.

As mentioned above, step a) makes it possible to obtain a stream A comprising said iodofluoroalkane compound and unreacted hydrogen iodide. Stream A may also comprise other compounds such as impurities, reaction by-products or even unreacted fluoroolefin.

For example, when the fluoroolefin is $CF_2{=}CH_2$, besides $CF_2I{-}CH_3$, stream A may include $CHF_2{-}CH_2I$. When the fluoroolefin is $CF_2{=}CHF$, besides $CF_2I{-}CH_2F$, stream A may comprise $CF_3{-}CHFI$. When the fluoroolefin is $CF_3{-}CH{=}CH_2$, besides $CF_3{-}CH_2{-}CH_2I$, stream A may comprise $CF_3{-}CHI{-}CH_3$. When the fluoroolefin is $CF_3{-}CF{=}CH_2$, besides $CF_3{-}CFI{-}CH_3$, stream A may comprise $CF_3{-}CHF{-}CH_2I$. When the fluoroolefin is $CF_3{-}CH{=}CHF$, besides $CF_3{-}CH_2{-}CHFI$, stream A may comprise $CF_3{-}CHI{-}CH_2F$. When the fluoroolefin is $CF_3{-}CF{=}CHF$, besides $CF_3{-}CHF{-}CHFI$, stream A may comprise $CF_3{-}CFI{-}CH_2F$. When the fluoroolefin is $CF_3{-}CF{=}CF_2$, besides $CF_3{-}CHF{-}CF_2I$, stream A may comprise $CF_3{-}CFI{-}CHF_2$.

According to another embodiment, the present process may be performed in the presence of a mixture of fluoroolefins as defined above to result in the production of a mixture of iodofluoroalkane compounds in said stream A and in said stream B1.

Step b) of the Process

Said stream A is then separated to form a first stream B1 comprising said iodofluoroalkane compound and a stream B2 comprising unreacted hydrogen iodide. Both said stream B1 and said stream B2 may contain impurities, reaction by-products or even unreacted fluoroolefin. In this case, stream B1 is subjected to a further purification step to give a stream B1 comprising said purified iodofluoroalkane compound. Preferably, after the separation and possible purification step, the content of said iodofluoroalkane compound in said stream B1 is greater than 90%, advantageously greater than 92%, preferably greater than 94%, more preferentially greater than 96%, in particular greater than 98%, more particularly greater than 99%.

Said stream A is preferably separated out and/or purified by distillation, azeotropic distillation, distillation under pressure, extractive distillation, cold separation, absorption in a solvent or a combination thereof.

Said stream A may also be separated out or purified by placing in contact with an adsorbent.

Said adsorbent may be a zeolite or a molecular sieve having a pore aperture with an average diameter of between 3 ångströms and 11 ångströms, advantageously between 4 ångströms and 10 ångströms, preferably between 5 ångströms and 10 ångströms.

Step c) of the process Step c) of the present process includes the recycling of stream B2 into step a). This recycling step improves the overall yield of the process (better conversion) and saves on expensive reagents (and catalysts), while at the same time minimizing the environmental impact. Without this recycling step, the unreacted hydrogen iodide would have to be incinerated, thus increasing the carbon footprint of the process.

If stream B1 comprises unreacted fluoroolefin, this can be removed from stream B1 and also be recycled into step a).

The present process may be performed continuously or in a batchwise or semi-batchwise manner.

Preferably, in order to avoid corrosion problems, the reactor, in which step a) is performed, is made of a material comprising a base layer made of a material M1 and an inner layer made of a material M2.

Advantageously, the material M2 comprises at least 40% by weight of nickel relative to the total weight of the material M2. Preferably, the material M2 comprises at least 45% by weight of nickel, more preferentially at least 50% by weight of nickel, in particular at least 55% by weight of nickel, more particularly at least 60% by weight of nickel, preferably at least 65% by weight of nickel, more preferably at least 70% by weight of nickel relative to the total weight of the material M2.

The material M2 may also comprise chromium in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

The material M2 may also comprise molybdenum in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

Preferably, the material M2 is Monel®, Hastelloy®, Inconel® or Incoloy®.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron relative to the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, preferably less than 0.1% by weight relative to the total weight of the material M1. More particularly, the material M1 may comprise between 0.01% and 0.2% by weight of carbon on the basis of the total weight of the material M1.

Preferably, said base layer and said inner layer are placed against each other by hot or cold plating, hot or cold rolling or welding.

EXAMPLES

Example 1

250 mL of sulfolane and 0.1 mol of sodium iodide were introduced into a 500 mL Hastelloy C276 reactor, equipped with a stirrer, a heating device and a temperature control system. The reaction medium was brought to 90-100° C. with stirring. The anhydrous reagents, 0.5 mol of $CF_2{=}CHF$ and 0.8 mol of HI (prepared from $H_2$ and $I_2$), were introduced into the reaction medium. After 4 hours of reaction with stirring, a sample was taken, washed and dried and then analyzed by gas chromatography (area percentage). The conversion of $CF_2{=}CHF$ was 85% for a selectivity towards $CF_2I{-}CH_2F$ of 89%.

Example 2

A chromium oxyfluoride catalyst containing between 15% and 20% by weight of fluorine was introduced into a tubular reactor made of Inconel 600. The catalyst was preactivated in the presence of an $O_2$ gas stream at a temperature of 300° C. A gaseous stream of hexafluoropropene and a gaseous stream of hydrogen iodide prepared from $H_2$ and $I_2$ (HFP/HI mole ratio=1/2) were passed over this catalyst at a temperature of 270° C. under 3 bar. At the reactor outlet, the gases were washed and then dried and condensed in a cold trap. A sample was taken and analyzed by gas chromatography (area percentage). The conversion of hexafluoropropene was 95% for a selectivity towards $CF_3{-}CHF{-}CF_2I$ of 97%.

Equivalent conversion and selectivity values were obtained with $CF_3{-}CF{=}CHF$, $CF_3{-}CH{=}CHF$, $CF_3{-}CF{=}CH_2$ and $CF_3{-}CH{=}CH_2$ as fluoroolefins.

Invention II

Summary of Invention II

The present invention relates to a process for producing an iodofluoroalkane compound, comprising step a) of placing an olefin in contact with anhydrous iodine monofluoride (IF) to form a stream A comprising said iodofluoroalkane compound and optionally unreacted iodine monofluoride.

The present process makes it possible to obtain the iodofluoroalkane compounds with improved selectivity while at the same time maintaining a high conversion of the starting olefin.

According to a preferred embodiment, said olefin is a fluoroolefin.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

Said iodofluoroalkane compound is obtained by adding an iodine monofluoride (IF) molecule to a carbon-carbon double bond of said olefin.

According to a preferred embodiment, said iodofluoroalkane compound is of formula (II) $(R^1)(R^2)CF{-}C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom; or said iodofluoroalkane compound is of formula (II) $(R^1)(R^2)CF{-}C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above;

or said iodofluoroalkane compound is of formula (II) $(R^1)(R^2)CF{-}C(I)(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said olefin is a fluoroolefin chosen from the group consisting of $CHF{=}CH_2$, $CF_2{=}CH_2$, $CHF{=}CHF$, $CF_2{=}CHF$, $CF_2{=}CF_2$, $CH{-}CF{=}CH_2$, $CH_3{-}CH{=}CHF$, $CH_2F{-}CH{=}CH_2$, $CH_3{-}CF{=}CHF$, $CH_2F{-}CF{=}CH_2$, $CH_3{-}CH{=}CF_2$, $CH_2F{-}CH{=}CHF$, $CHF_2{-}CH{=}CH_2$, $CH_3{-}CF{=}CF_2$, $CH_2F{-}CF{=}CHF$, $CHF_2{-}CF{=}CH_2$, $CH_2F{-}CH{=}CF_2$, $CHF_2{-}CH{=}CHF$, $CF_3{-}CH{=}CH_2$, $CH_2F{-}CF{=}CF_2$, $CHF_2{-}CF{=}CHF$, $CF_3{-}CF{=}CH_2$, $CHF_2{-}CH{=}CF_2$, $CF_3{-}CH{=}CHF$, $CHF_2{-}CF{=}CF_2$, $CF_3{-}CF{=}CHF$, $CF_3{-}CH{=}CF_2$, $CF_3{-}CF{=}CF_2$; preferably from the group consisting of $CF_2{=}CH_2$, $CF_2{=}CHF$, $CF_2{=}CF_2$, $CF_3{-}CH{=}CH_2$, $CF_3{-}CF{=}CH_2$, $CF_3{-}CH{=}CHF$, $CF_3{-}CF{=}CHF$, $CF_3{-}CF{=}CF_2$.

According to a preferred embodiment, said iodofluoroalkane compound is chosen from the group consisting of $CHFI{-}CH_2F$, $CHF_2{-}CH_2I$, $CF_2I{-}CH_2F$, $CF_3{-}CH_2I$, $CHFI{-}CHF_2$, $CF_2I{-}CHF_2$, $CF_3{-}CHFI$, $CF_2I{-}CF_3$, $CH_3{-}CFI{-}CH_2F$, $CH_3{-}CF_2{-}CH_2I$, $CH_3{-}CHI{-}CHF_2$, $CH_3{-}CHF{-}CHFI$, $CH_2F{-}CHI{-}CH_2F$, $CH_2F{-}CHF{-}CH_2I$, $CH_3{-}CFI{-}CHF_2$, $CH_3{-}CF_2{-}CHFI$, $CH_2F{-}CFI{-}CH_2F$, $CH_2F{-}CF_2{-}CH_2I$, $CH_3{-}CHI{-}CF_3$, $CH_3{-}CHF{-}CF_2I$, $CH_2F{-}CHI{-}CHF_2$, $CH_2F{-}CHF{-}CHFI$, $CHF_2{-}CHF{-}CH_2I$, $CH_3{-}CFI{-}CF_3$, $CH_3{-}CF_2{-}CF_2I$, $CH_2F{-}CFI{-}CHF_2$, $CH_2F{-}CF_2{-}CHFI$, $CHF_2{-}CF_2{-}CH_2I$, $CH_2F{-}CHF{-}CF_2I$, $CHF_2{-}CHI{-}CHF_2$, $CHF_2{-}CHF{-}CHFI$, $CF_3{-}CHI{-}CH_2F$, $CF_3{-}CHF{-}CH_2I$, $CH_2F{-}CF_2{-}CF_2I$, $CHF_2{-}CFI{-}CHF_2$, $CHF_2{-}CF_2{-}CHFI$, $CF_3{-}CFI{-}CH_2F$, $CF_3{-}CF_2{-}CH_2I$, $CHF_2{-}CHF{-}CF_2I$, $CF_3{-}CHI{-}CHF_2$, $CF_3{-}CHF{-}CHFI$, $CHF_2{-}CF_2{-}CF_2I$, $CF_3{-}CFI{-}CHF_2$, $CF_3{-}CF_2{-}CHFI$, $CF_3{-}CHI{-}CF_3$, $CF_3{-}CHF{-}CF_2I$, $CF_3{-}CFI{-}CF_3$, $CF_3{-}CF_2{-}CF_2I$; preferably from the group consisting of $CF_2I{-}CH_2F$, $CF_3{-}CH_2I$, $CF_2I{-}CHF_2$, $CF_3{-}CHFI$, $CF_2I{-}CF_3$, $CF_3{-}CHI{-}CH_2F$, $CF_3{-}CHF{-}CH_2I$, $CF_3{-}CFI{-}CH_2F$, $CF_3{-}CF_2{-}CH_2I$, $CF_3{-}CHI{-}CHF_2$, $CF_3{-}CHF{-}CHFI$, $CF_3{-}CFI{-}CHF_2$, $CF_3{-}CF_2{-}CHFI$, $CF_3{-}CFI{-}CF_3$, $CF_3{-}CF_2{-}CF_2I$.

According to a preferred embodiment, step a) consists in:

converting $CF_2{=}CH_2$ into $CF_3{-}CH_2I$;

converting $CF_2{=}CHF$ into $CF_3{-}CHFI$; or converting $CF_2{=}CF_2$ into $CF_3{-}CF_2I$; or converting $CF_3{-}CH{=}CH_2$ into $CF_3{-}CHI{-}CH_2F$; or converting $CF_3{-}CF{=}CH_2$ into $CF_3{-}CF_2{-}CH_2I$; or converting $CF_3{-}CH{=}CHF$ into $CF_3{-}CHI{-}CHF_2$; or converting $CF_3{-}CF{=}CHF$ into $CF_3{-}CFI{-}CHF_2$; or converting $CF_3{-}CF{=}CF_2$ into $CF_3{-}CFI{-}CF_3$.

According to a preferred embodiment, the anhydrous iodine monofluoride is prepared by mixing anhydrous iodine ($I_2$) with anhydrous iodine pentafluoride ($IF_5$).

According to a preferred embodiment, the process comprises a step b) of purifying said stream A to form a stream B1 comprising at least 90% by weight of said iodofluoroalkane compound.

Detailed Description of Invention II

The present invention relates to a process for producing an iodofluoroalkane compound, comprising step a) of placing an olefin in contact with anhydrous iodine monofluoride (IF) to form a stream A comprising said iodofluoroalkane compound and optionally unreacted iodine monofluoride.

Step a) of the Process

The present process makes it possible to obtain the iodofluoroalkane compounds with improved selectivity while at the same time maintaining a high conversion of the starting olefin.

Said olefin may be of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical, a $C_3$-$C_{10}$ cycloalkyl radical, a $C_2$-$C_{10}$ alkenyl radical, a $C_3$-$C_{10}$ cycloalkenyl radical and a $C_6$-$C_{10}$ aryl radical.

Performing step a) with anhydrous iodine monofluoride makes it possible to increase the selectivity and conversion of the reaction. The term "anhydrous" refers here to iodine monofluoride containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said iodine monofluoride is free of water.

According to a preferred embodiment, said olefin is a fluoroolefin. Preferably, said fluoroolefin is anhydrous. The term "anhydrous" refers here to a fluoroolefin containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said fluoroolefin is free of water. The use of an anhydrous fluoroolefin in the present process makes it possible to avoid the formation of impurities (reaction by-products, polymers derived from the fluoroolefin, etc.).

According to a preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

The term "alkyl" denotes a monovalent radical resulting from a linear or branched alkane comprising the number of carbon atoms specified. The term "cycloalkyl" denotes a monovalent radical resulting from a cycloalkane comprising the number of carbon atoms specified. The term "alkenyl" denotes a monovalent radical comprising the number of carbon atoms specified and at least one carbon-carbon double bond. The term "cycloalkenyl" refers to a monovalent radical resulting from a cycloalkene comprising the number of carbon atoms specified and at least one carbon-carbon double bond in its cyclic part. The term "aryl" denotes a monovalent radical resulting from an arene comprising the number of carbon atoms specified.

Preferably, said alkyl, cycloalkyl, alkenyl, cycloalkenyl or aryl radical is not substituted with functional groups other than fluorine. Said radical may nevertheless comprise several fluorine atoms on its carbon chain, for example, said radical may contain from 1 to 10 fluorine atoms, preferably from 1 to 5 fluorine atoms.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$—$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

According to a preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_5$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above including at least one fluorine atom.

Preferably, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above including at least one fluorine atom.

According to another preferred embodiment, said fluoroolefin is of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F and n is an integer from 1 to 5; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F, and n is an integer from 1 to 10; provided that at least one of the substituents $R^1$, $R^2$, $R^3$, $R^4$, $Y^1$, $Y^2$ or $Y^3$ is F.

Said fluoroolefin may be of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F, and n is an integer from 1 to 5; provided that at least one of the substituents $R^1$, $R^2$, $R^3$, $R^4$, $Y^1$, $Y^2$ or $Y^3$ is F.

In particular, said fluoroolefin is chosen from the group consisting of $CHF{=}CH_2$, $CF_2{=}CH_2$, $CHF{=}CHF$, $CF_2{=}CHF$, $CF_2{=}CF_2$, $CH_3$—$CF{=}CH_2$, $CH_3$—$CH{=}CHF$, $CH_2F$—$CH{=}CH_2$, $CH_3$—$CF{=}CHF$, $CH_2F$—$CF{=}CH_2$, $CH_3$—$CH{=}CF_2$, $CH_2F$—$CH{=}CHF$, $CHF_2$—$CH{=}CH_2$, $CH_3$—$CF{=}CF_2$, $CH_2F$—$CF{=}CHF$, $CHF_2$—$CF{=}CH_2$, $CH_2F$—$CH{=}CF_2$, $CHF_2$—$CH{=}CHF$, $CF_3$—$CH{=}CH_2$, $CH_2F$—$CF{=}CF_2$, $CHF_2$—$CF{=}CHF$, $CF_3$—$CF{=}CH_2$, $CHF_2$—$CH{=}CF_2$, $CF_3$—$CH{=}CHF$, $CHF_2$—$CF{=}CF_2$, $CF_3$—$CF{=}CHF$, $CF_3$—$CH{=}CF_2$, $CF_3$—$CF{=}CF_2$.

More particularly, said fluoroolefin is chosen from the group consisting of $CF_2$═$CH_2$, $CF_2$═CHF, $CF_2$═$CF_2$, $CF_3$—CH═$CH_2$, $CF_3$—CF═$CH_2$, $CF_3$—CH═CHF, $CF_3$—CF═CHF, $CF_3$—CF═$CF_2$.

Preferably, the iodine monofluoride is placed in contact with the olefin, preferably with the fluoroolefin, at stoichiometry or in excess thereof. For example, the IF/fluoroolefin mole ratio is from 1 to 50, preferably from 1.5 to 25, in particular from 2 to 20.

Preferably, the anhydrous iodine monofluoride is prepared from anhydrous reagents.

Preferably, the anhydrous iodine monofluoride is prepared in situ by mixing anhydrous iodine ($I_2$) with anhydrous iodine pentafluoride ($IF_5$). In this case, said stream A may also comprise unreacted iodine and/or iodine pentafluoride in addition to said iodofluoroalkane compound and optionally unreacted iodine monofluoride. For both iodine and iodine pentafluoride, the term "anhydrous" refers here to a water content in the compound under consideration of less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water. Preferentially preferably, the iodine and iodine pentafluoride are free of water.

The mixing of the anhydrous iodine with the anhydrous iodine pentafluoride may be performed in the liquid state. Thus, the iodine is dissolved in the iodine pentafluoride. Alternatively, the iodine may be introduced in gaseous form into an iodine pentafluoride solution.

Alternatively, anhydrous iodine monofluoride could be generated by mixing anhydrous iodine with anhydrous $IF_7$ or mixing anhydrous iodine with anhydrous fluorine $F_2$ or mixing anhydrous iodine with anhydrous $IF_3$.

Said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

According to a preferred embodiment, said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, F, I, a $C_1$-$C_{10}$ perfluoroalkyl radical, a $C_5$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above including at least one fluorine atom.

Preferably, said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above including at least one fluorine atom.

According to another preferred embodiment, said iodofluoroalkane compound is of formula (II) ($R^1$)($R^2$)CF—C(I)($R^3$)($R^4$) in which $R^1$, $R^2$, $R^3$ and $R^4$ are, independently of each other, chosen from the group consisting of H, I, F or $Y^1$—[—C($Y^2$)($Y^3$)—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Said iodofluoroalkane compound may be of formula (II) ($R^1$)($R^2$)CF—C(I)($R^3$)($R^4$) in which $R^1$, $R^2$, $R^3$ and $R^4$ are, independently of each other, chosen from the group consisting of H, I, F or $Y^1$—[—C($Y^2$)($Y^3$)—]$_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $R^4$, $Y^1$, $Y^2$ or $Y^3$ is F.

Said iodofluoroalkane compound may be of formula (II) ($R^1$)($R^2$)CF—C(I)($R^3$)($R^4$) in which $R^1$, $R^2$, $R^3$ and $R^4$ are, independently of each other, chosen from the group consisting of H, F or $Y^1$—[—C($Y^2$)($Y^3$)—]$_n$— in which $Y^1$, $Y^2$ and $Y^3$ are, independently of each other and independently for each n unit, chosen from the group consisting of H and F; and n is an integer from 1 to 10; provided that at least one of the substituents $R^1$, $R^2$, $R^3$, $R^4$, $Y^1$, $Y^2$ or $Y^3$ is F.

Said iodofluoroalkane compound may be of formula (II) ($R^1$)($R^2$)CF—C(I)($R^3$)($R^4$) in which $R^1$, $R^2$, $R^3$ and $R^4$ are, independently of each other, chosen from the group consisting of H, F or $Y^1$—[—C($Y^2$)($Y^3$)—]$_n$— in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said iodofluoroalkane compound is chosen from the group consisting of CHFI—$CH_2$F, $CHF_2$—$CH_2$I, $CF_2$I—$CH_2$F, $CF_3$—$CH_2$I, CHFI—$CHF_2$, $CF_2$I—$CHF_2$, $CF_3$—CHFI, $CF_2$I—$CF_3$, $CH_3$—CFI—$CH_2$F, $CH_3$—$CF_2$—$CH_2$I, $CH_3$—CHI—$CHF_2$, $CH_3$—CHF—CHFI, $CH_2$F—CHI—$CH_2$F, $CH_2$F—CHF—$CH_2$I, $CH_3$—CFI—$CHF_2$, $CH_3$—$CF_2$—CHFI, $CH_2$F—CFI—$CH_2$F, $CH_2$F—$CF_2$—$CH_2$I, $CH_3$—CHI—$CF_3$, $CH_3$—CHF—$CF_2$I, $CH_2$F—CHI—$CHF_2$, $CH_2$F—

CHF—CHFI, $CHF_2$—CHF—$CH_2I$, $CH_3$—CFI—$CF_3$, $CH_3$—$CF_2$—$CF_2I$, $CH_2F$—CFI—$CHF_2$, $CH_2F$—$CF_2$—CHFI, $CHF_2$—$CF_2$—$CH_2I$, $CH_2F$—CHF—$CF_2I$, $CHF_2$—CHI—$CHF_2$, $CHF_2$—CHF—CHFI, $CF_3$—CHI—$CH_2F$, $CF_3$—CHF—$CH_2I$, $CH_2F$—$CF_2$—$CF_2I$, $CHF_2$—CFI—$CHF_2$, $CHF_2$—$CF_2$—CHFI, $CF_3$—CFI—$CH_2F$, $CF_3$—$CF_2$—$CH_2I$, $CHF_2$—CHF—$CF_2I$, $CF_3$—CHI—$CHF_2$, $CF_3$—CHF—CHFI, $CHF_2$—$CF_2$—$CF_2I$, $CF_3$—CFI—$CHF_2$, $CF_3$—$CF_2$—CHFI, $CF_3$—CHI—$CF_3$, $CF_3$—CHF—$CF_2I$, $CF_3$—CFI—$CF_3$, $CF_3$—$CF_2$—$CF_2I$.

Preferably, said iodofluoroalkane compound is chosen from the group consisting of $CF_2I$—$CH_2F$, $CF_3$—$CH_2I$, $CF_2I$—$CHF_2$, $CF_3$—CHFI, $CF_2I$—$CF_3$, $CF_3$—CHI—$CH_2F$, $CF_3$—CHF—$CH_2I$, $CF_3$—CFI—$CH_2F$, $CF_3$—$CF_2$—$CH_2I$, $CF_3$—CHI—$CHF_2$, $CF_3$—CHF—CHFI, $CF_3$—CFI—$CHF_2$, $CF_3$—$CF_2$—CHFI, $CF_3$—CFI—$CF_3$, $CF_3$—$CF_2$—$CF_2I$.

According to a preferred embodiment, step a) consists in:

converting $CF_2$=$CH_2$ into $CF_3$—$CH_2I$;
converting $CF_2$=CHF into $CF_3$—CHFI; or
converting $CF_2$=$CF_2$ into $CF_3$—$CF_2I$; or
converting $CF_3$—CH=$CH_2$ into $CF_3$—CHI—$CH_2F$; or
converting $CF_3$—CF=$CH_2$ into $CF_3$—$CF_2$—$CH_2I$; or
converting $CF_3$—CH=CHF into $CF_3$—CHI—$CHF_2$; or
converting $CF_3$—CF=CHF into $CF_3$—CFI—$CHF_2$; or
converting $CF_3$—CF=$CF_2$ into $CF_3$—CFI—$CF_3$.

Step a) may be performed in the liquid phase or in the gas phase. Step a) may be performed in the presence or absence of a catalyst.

Gas Phase Step a)

When step a) is performed in the gas phase, step a) may be performed in the presence of a catalyst. Preferably, the catalyst is chosen from the group consisting of an oxide, oxyhalide or halide of a metal or metalloid from columns 4 to 15 of the Periodic Table or of a metal chosen from U, Na, K, Cs, Mg and Ca.

Preferably, the catalyst is a chromium oxide, chromium oxyfluoride or a chromium fluoride. The chromium oxyfluoride preferably has a fluorine content of from 10% to 50% by weight, preferably from 20% to 50% by weight, in particular from 30% to 50% by weight. The fluorine content is measured ionometrically or by weight change of the catalyst or by any other quantitative method known to those skilled in the art. The chromium oxyfluoride or chromium fluoride catalyst preferably has a specific surface area of from 15 to 100 $m^2/g$. The chromium oxide catalyst preferably has a specific surface area of from 100 to 300 $m^2/g$. The specific surface area is measured on a Micromeritics Gemini 2360 machine using the standard 5-point method (BET method). In addition, the catalyst content is from 0.01% to 10% by weight relative to said fluoroolefin. When the catalyst is a chromium oxide, chromium oxyfluoride or chromium fluoride, it may also contain from 0.5% to 10% by weight of a cocatalyst relative to the total weight of the catalyst. Said cocatalyst is chosen from Cr, Ni, Zn, Ti, V, Zr, Mo, Ge, Sn, Pb and Mg. When the metal is chosen from Li, Na, K, Cs, Mg and Ca, the anion associated with the metal is $F^-$, $Cl^-$, $I^-$ or $CO_3^{2-}$. Preferably, the catalyst is NaI or KI. The catalyst preferably has a specific surface area of between 20 and 1000 $m^2/g$, in particular between 20 and 300 $m^2/g$.

The catalyst may be deposited onto a porous support. The porous support may be chosen from activated charcoals, graphite, aluminas and alumina fluorides.

When the metal of the catalyst is chosen from U, Na, K, Cs, Mg and Ca, the catalyst content is from 1% to 30% by weight relative to said fluoroolefin.

When the catalyst is chosen from the group consisting of an oxide, oxyhalide or halide of a metal or metalloid from columns 4 to 15 of the Periodic Table, it may be activated prior to its use in step a). For example, said catalyst may be activated in the presence of oxygen, air, hydrogen iodide or HF or a mixture thereof.

The catalyst may also deactivate over time. Thus, step a) may be performed in the presence of oxygen or air or an oxygen-nitrogen mixture. If oxygen is used in step a), it is present in an amount of from 0.005 mol % to 10 mol % relative to the molar amount of fluoroolefin.

The catalyst may also be regenerated after the present process has been performed. The regeneration step may comprise placing the catalyst in contact with a stream of oxygen or air at a temperature of from 200° C. to 700° C.

Alternatively, step a) may be performed in the gas phase in the absence of a catalyst.

In the gas phase, in the presence or absence of a catalyst, step a) is performed at a temperature of from 150° C. to 700° C., preferably from 250° C. to 600° C.

Irrespective of whether step a) is performed in the gas phase in the presence or absence of a catalyst, the pressure in this step is from 0.1 bar to 30 bar, preferably from 1 bar to 20 bar, in particular from 1 bar to 15 bar.

Liquid Phase Step a)

Alternatively, step a) is performed in the liquid phase. The temperature at which step a) is performed in the liquid phase is from 50° C. to 280° C., preferably from 50° C. to 250° C.

Step a) may be performed in the presence of a solvent S1. Preferably, the solvent S1 is anhydrous. The term "anhydrous" refers here to a solvent S1 containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said solvent S1 is free of water. The solvent S1 has a boiling point of from 0° C. to 250° C., preferably from 20° C. to 250° C., in particular from 20° C. to 200° C. Said solvent S1 is chosen from the group consisting of acetic acid, $CCl_4$, chloroform, dichloromethane, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof.

According to one embodiment, step a) is performed in the presence of a catalyst chosen from alkali metal or alkaline-earth metal salts. Preferably, the catalyst is an alkali metal salt. Any alkali metal iodide may be used, but sodium iodide or potassium iodide is preferably used. The ratio between the catalyst and said olefin (preferably said fluoroolefin as described above) is between 1 and 20, preferably between 1 and 10. The catalyst preferably has a specific surface area of between 20 and 1000 $m^2/g$, in particular between 20 and 300 $m^2/g$. The catalyst may be deposited onto a porous support. The porous support may be chosen from activated charcoals, graphite, aluminas and alumina fluorides.

According to another embodiment, step a) is performed in the presence of a Lewis acid catalyst, a catalyst containing a halide of a metal, in particular a halide of antimony, tin, tantalum or titanium, or of a transition metal such as molybdenum, niobium or iron. For example, the catalyst may be $SbF_5$, $SbF_3$, $TiF_4$, $SnF_4$, $TaF_5$, $NbF_5$, $TiF_4$, $FeF_3$ or $MoF_6$. Preferably, the catalyst is liquid at the temperature at which step a) is performed. The presence of a solvent S1 is thus optional when these catalysts are used for performing step a).

According to another embodiment, the present process may be performed in the presence of a mixture of fluoroolefins as defined above to result in the production of a mixture of iodofluoroalkane compounds in said stream A and in said stream B1.

As mentioned above, step a) makes it possible to obtain a stream A comprising said iodofluoroalkane compound and optionally unreacted iodine monofluoride. When the iodine monofluoride is prepared by mixing anhydrous iodine ($I_2$) and anhydrous iodine pentafluoride ($IF_5$), said stream A may also comprise unreacted iodine and/or iodine pentafluoride. Stream A may also comprise other compounds such as impurities, reaction by-products (for example products derived from the addition of one or more iodine or fluorine atoms to one or more carbon atoms of the olefin) or even unreacted olefin.

Step b) of the Process

Said stream A is purified to form a stream B1 comprising at least 90% by weight of said iodofluoroalkane compound. Preferably, after purification, the content of said iodofluoroalkane compound in said stream B1 is greater than 92%, advantageously greater than 94%, preferably greater than 96%, more preferentially greater than 98%, in particular greater than 99%, more particularly greater than 99.5%. Said stream A is preferably purified by distillation, azeotropic distillation, distillation under pressure, extractive distillation, cold separation, absorption in a solvent or a combination thereof. Said stream A may also be purified by placing in contact with an adsorbent. Said adsorbent may be a zeolite or a molecular sieve having a pore aperture with an average diameter of between 3 ångströms and 11 ångströms, advantageously between 4 ångströms and 10 ångströms, preferably between 5 ångströms and 10 ångströms. The purification of said stream A may successively include one or more purification techniques as mentioned above, i.e. one or more distillations or combine, for example, a cold separation with a distillation, etc.

The purification of said stream A also results in the formation of a stream B2 comprising, for example, iodine monofluoride or comprising iodine and iodine pentafluoride if stream A contains any or unreacted olefin if the stream A contains any. Depending on the constituents of stream B2, it may be purified before performing step c) so as to remove impurities or reaction by-products formed during step a) and possibly present in said stream A before purification.

Preferably, said stream B2 comprises unreacted iodine and iodine pentafluoride and optionally unreacted iodine monofluoride and olefin.

Step c) of the Process

Step c) of the present process includes the recycling of stream B2 into step a). This recycling step improves the overall yield of the process (better conversion) and saves on expensive reagents (and catalysts), while at the same time minimizing the environmental impact. Without this recycling step, the unreacted iodine monofluoride (or the precursors thereof $I_2$ and $IF_5$) and/or olefin would have to be incinerated, thus increasing the carbon footprint of the process.

If stream B1 comprises unreacted olefin, said reagent can be removed from stream B1 and also be recycled into step a).

The present process may be performed continuously or in a batchwise or semi-batchwise manner.

Preferably, in order to avoid corrosion problems, the reactor, in which step a) is performed, is made of a material comprising a base layer made of a material M1 and an inner layer made of a material M2.

Advantageously, the material M2 comprises at least 40% by weight of nickel relative to the total weight of the material M2. Preferably, the material M2 comprises at least 45% by weight of nickel, more preferentially at least 50% by weight of nickel, in particular at least 55% by weight of nickel, more particularly at least 60% by weight of nickel, preferably at least 65% by weight of nickel, more preferably at least 70% by weight of nickel relative to the total weight of the material M2.

The material M2 may also comprise chromium in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

The material M2 may also comprise molybdenum in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

Preferably, the material M2 is Monel®, Hastelloy®, Inconel® or Incoloy®.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1. More particularly, the material M1 may comprise between 0.01% and 0.2% by weight of carbon on the basis of the total weight of the material M1.

Preferably, said base layer and said inner layer are placed against each other by hot or cold plating, hot or cold rolling or welding.

EXAMPLES

Example 1

Synthesis of $CF_3$—CFI—$CF_3$

The equipment used is composed of a Hastelloy C276 autoclave with a volume of 0.8 L, on which is mounted a condenser and a pressure-regulating valve. The autoclave was degassed and rendered inert with nitrogen, and the following constituents were successively introduced: 150 g (0.59 mol) of anhydrous iodine, 65 g (0.29 mol) of anhydrous iodine pentafluoride and 6.5 g (0.03 mol) of antimony pentafluoride ($SbF_5$). The autoclave was then stirred for 45 minutes and immersed in an oil bath and the temperature was raised to 80° C. while the condenser temperature was maintained at about 17° C. When the temperature of the reaction medium reached 80° C., 12.5 g/h (0.083 mol/h) of hexafluoropropene ($C_3F_6$) were continuously injected. During the reaction, the volatile products were removed continuously, washed and collected. After 6 hours of reaction, the autoclave was cooled to room temperature. It was then degassed and the reaction products were washed, dried and analyzed by gas chromatography (area percentage).

The yield of $CF_3$—CFI—$CF_3$, expressed by the ratio of the number of moles of $CF_3$—CFI—$CF_3$ detected to the number of moles of hexafluoropropene initially introduced, was 93.6%.

Example 2

Synthesis of $CF_3$—$CF_2$—$CH_2I$

The following were successively introduced into the same reaction assembly as in Example 1: 200 g (0.79 mol) of anhydrous iodine, 85 g (0.38 mol) of anhydrous iodine pentafluoride and 22.0 g (0.1 mol) of antimony pentafluoride ($SbF_5$). The autoclave was then stirred for 60 minutes and immersed in an oil bath and the temperature was raised to 80° C. while the condenser temperature was maintained at about 17° C. When the temperature of the reaction medium reached 80° C., 11.4 g/h (0.1 mol/h) of 2,3,3,3-tetrafluoropropene (HFO-1234yf) were continuously injected.

During the reaction, the volatile products were removed continuously, washed and collected. After 10 hours of reaction, the autoclave was cooled to room temperature. It was then degassed and the reaction products were washed, dried and analyzed by gas chromatography (area percentage).

The yield of $CF_3$—$CF_2$—$CH_2I$, expressed by the ratio of the number of moles of $CF_3$—$CF_2$—$CH_2I$ detected to the number of moles of $CF_3$—CF═$CH_2$ initially introduced, was 80.5%.

Invention III

Summary of Invention III

The present invention relates to a process for producing an iodofluoroalkane compound, comprising step a) of placing a hydrofluoroalkane in contact with anhydrous iodine to form a stream A comprising said iodofluoroalkane compound, hydrogen iodide (HI) and unreacted iodine. Step a) thus allows the substitution of a hydrogen atom of said hydrofluoroalkane with an iodine atom to form said iodofluoroalkane. Preferably, the hydrofluoroalkane consists of carbon, hydrogen and fluorine atoms.

According to a preferred embodiment, said process comprises a step b) during which said stream A is separated to form a stream B1 comprising said iodofluoroalkane compound and a stream B2 comprising unreacted iodine; the hydrogen iodide being contained in stream B1, or stream B2 or in both.

According to a preferred embodiment, said process comprises a step c) during which said stream B2 is recycled into step a).

According to a preferred embodiment, the hydrofluoroalkane is of formula (I) $(R^1)(R^2)CF(R^3)$ in which $R^1$, $R^2$ and $R^3$ are, independently of each other, chosen from the group consisting of H, F, a $C_1$-$C_{10}$ alkyl radical optionally substituted with at least one fluorine atom and a $C_3$-$C_{10}$ cycloalkyl radical optionally substituted with at least one fluorine atom; with the proviso that at least one of the substituents $R^1$, $R^2$ or $R^3$ is H or is a radical as defined above including at least one hydrogen atom.

According to a preferred embodiment, said iodofluoroalkane is of formula (II) $(R^1)(R^2)CF(R^3)$ in which $R^1$, $R^2$ and $R^3$ are, independently of each other, chosen from the group consisting of H, F, I, a $C_1$-$C_{10}$ alkyl radical optionally substituted with at least one fluorine atom and/or at least one iodine atom, and a $C_3$-$C_{10}$ cycloalkyl radical optionally substituted with at least one fluorine atom and/or at least one iodine atom; with the proviso that at least one of the substituents $R^1$, $R^2$ or $R^3$ is I or is a radical as defined above including at least one iodine atom.

According to a preferred embodiment, the hydrofluoroalkane is of formula (I) $(R^1)(R^2)CH(R^3)$ in which $R^1$, $R^2$ and $R^3$ are, independently of each other, chosen from the group consisting of H, F, a $C_1$-$C_5$ perfluoroalkyl radical and a $C_5$-$C_{10}$ perfluorocycloalkyl radical.

According to a preferred embodiment, said iodofluoroalkane compound is of formula (II) $(R^1)(R^2)$CFI in which Rand $R^2$ are, independently of each other, chosen from the group consisting of H, F, a $C_1$-$C_5$ perfluoroalkyl radical and a $C_5$-$C_{10}$ perfluorocycloalkyl radical.

According to a preferred embodiment, the hydrofluoroalkane is of formula (I) $(R^1)(R^2)CF(R^3)$ in which $R^1$, $R^2$ and $R^3$ are, independently of each other, chosen from the group consisting of H, F or $Y^1$—[—$C(Y^2)(Y^3)$—$]_n$— in which $Y^1$, $Y^2$ and $Y^3$ are, independently of each other and independently for each unit n, chosen from the group consisting of H and F; and n is an integer from 1 to 10; provided that at least one of the substituents $R^1$, $R^2$, $R^3$, $Y^1$, $Y^2$ or $Y^3$ is H.

According to a preferred embodiment, said iodofluoroalkane compound is of formula (II) $(R^1)(R^2)CF(R^3)$ in which $R^1$, $R^2$ and $R^3$ are, independently of each other, chosen from the group consisting of H, F, I or $Y^1$—[—$C(Y^2)(Y^3)$—$]_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $Y^1$, $Y^2$ or $Y^3$ is I.

According to a preferred embodiment, the hydrofluoroalkane compound is chosen from the group consisting of $CH_3F$, $CH_2F_2$, $CHF_3$, $CH_2F$—$CH_3$, $CHF_2$—$CH_3$, $CH_2F$—$CH_2F$, $CF_3$—$CH_3$, $CHF_2$—$CH_2F$, $CF_3$—$CH_2F$, $CHF_2$—$CHF_2$, $CF_3$—$CHF_2$, $CH_2F$—$CH_2$—$CH_3$, $CH_3$—CHF—$CH_3$, $CH_2F$—$CH_2$—$CH_2F$, $CHF_2$—$CH_2$—$CH_3$, $CH_2F$—CHF—$CH_3$, $CH_3$—$CF_2$—$CH_3$, $CHF_2$—$CH_2$—$CH_2F$, $CF_3$—$CH_2$—$CH_3$, $CH_2F$—CHF—$CH_2F$, $CHF_2$—CHF—$CH_3$, $CH_2F$—$CF_2$—$CH_3$, $CHF_2$—$CH_2$—$CHF_2$, $CF_3$—$CH_2$—$CH_2F$, $CHF_2$—CHF—$CH_2F$, $CF_3$—CHF—$CH_3$, $CH_2F$—$CF_2$—$CH_2F$, $CHF_2$—$CF_2$—$CH_3$, $CF_3$—$CH_2$—$CHF_2$, $CHF_2$—CHF—$CHF_2$, $CF_3$—CHF—$CH_2F$, $CHF_2$—$CF_2$—$CH_2F$, $CF_3$—$CF_2$—$CH_3$, $CF_3$—$CH_3$—$CF_3$, $CF_3$—CHF—$CHF_2$, $CHF_2$—$CF_2$—$CHF_2$, $CF_3$—$CF_2$—$CH_2F$, $CF_3$—CHF—$CF_3$, $CF_3$—$CF_2$—$CHF_2$; preferably from the group consisting of $CH_2F_2$, $CHF_3$, $CHF_2$—$CH_3$, $CF_3$—$CH_3$, $CF_3$—$CH_2F$, $CF_3$—$CHF_2$, $CH_2F$—CHF—$CH_3$, $CF_3$—$CH_2$—$CH_3$, $CF_3$—$CH_2$—$CH_2F$, $CF_3$—CHF—$CH_3$, $CF_3$—$CH_2$—$CHF_2$, $CF_3$—CHF—$CH_2F$, $CF_3$—$CH_2$—$CF_3$, $CF_3$—CHF—$CHF_2$, $CF_3$—CHF—$CF_3$.

According to a preferred embodiment, said iodofluoroalkane compound is chosen from the group consisting of $CH_2FI$, $CHFI_2$, $CHF_2I$, $CF_2I_2$, $CF_3$, CHFI—$CH_3$, $CH_2F$—$CH_2I$, $CFI_2$—$CH_3$, $CH_2F$—$CHI_2$, CHFI—$CH_2I$, $CF_2I$—$CH_3$, $CHF_2$—$CH_2I$, $CHF_2$—$CHI_2$, $CF_2I$—$CH_2I$, CHFI—$CH_2F$, $CFI_2$—$CH_2F$, CHFI—CHFI, $CF_3$—$CH_2I$, $CF_3$—$CHI_2$, $CF_2I$—$CH_2F$, $CHF_2$—CHFI, $CHF_2$—$CFI_2$, $CF_2I$—

CHFI, CF$_3$—CHFI, CF$_3$—CFI$_2$, CF$_2$I—CHF$_2$, CF$_2$I—CF$_2$I, CF$_3$—CF$_2$I, CHFI—CH$_2$—CH$_3$, CH$_2$F—CHI—CH$_3$, CH$_2$F—CH$_2$—CH$_2$I, CFI$_2$—CH$_2$—CH$_3$, CH$_2$F—CI$_2$—CH$_3$, CH$_2$F—CH$_2$—CHI$_2$, CHFI—CHI—CH$_3$, CHFI—CH$_2$—CH$_2$I, CH$_2$F—CHI—CH$_2$I, CH$_2$I—CHF—CH$_3$, CH$_3$—CFI—CH$_3$, CHI$_2$—CHF—CH$_3$, CH$_2$I—CFI—CH$_3$, CH$_2$I—CHF—CH$_2$I, CHFI—CH$_2$—CH$_2$F, CH$_2$F—CHI—CH$_2$F, CFI$_2$—CH$_2$—CH$_2$F, CH$_2$F—CI$_2$—CH$_2$F, CHFI—CHI—CH$_2$F, CHFI—CH$_2$—CHFI, CF$_2$I—CH$_2$—CH$_3$, CHF$_2$—CHI—CH$_3$, CHF$_2$—CH$_2$—CH$_2$I, CHF$_2$—CI$_2$—CH$_3$, CHF$_2$—CH$_2$—CHI$_2$, CF$_2$I—CHI—CH$_3$, CF$_2$I—CH$_2$—CH$_2$I, CHF$_2$—CHI—CH$_2$I, CHFI—CHF—CH$_3$, CH$_2$F—CFI—CH$_3$, CH$_2$F—CHF—CH$_2$I, CF$_2$—CHF—CH$_3$, CH$_2$F—CHF—CHI$_2$, CHFI—CFI—CH$_3$, CHFI—CHF—CH$_2$I, CH$_2$F—CFI—CH$_2$I, CH$_2$I—CF$_2$—CH$_3$, CHI$_2$—CF$_2$—CH$_3$, CH$_2$I—CF$_2$—CH$_2$I, CF$_2$I—CH$_2$—CH$_2$F, CHF$_2$—CHI—CH$_2$F, CHF$_2$—CH$_3$—CHFI, CHF$_2$—CI$_2$—CH$_2$F, CHF$_2$—CH$_2$—CFI$_2$, CF$_2$I—CHI—CH$_2$F, CF$_2$I—CH$_2$—CHFI, CHF$_2$—CHI—CHFI, CF$_3$—CHI—CH$_3$, CF$_3$—CH$_2$—CH$_2$I, CF$_3$—CI$_2$—CH$_3$, CF$_3$—CH$_2$—CHI$_2$, CF$_3$—CHI—CH$_2$I, CHFI—CHF—CH$_2$F, CH$_2$F—CFI—CH$_2$F, CFI$_2$—CHF—CH$_2$F, CHFI—CFI—CH$_2$F, CHFI—CHF—CHFI, CF$_2$I—CHF—CH$_3$, CHF$_2$—CFI—CH$_3$, CHF$_2$—CHF—CH$_2$I, CHF$_2$—CHF—CHI$_2$, CF$_2$I—CFI—CH$_3$, CF$_2$I—CHF—CH$_2$I, CHF$_2$—CFI—CH$_2$I, CHFI—CF$_2$—CH$_3$, CH$_2$F—CF$_2$—CH$_2$I, CFI$_2$—CF$_2$—CH$_3$, CH$_2$F—CF$_2$—CHI$_2$, CHFI—CF$_2$—CH$_2$I, CF$_2$I—CH$_2$—CHF$_2$, CHF$_2$—CHI—CHF$_2$, CHF$_2$—CI$_2$—CHF$_2$, CF$_2$I—CHI—CHF$_2$, CF$_2$I—CH$_3$—CF$_2$I, CF$_3$—CHI—CH$_2$F, CF$_3$—CH$_2$—CHFI, CF$_3$—CI$_2$—CH$_2$F, CF$_3$—CH$_2$—CFI$_2$, CF$_3$—CHI—CHFI, CF$_2$I—CHF—CH$_2$F, CHF$_2$—CFI—CH$_2$F, CHF$_2$—CHF—CHFI, CHF$_2$—CHF—CFI$_2$, CF$_2$I—CFI—CH$_2$F, CF$_2$I—CHF—CHFI, CHF$_2$—CFI—CHFI, CF$_3$—CFI—CH$_3$, CF$_3$—CHF—CH$_2$I, CF$_3$—CHF—CHI$_2$, CF$_3$—CFI—CH$_2$I, CHFI—CF$_2$—CH$_2$F, CFI$_2$—CF$_2$—CH$_2$F, CHFI—CF$_2$—CHFI, CF$_2$I—CF$_2$—CH$_3$, CHF$_2$—CF$_2$—CH$_2$I, CHF$_2$—CF$_2$—CH$_{12}$, CF$_2$I—CF$_2$—CH$_2$I, CF$_3$—CHI—CHF$_2$, CF$_3$—CH$_2$—CF$_2$I, CF$_3$—CI$_2$—CHF$_2$, CF$_3$—CHI—CF$_2$I, CF$_2$I—CHF—CHF$_2$, CHF$_2$—CFI—CHF$_2$, CF$_2$I—CFI—CHF$_2$, CF$_2$I—CHF—CF$_2$I, CF$_3$—CFI—CH$_2$F, CF$_3$—CHF—CHFI, CF$_3$—CHF—CFI$_2$, CF$_3$—CFI—CHFI, CF$_2$I—CF$_2$—CH$_2$F, CHF$_2$—CF$_2$—CHFI, CHF$_2$—CF$_2$—CFI$_2$, CF$_2$I—CF$_2$—CHFI, CF$_3$—CF$_2$—CH$_2$I, CF$_3$—CF$_2$—CHI$_2$, CF$_3$—CHI—CF$_3$, CF$_3$—CI$_2$—CF$_3$, CF$_3$—CFI—CHF$_2$, CF$_3$—CHF—CF$_2$I, CF$_3$—CFI—CF$_2$I, CF$_2$I—CF$_2$—CHF$_2$, CF$_2$I—CF$_2$—CF$_2$I, CF$_3$—CF$_2$—CHFI, CF$_3$—CF$_3$—CFI$_2$, CF$_3$—CFI—CF$_3$, CF$_3$—CF$_2$—CF$_2$I; advantageously, said iodofluoroalkane compound is chosen from the group consisting of CHF$_2$I, CF$_2$I$_2$, CF$_3$, CF$_2$I—CH$_3$, CHF$_2$—CH$_2$I, CHF$_2$—CHI$_2$, CF$_2$I—CH$_2$I, CF$_3$—CH$_2$I, CF$_3$—CHI$_2$, CF$_3$—CHFI, CF$_3$—CFI$_2$, CF$_3$—CF$_2$I, CHFI—CHF—CH$_3$, CH$_2$F—CFI—CH$_3$, CH$_2$F—CHF—CH$_2$I, CFI$_2$—CHF—CH$_3$, CH$_2$F—CHF—CHI$_2$, CHFI—CFI—CH$_3$, CHFI—CHF—CH$_2$I, CH$_2$F—CFI—CH$_2$I, CF$_3$—CHI—CH$_3$, CF$_3$—CH$_2$—CH$_2$I, CF$_3$—CI$_2$—CH$_3$, CF$_3$—CH$_2$—CHI$_2$, CF$_3$—CHI—CH$_2$I, CF$_3$—CHI—CH$_2$F, CF$_3$—CH$_3$—CHFI, CF$_3$—CI$_2$—CH$_2$F, CF$_3$—CH$_2$—CFI$_2$, CF$_3$—CHI—CHFI, CF$_3$—CFI—CH$_3$, CF$_3$—CHF—CH$_2$I, CF$_3$—CHF—CHI$_2$, CF$_3$—CFI—CH$_2$I, CF$_3$—CHI—CHF$_2$, CF$_3$—CH$_2$—CF$_2$I, CF$_3$—CI$_2$—CHF$_2$, CF$_3$—CHI—CF$_2$I, CF$_3$—CFI—CH$_2$F, CF$_3$—CHF—CHFI, CF$_3$—CHF—CFI$_2$, CF$_3$—CFI—CHFI, CF$_3$—CHI—CF$_3$, CF$_3$—CI$_2$—CF$_3$, CF$_3$—CFI—CHF$_2$, CF$_3$—CHF—CF$_2$I, CF$_3$—CFI—CF$_2$I, CF$_3$—CFI—CF$_3$; preferably, said iodofluoroalkane compound is chosen from the group consisting of CH$_2$FI, CHF$_2$I, CF$_3$, CHFI—CH$_3$, CF$_2$I—CH$_3$, CHFI—CH$_2$F, CF$_3$—CH$_2$I, CF$_2$I—CH$_2$F, CF$_3$—CHFI, CF$_2$I—CHF$_2$, CF$_3$—CF$_2$I, CHFI—CH$_2$—CH$_3$, CH$_3$—CFI—CH$_3$, CHFI—CH$_2$—CH$_2$F, CF$_2$I—CH$_2$—CH$_3$, CHFI—CHF—CH$_3$, CH$_2$I—CF$_2$—CH$_3$, CF$_2$I—CH$_2$—CH$_2$F, CF$_3$—CH$_3$—CH$_2$I, CHFI—CHF—CH$_2$F, CF$_2$I—CHF—CH$_3$, CHFI—CF$_2$—CH$_3$, CF$_2$I—CH$_2$—CHF$_2$, CF$_3$—CH$_2$—CHFI, CF$_2$I—CHF—CH$_2$F, CF$_3$—CFI—CH$_3$, CHFI—CF$_2$—CH$_2$F, CF$_2$I—CF$_2$—CH$_3$, CF$_3$—CH$_2$—CF$_2$I, CF$_2$I—CHF—CHF$_2$, CF$_3$—CHF—CHFI, CF$_2$I—CF$_2$—CH$_2$F, CF$_3$—CF$_2$—CH$_2$I, CF$_3$—CHI—CF$_3$, CF$_3$—CHF—CF$_2$I, CF$_2$I—CF$_2$—CHF$_2$, CF$_3$—CF$_3$—CHFI, CF$_3$—CFI—CF$_3$, CF$_3$—CF$_3$—CF$_2$I; in particular, said iodofluoroalkane compound is chosen from the group consisting of CHF$_2$I, CF$_3$, CF$_2$I—CH$_3$, CF$_3$—CH$_2$I, CF$_3$—CHFI, CF$_3$—CF$_2$I, CHFI—CHF—CH$_3$, CF$_3$—CH$_2$—CH$_2$I, CF$_3$—CH$_2$—CHFI, CF$_3$—CFI—CH$_3$, CF$_3$—CH$_2$—CF$_2$I, CF$_3$—CHF—CHFI, CF$_3$—CHI—CF$_3$, CF$_3$—CHF—CF$_2$I, CF$_3$—CFI—CF$_3$.

According to a preferred embodiment, step a) involves one of the following reactions:

- converting CH$_2$F$_2$ into CHF$_2$I or CF$_2$I$_2$ or a mixture of the two; preferably into CHF$_2$I;
- converting CHF$_3$ into CF$_3$;
- converting CHF$_2$—CH$_3$ into CF$_2$I—CH$_3$ or CHF$_2$—CH$_2$I or CHF$_2$—CHI$_2$ or CF$_2$I—CH$_2$I or a mixture thereof; preferably into CF$_2$I—CH$_3$;
- converting CF$_3$—CH$_3$ into CF$_3$—CH$_2$I or CF$_3$—CHI$_2$ or a mixture of the two; preferably into CF$_3$—CH$_2$I;
- converting CF$_3$—CH$_2$F into CF$_3$—CHFI or CF$_3$—CFI$_2$ or a mixture of the two; preferably into CF$_3$—CHFI;
- converting CF$_3$—CHF$_2$ into CF$_3$—CF$_2$I;
- converting CH$_2$F—CHF—CH$_3$ into CHFI—CHF—CH$_3$ or CH$_2$F—CFI—CH$_3$ or CH$_2$F—CHF—CH$_2$I or CFI$_2$—CHF—CH$_3$ or CH$_2$F—CHF—CHI$_2$ or CHFI—CFI—CH$_3$ or CHFI—CHF—CH$_2$I or CH$_2$F—CFI—CH$_2$I or a mixture thereof; preferably into CHFI—CHF—CH$_3$;
- converting CF$_3$—CH$_2$—CH$_3$ into CF$_3$—CHI—CH$_3$ or CF$_3$—CH$_2$—CH$_2$I or CF$_3$—CI$_2$—CH$_3$ or CF$_3$—CH$_2$—CHI$_2$ or CF$_3$—CHI—CH$_2$I or a mixture thereof; preferably into CF$_3$—CH$_2$—CH$_2$I;
- converting CF$_3$—CH$_2$—CH$_2$F into CF$_3$—CHI—CH$_2$F or CF$_3$—CH$_2$—CHFI or CF$_3$—CI$_2$—CH$_2$F or CF$_3$—CH$_2$—CFI$_2$ or CF$_3$—CHI—CHFI or a mixture thereof; preferably into CF$_3$—CH$_2$—CHFI;
- converting CF$_3$—CHF—CH$_3$ into CF$_3$—CFI—CH$_3$ or CF$_3$—CHF—CH$_2$I or CF$_3$—CHF—CHI$_2$ or CF$_3$—CFI—CH$_2$I or a mixture thereof; preferably into CF$_3$—CFI—CH$_3$;
- converting CF$_3$—CH$_2$—CHF$_2$ into CF$_3$—CHI—CHF$_2$ or CF$_3$—CH$_2$—CF$_2$I or CF$_3$—CI$_2$—CHF$_2$ or CF$_3$—CHI—CF$_2$I or a mixture thereof; preferably into CF$_3$—CH$_2$—CF$_2$I;
- converting CF$_3$—CHF—CH$_2$F into CF$_3$—CFI—CH$_2$F or CF$_3$—CHF—CHFI or CF$_3$—CHF—CFI$_2$ or CF$_3$—CFI—CHFI or a mixture thereof; preferably into CF$_3$—CHF—CHFI;
- converting CF$_3$—CH$_2$—CF$_3$ into CF$_3$—CHI—CF$_3$ or CF$_3$—CI$_2$—CF$_3$ or a mixture of the two; preferably into CF$_3$—CHI—CF$_3$;
- converting CF$_3$—CHF—CHF$_2$ into CF$_3$—CFI—CHF$_2$ or CF$_3$—CHF—CF$_2$I or CF$_3$—CFI—CF$_2$I or a mixture thereof; preferably into CF$_3$—CHF—CF$_2$I; or
- converting CF$_3$—CHF—CF$_3$ into CF$_3$—CFI—CF$_3$.

According to a preferred embodiment, step a) is performed in the presence of a catalyst chosen from antimony halides, iron halides, titanium halides or tin halides; oxides, oxyhalides or halides of chromium or aluminum; and alkali metal or alkaline-earth metal salts, or a mixture thereof.

According to a preferred embodiment, step a) is performed in the gas phase at a temperature from 250° C. to 700° C.

According to a preferred embodiment, step a) is performed in the liquid phase in the presence of a polar aprotic solvent, preferably at a temperature from 50° C. to 300° C.

Detailed Description of Invention III

The present invention relates to a process for producing an iodofluoroalkane compound. In particular, said process involves placing a hydrofluoroalkane in contact with anhydrous iodine.

Said step a) thus results in the formation of a stream A comprising said iodofluoroalkane compound, hydrogen iodide and unreacted iodine.

Preferably, said process also comprises steps of separating the compounds contained in stream A. Said process may also comprise a step of recycling the starting reagents.

Thus, preferably, said process comprises the steps of:

a) placing a hydrofluoroalkane in contact with anhydrous iodine to form a stream A comprising said iodofluoroalkane compound, hydrogen iodide (HI) and unreacted iodine;

b) separating said stream A to form a stream B1 comprising said iodofluoroalkane compound and a stream B2 comprising unreacted iodine; the hydrogen iodide being contained in stream B1, or stream B2 or in both.

c) recycling of said stream B2 into step a).

Step a) of the Process

Step a) of the present process requires a hydrofluoroalkane to be placed in contact with anhydrous iodine. The term "anhydrous" refers here to iodine containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said iodine is free of water. The use of anhydrous iodine in the present process prevents the formation of impurities.

The hydrofluoroalkane is preferably of formula (I) $(R^1)(R^2)CF(R^3)$ in which $R^1$, $R^2$ and $R^3$ are, independently of each other, chosen from the group consisting of H, F, a $C_1$-$C_{10}$ alkyl radical optionally substituted with at least one fluorine atom and a $C_3$-$C_{10}$ cycloalkyl radical optionally substituted with at least one fluorine atom; with the proviso that at least one of the substituents $R^1$, $R^2$ or $R^3$ is H or is a radical as defined above including at least one hydrogen atom.

The term "alkyl" denotes a monovalent radical resulting from a linear or branched alkane comprising the number of carbon atoms specified. The term "cycloalkyl" denotes a monovalent radical resulting from a cycloalkane comprising the number of carbon atoms specified.

Preferably, said alkyl or cycloalkyl radical is not substituted with functional groups other than fluorine. Said radical may nevertheless comprise several fluorine atoms on its carbon chain, for example, said radical may contain from 1 to 5 fluorine atoms, preferably from 1 to 3 fluorine atoms.

More preferentially, the hydrofluoroalkane is of formula (I) $(R^1)(R^2)CF(R^3)$ in which $R^1$, $R^2$ and $R^3$ are, independently of each other, chosen from the group consisting of H, F, a $C_1$-$C_{10}$ alkyl radical optionally substituted with 1 to 10 fluorine atoms and a $C_3$-$C_{10}$ cycloalkyl radical optionally substituted with 1 to 10 fluorine atoms; with the proviso that at least one of the substituents $R^1$, $R^2$ or $R^3$ is H or is a radical as defined above including at least one hydrogen atom.

In particular, the hydrofluoroalkane is of formula (I) $(R^1)(R^2)CF(R^3)$ in which $R^1$, $R^2$ and $R^3$ are, independently of each other, chosen from the group consisting of H, F, a $C_1$-$C_5$ alkyl radical optionally substituted with 1 to 5 fluorine atoms and a $C_5$-$C_{10}$ cycloalkyl radical optionally substituted with 1 to 5 fluorine atoms; with the proviso that at least one of the substituents $R^1$, $R^2$ or $R^3$ is H or is a radical as defined above including at least one hydrogen atom.

Thus, advantageously, said iodofluoroalkane compound is of formula (II) $(R^1)(R^2)CF(R^3)$ in which $R^1$, $R^2$ and $R^3$ are, independently of each other, chosen from the group consisting of H, F, I, a $C_1$-$C_{10}$ alkyl radical optionally substituted with at least one fluorine atom and/or at least one iodine atom, and a $C_3$-$C_{10}$ cycloalkyl radical optionally substituted with at least one fluorine atom and/or at least one iodine atom; with the proviso that at least one of the substituents $R^1$, $R^2$ or $R^3$ is I or is a radical as defined above including at least one iodine atom.

Preferably, said iodofluoroalkane compound is of formula (II) $(R^1)(R^2)CF(R^3)$ in which $R^1$, $R^2$ and $R^3$ are, independently of each other, chosen from the group consisting of H, F, I, a $C_1$-$C_{10}$ alkyl radical optionally substituted with 1 to 10 fluorine atoms and/or at least one iodine atom, and a $C_3$-$C_{10}$ cycloalkyl radical optionally substituted with 1 to 10 fluorine atoms and/or at least one iodine atom; with the proviso that at least one of the substituents $R^1$, $R^2$ or $R^3$ is I or is a radical as defined above including at least one iodine atom.

In particular, said iodofluoroalkane compound is of formula (II) $(R^1)(R^2)CF(R^3)$ in which $R^1$, $R^2$ and $R^3$ are, independently of each other, chosen from the group consisting of H, F, I, a $C_1$-$C_{10}$ alkyl radical optionally substituted with 1 to 5 fluorine atoms and/or at least one iodine atom, and a $C_3$-$C_{10}$ cycloalkyl radical optionally substituted with 1 to 5 fluorine atoms and/or at least one iodine atom; with the proviso that at least one of the substituents $R^1$, $R^2$ or $R^3$ is I or is a radical as defined above including at least one iodine atom.

According to a preferred embodiment, the hydrofluoroalkane is of formula (I) $(R^1)(R^2)CH(R^3)$ in which $R^1$, $R^2$ and $R^3$ are, independently of each other, chosen from the group consisting of H, F, a $C_1$-$C_{10}$ perfluoroalkyl radical and a $C_3$-$C_{10}$ perfluorocycloalkyl radical. Preferably, the hydrofluoroalkane is of formula (I) $(R^1)(R^2)CH(R^3)$ in which $R^1$, $R^2$ and $R^3$ are, independently of each other, chosen from the group consisting of H, F, a $C_1$-$C_5$ perfluoroalkyl radical and a $C_5$-$C_{10}$ perfluorocycloalkyl radical.

In this embodiment, said iodofluoroalkane compound is of formula (II) $(R^1)(R^2)C(R^3)I$ in which $R^1$ and $R^2$ are, independently of each other, chosen from the group consisting of H, F, a $C_1$-$C_{10}$ perfluoroalkyl radical and a $C_3$-$C_{10}$ perfluorocycloalkyl radical. Preferably, said iodofluoroalkane compound is of formula (II) $(R^1)(R^2)C(R^3)I$ in which $R^1$ and $R^2$ are, independently of each other, chosen from the group consisting of H, F, a $C_1$-$C_5$ perfluoroalkyl radical and a $C_5$-$C_{10}$ perfluorocycloalkyl radical.

According to another preferred embodiment, the hydrofluoroalkane is of formula (I) $(R^1)(R^2)CF(R^3)$ in which $R^1$, $R^2$ and $R^3$ are, independently of each other chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 10;

provided that at least one of the substituents $R^1$, $R^2$, $R^3$, $Y^1$, $Y^2$ or $Y^3$ is H. Preferably, the hydrofluoroalkane is of formula (I) $(R^1)(R^2)CF(R^3)$ in which $R^1$, $R^2$ and $R^3$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $Y^1$, $Y^2$ or $Y^3$ is H.

In this embodiment, said iodofluoroalkane compound is of formula (II) $(R^1)(R^2)CF(R^3)$ in which $R^1$, $R^2$ and $R^3$ are, independently of each other, chosen from the group consisting of H, F, I or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $Y^1$, $Y^2$ or $Y^3$ is I. Preferably, said iodofluoroalkane compound is of formula (II) $(R^1)(R^2)CF(R^3)$ in which $R^1$, $R^2$ and $R^3$ are, independently of each other, chosen from the group consisting of H, F, I or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $Y^1$, $Y^2$ or $Y^3$ is I.

According to another preferred embodiment, the hydrofluoroalkane is chosen from the group consisting of $CH_3F$, $CH_2F_2$, $CHF_3$, $CH_2F$—$CH_3$, $CHF_2$—$CH_3$, $CH_2F$—$CH_2F$, $CF_3$—$CH_3$, $CHF_2$—$CH_2F$, $CF_3$—$CH_2F$, $CHF_2$—$CHF_2$, $CF_3$—$CHF_2$, $CH_2F$—$CH_3$—$CH_3$, $CH_3$—CHF—$CH_3$, $CH_2F$—$CH_2$—$CH_2F$, $CHF_2$—$CH_3$—$CH_3$, $CH_2F$—CHF—$CH_3$, $CH_3$—$CF_2$—$CH_3$, $CHF_2$—$CH_3$—$CH_2F$, $CF_2$—$CH_2$—$CH_3$, $CH_2F$—CHF—$CH_2F$, $CHF_2$—CHF—$CH_3$, $CH_2F$—$CF_2$—$CH_3$, $CHF_2$—$CH_3$—$CHF_2$, $CF_3$—$CH_3$—$CH_2F$, $CHF_2$—CHF—$CH_2F$, $CF_3$—CHF—$CH_3$, $CH_2F$—$CF_2$—$CH_2F$, $CHF_2$—$CF_2$—$CH_3$, $CF_2$—$CH_2$—$CHF_2$, $CHF_2$—CHF—$CHF_2$, $CF_3$—CHF—$CH_2F$, $CHF_2$—$CF_2$—$CH_2F$, $CF_3$—$CF_2$—$CH_3$, $CF_3$—$CH_3$—$CF_3$, $CF_3$—CHF—$CHF_2$, $CHF_2$—$CF_2$—$CHF_2$, $CF_3$—$CF_2$—$CH_2F$, $CF_3$—CHF—$CF_3$, $CF_3$—$CF_2$—$CHF_2$; preferably from the group consisting of $CH_2F_2$, $CHF_3$, $CHF_2$—$CH_3$, $CF_3$—$CH_3$, $CF_3$—$CH_2F$, $CF_3$—$CHF_2$, $CH_2F$—CHF—$CH_3$, $CF_3$—$CH_3$—$CH_3$, $CF_3$—$CH_2$—$CH_2F$, $CF_3$—CHF—$CH_3$, $CF_3$—$CH_2$—$CHF_2$, $CF_3$—CHF—$CH_2F$, $CF_3$—$CH_3$—$CF_3$, $CF_3$—CHF—$CHF_2$, $CF_3$—CHF—$CF_3$.

In this preferred embodiment, said iodofluoroalkane compound is chosen from the group consisting of $CH_2FI$, $CHFI_2$, $CHF_2I$, $CF_2I_2$, $CF_3$, CHFI—$CH_3$, $CH_2F$—$CH_2I$, $CFI_2$—$CH_3$, $CH_2F$—$CHI_2$, CHFI—$CH_2I$, $CF_2I$—$CH_3$, $CHF_2$—$CH_2I$, $CHF_2$—$CHI_2$, $CF_2I$—$CH_2I$, CHFI—$CH_2F$, $CFI_2$—$CH_2F$, CHFI—CHFI, $CF_3$—$CH_2I$, $CF_3$—$CHI_2$, $CF_2I$—$CH_2F$, $CHF_2$—CHFI, $CHF_2$—$CFI_2$, $CF_2I$—CHFI, $CF_3$—CHFI, $CF_3$—$CFI_2$, $CF_2I$—$CHF_2$, $CF_2I$—$CF_2I$, $CF_3$—$CF_2I$, CHFI—$CH_2$—$CH_3$, $CH_2F$—CHI—$CH_3$, $CH_2F$—$CH_2$—$CH_2I$, $CFI_2$—$CH_2$—$CH_3$, $CH_2F$—$CI_2$—$CH_3$, $CH_2F$—$CH_2$—$CHI_2$, CHFI—CHI—$CH_3$, CHFI—$CH_2$—$CH_2I$, $CH_2F$—CHI—$CH_2I$, $CH_2I$—CHF—$CH_3$, $CH_3$—CFI—$CH_3$, $CHI_2$—CHF—$CH_3$, $CH_2I$—CFI—$CH_3$, $CH_2I$—CHF—$CH_2I$, CHFI—$CH_2$—$CH_2F$, $CH_2F$—CHI—$CH_2F$, $CFI_2$—$CH_2$—$CH_2F$, $CH_2F$—$CI_2$—$CH_2F$, CHFI—CHI—$CH_2F$, CHFI—$CH_2$—CHFI, $CF_2I$—$CH_2$—$CH_3$, $CHF_2$—CHI—$CH_3$, $CHF_2$—$CH_3$—$CH_2I$, $CHF_2$—$CI_2$—$CH_3$, $CHF_2$—$CH_3$—$CHI_2$, $CF_2I$—CHI—$CH_3$, $CF_2I$—$CH_2$—$CH_2I$, $CHF_2$—CHI—$CH_2I$, CHFI—CHF—$CH_3$, $CH_2F$—CFI—$CH_3$, $CH_2F$—CHF—$CH_2I$, $CFI_2$—CHF—$CH_3$, $CH_2F$—CHF—$CHI_2$, CHFI—CFI—$CH_3$, CHFI—CHF—$CH_2I$, $CH_2F$—CFI—$CH_2I$, $CH_2I$—$CF_2$—$CH_3$, $CH_2$—$CF_2$—$CH_3$, $CH_2I$—$CF_2$—$CH_2I$, $CF_2I$—$CH_2$—$CH_2F$, $CHF_2$—CHI—$CH_2F$, $CHF_2$—$CH_2$—CHFI, $CHF_2$—$CI_2$—$CH_2F$, $CHF_2$—$CH_2$—$CFI_2$, $CF_2I$—CHI—$CH_2F$, $CF_2I$—$CH_2$—CHFI, $CHF_2$—CHI—CHFI, $CF_3$—CHI—$CH_3$, $CF_3$—$CH_2$—$CH_2I$, $CF_3$—$CI_2$—$CH_3$, $CF_3$—$CH_2$—$CHI_2$, $CF_3$—CHI—$CH_2I$, CHFI—CHF—$CH_2F$, $CH_2F$—CFI—$CH_2F$, $CFI_2$—CHF—$CH_2F$, CHFI—CFI—$CH_2F$, CHFI—CHF—CHFI, $CF_2I$—CHF—$CH_3$, $CHF_2$—CFI—$CH_3$, $CHF_2$—CHF—$CH_2I$, $CHF_2$—CHF—$CHI_2$, $CF_2I$—CFI—$CH_3$, $CF_2I$—CHF—$CH_2I$, $CHF_2$—CFI—$CH_2I$, CHFI—$CF_2$—$CH_3$, $CH_2F$—$CF_2$—$CH_2I$, $CFI_2$—$CF_2$—$CH_3$, $CH_2F$—$CF_2$—$CHI_2$, CHFI—$CF_2$—$CH_2I$, $CF_2I$—$CH_2$—$CHF_2$, $CHF_2$—CHI—$CHF_2$, $CHF_2$—$CI_2$—$CHF_2$, $CF_2I$—CHI—$CHF_2$, $CF_2I$—$CH_2$—$CF_2I$, $CF_3$—CHI—$CH_2F$, $CF_3$—$CH_2$—CHFI, $CF_3$—$CI_2$—$CH_2F$, $CF_3$—$CH_3$—$CFI_2$, $CF_3$—CHI—CHFI, $CF_2I$—CHF—$CH_2F$, $CHF_2$—CFI—$CH_2F$, $CHF_2$—CHF—CHFI, $CHF_2$—CHF—$CFI_2$, $CF_2I$—CFI—$CH_2F$, $CF_2I$—CHF—CHFI, $CHF_2$—CFI—CHFI, $CF_3$—CFI—$CH_3$, $CF_3$—CHF—$CH_2I$, $CF_3$—CHF—$CH_{12}$, $CF_3$—CFI—$CH_2I$, CHFI—$CF_2$—$CH_2F$, $CFI_2$—$CF_2$—$CH_2F$, CHFI—$CF_2$—CHFI, $CF_2I$—$CF_2$—$CH_3$, $CHF_2$—$CF_2$—$CH_2I$, $CHF_2$—$CF_2$—$CHI_2$, $CF_2I$—$CF_2$—$CH_2I$, $CF_3$—CHI—$CHF_2$, $CF_3$—$CH_2$—$CF_2I$, $CF_3$—$CI_2$—$CHF_2$, $CF_3$—CHI—$CF_2I$, $CF_2I$—CHF—$CHF_2$, $CHF_2$—CFI—$CHF_2$, $CF_2I$—CFI—$CHF_2$, $CF_2I$—CHF—$CF_2I$, $CF_3$—CFI—$CH_2F$, $CF_3$—CHF—CHFI, $CF_3$—CHF—$CFI_2$, $CF_3$—CFI—CHFI, $CF_2I$—$CF_2$—$CH_2F$, $CHF_2$—$CF_2$—CHFI, $CHF_2$—$CF_2$—$CFI_2$, $CF_2I$—$CF_2$—CHFI, $CF_3$—$CF_2$—$CH_2I$, $CF_3$—$CF_2$—$CHI_2$, $CF_3$—CHI—$CF_3$, $CF_3$—$CI_2$—$CF_3$, $CF_3$—CFI—$CHF_2$, $CF_3$—CHF—$CF_2I$, $CF_3$—CFI—$CF_2I$, $CF_2I$—$CF_2$—$CHF_2$, $CF_2I$—$CF_2$—$CF_2I$, $CF_3$—$CF_2$—CHFI, $CF_3$—$CF_2$—$CFI_2$, $CF_3$—CFI—$CF_3$, $CF_3$—$CF_2$—$CF_2I$; advantageously, said iodofluoroalkane compound is chosen from the group consisting of $CHF_2I$, $CF_2I_2$, $CF_3a$, $CF_2I$—$CH_3$, $CHF_2$—$CH_2I$, $CHF_2$—$CHI_2$, $CF_2I$—$CH_2I$, $CF_3$—$CH_2I$, $CF_3$—$CHI_2$, $CF_3$—CHFI, $CF_3$—$CFI_2$, $CF_3$—$CF_2I$, CHFI—CHF—$CH_3$, $CH_2F$—CFI—$CH_3$, $CH_2F$—CHF—$CH_2I$, $CFI_2$—CHF—$CH_3$, $CH_2F$—CHF—$CHI_2$, CHFI—CFI—$CH_3$, CHFI—CHF—$CH_2I$, $CH_2F$—CFI—$CH_2I$, $CF_3$—CHI—$CH_3$, $CF_3$—$CH_2$—$CH_2I$, $CF_3$—$CI_2$—$CH_3$, $CF_3$—$CH_2$—$CHI_2$, $CF_3$—CHI—$CH_2I$, $CF_3$—CHI—$CH_2F$, $CF_3$—$CH_2$—CHFI, $CF_3$—$CI_2$—$CH_2F$, $CF_3$—$CH_2$—$CFI_2$, $CF_2$—CHI—CHFI, $CF_3$—CFI—$CH_3$, $CF_3$—CHF—$CH_2I$, $CF_3$—CHF—$CHI_2$, $CF_3$—CFI—$CH_2I$, $CF_3$—CHI—$CHF_2$, $CF_3$—$CH_2$—$CF_2I$, $CF_3$—$CI_2$—$CHF_2$, $CF_3$—CHI—$CF_2I$, $CF_3$—CFI—$CH_2F$, $CF_3$—CHF—CHFI, $CF_3$—CHF—$CFI_2$, $CF_3$—CFI—CHFI, $CF_3$—CHI—$CF_3$, $CF_3$—$CI_2$—$CF_3$, $CF_3$—CFI—$CHF_2$, $CF_3$—CHF—$CF_2I$, $CF_3$—CFI—$CF_2I$, $CF_3$—CFI—$CF_3$; preferably, said iodofluoroalkane compound is chosen from the group consisting of $CH_2FI$, $CHF_2I$, $CF_3$, CHFI—$CH_3$, $CF_2I$—$CH_3$, CHFI—$CH_2F$, $CF_3$—$CH_2I$, $CF_2I$—$CH_2F$, $CF_3$—CHFI, $CF_2I$—$CHF_2$, $CF_3$—$CF_2I$, CHFI—$CH_2$—$CH_3$, $CH_3$—$CF_1$—$CH_3$, CHFI—$CH_2$—$CH_2F$, $CF_2I$—$CH_2$—$CH_3$, CHFI—CHF—$CH_3$, $CH_2I$—$CF_2$—$CH_3$, $CF_2I$—$CH_2$—$CH_2F$, $CF_3$—$CH_2$—$CH_2I$, CHFI—CHF—$CH_2F$, $CF_2I$—CHF—$CH_3$, CHFI—$CF_2$—$CH_3$, $CF_2I$—$CH_2$—$CHF_2$, $CF_3$—$CH_2$—CHFI, $CF_2I$—CHF—$CH_2F$, $CF_3$—CFI—$CH_3$, CHFI—$CF_2$—$CH_2F$, $CF_2I$—$CF_2$—$CH_3$, $CF_3$—$CH_2$—$CF_2I$, $CF_2I$—CHF—$CHF_2$, $CF_3$—CHF—CHFI, $CF_2I$—$CF_2$—$CH_2F$, $CF_3$—$CF_2$—$CH_2I$, $CF_3$—CHI—$CF_3$, $CF_3$—CHF—$CF_2I$, $CF_2I$—$CF_2$—$CHF_2$, $CF_3$—$CF_2$—CHFI, $CF_3$—CFI—$CF_3$, $CF_3$—$CF_3$—$CF_2I$; in particular, said iodofluoroalkane compound is chosen from the group consisting of $CHF_2I$, $CF_3$, $CF_2I$—$CH_3$, $CF_3$—$CH_2I$, $CF_3$—CHFI, $CF_3$—$CF_2I$, CHFI—CHF—$CH_3$, $CF_3$—$CH_2$—$CH_2I$, $CF_3$—$CH_2$—

CHFI, $CF_3$—CFI—$CH_3$, $CF_3$—$CH_2$—$CF_2I$, $CF_3$—CHF—CHFI, $CF_3$—CHI—$CF_3$, $CF_3$—CHF—$CF_2I$, $CF_3$—CFI—$CF_3$.

According to a particularly preferred embodiment, step a) of the present process involves one of the following reactions:

- converting $CH_2F_2$ into $CHF_2I$ or $CF_2I_2$ or a mixture of the two; preferably into $CHF_2I$;
- converting $CHF_3$ into $CF_3$;
- converting $CHF_2$—$CH_3$ into $CF_2I$—$CH_3$ or $CHF_2$—$CH_2I$ or $CHF_2$—$CHI_2$ or $CF_2I$—$CH_2I$ or a mixture thereof; preferably into $CF_2I$—$CH_3$;
- converting $CF_3$—$CH_3$ into $CF_3$—$CH_2I$ or $CF_3$—$CHI_2$ or a mixture of the two; preferably into $CF_3$—$CH_2I$;
- converting $CF_3$—$CH_2F$ into $CF_3$—CHFI or $CF_3$—$CFI_2$ or a mixture of the two; preferably into $CF_3$—CHFI;
- converting $CF_3$—$CHF_2$ into $CF_3$—$CF_2I$;
- converting $CH_2F$—CHF—$CH_3$ into CHFI—CHF—$CH_3$ or $CH_2F$—CFI—$CH_3$ or $CH_2F$—CHF—$CH_2I$ or $CFI_2$—CHF—$CH_3$ or $CH_2F$—CHF—$CHI_2$ or CHFI—CFI—$CH_3$ or CHFI—CHF—$CH_2I$ or $CH_2F$—CFI—$CH_2I$ or a mixture thereof; preferably into CHFI—CHF—$CH_3$;
- converting $CF_3$—$CH_2$—$CH_3$ into $CF_3$—CHI—$CH_3$ or $CF_3$—$CH_2$—$CH_2I$ or $CF_3$—$CI_2$—$CH_3$ or $CF_3$—$CH_2$—$CHI_2$ or $CF_3$—CHI—$CH_2I$ or a mixture thereof; preferably into $CF_3$—$CH_2$—$CH_2I$;
- converting $CF_3$—$CH_2$—$CH_2F$ into $CF_3$—CHI—$CH_2F$ or $CF_3$—$CH_2$—CHFI or $CF_3$—$CI_2$—$CH_2F$ or $CF_3$—$CH_2$—$CFI_2$ or $CF_3$—CHI—CHFI or a mixture thereof; preferably into $CF_3$—$CH_2$—CHFI;
- converting $CF_3$—CHF—$CH_3$ into $CF_3$—CFI—$CH_3$ or $CF_3$—CHF—$CH_2I$ or $CF_3$—CHF—$CHI_2$ or $CF_3$—CFI—$CH_2I$ or a mixture thereof; preferably into $CF_3$—CFI—$CH_3$;
- converting $CF_3$—$CH_2$—$CHF_2$ into $CF_3$—CHI—$CHF_2$ or $CF_3$—$CH_2$—$CF_2I$ or $CF_3$—$CI_2$—$CHF_2$ or $CF_3$—CHI—$CF_2I$ or a mixture thereof; preferably into $CF_3$—$CH_2$—$CF_2I$;
- converting $CF_3$—CHF—$CH_2F$ into $CF_3$—CFI—$CH_2F$ or $CF_3$—CHF—CHFI or $CF_3$—CHF—$CFI_2$ or $CF_3$—CFI—CHFI or a mixture thereof; preferably into $CF_3$—CHF—CHFI;
- converting $CF_3$—$CH_3$—$CF_3$ into $CF_3$—CHI—$CF_3$ or $CF_3$—$CI_2$—$CF_3$ or a mixture of the two; preferably into $CF_3$—CHI—$CF_3$;
- converting $CF_3$—CHF—$CHF_2$ into $CF_3$—CFI—$CHF_2$ or $CF_3$—CHF—$CF_2I$ or $CF_3$—CFI—$CF_2I$ or a mixture thereof; preferably into $CF_3$—CHF—$CF_2I$; or
- converting $CF_3$—CHF—$CF_3$ into $CF_3$—CFI—$CF_3$.

Preferably, step a) is performed in the presence of an anhydrous hydrofluoroalkane. The term "anhydrous" refers here to a hydrofluoroalkane containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said hydrofluoroalkane is free of water. The use of anhydrous iodine and of anhydrous hydrofluoroalkane in the present process prevents the formation of impurities and improves the reaction selectivity.

Preferably, the iodine ($I_2$) is placed in contact with said hydrofluoroalkane at stoichiometry or in excess thereof. For example, the $I_2$/hydrofluoroalkane mole ratio is from 1 to 50, preferably from 2 to 25, in particular from 5 to 20.

Alternatively, the iodine may be in deficit relative to said hydrofluoroalkane. In this case, said streams A and B2 comprise said unreacted hydrofluoroalkane instead of unreacted iodine. Thus, the compound recycled into step a) is said hydrofluoroalkane.

Step a) may be performed in the presence or absence of a catalyst.

According to a particular embodiment, the catalyst is chosen from alkali metal or alkaline-earth metal salts or a mixture thereof. The alkali metal or alkaline-earth metal is preferably chosen from Li, Na, K, Cs, Mg and Ca. The anion associated with the metal is $F^-$, $Cl^-$, $I^-$ or $CO_3^{2-}$. Preferably, the catalyst is NaI or KI. The catalyst preferably has a specific surface area of between 20 and 1000 $m^2/g$, in particular between 20 and 300 $m^2/g$. The catalyst content is from 1% to 30% by weight relative to said hydrofluoroalkane. The above catalysts are preferred for liquid-phase reactions.

According to another particular embodiment, the catalyst may be chosen from the group consisting of an oxide, oxyhalide or halide of a metal or metalloid from columns 4 to 15 of the Periodic Table. The catalyst may be an oxide, oxyhalide or halide of chromium or aluminum; in particular, the halide is a fluoride. More particularly, the catalyst may be a chromium fluoride, a chromium oxyfluoride or a chromium oxide. The chromium or aluminum oxyfluoride preferably has a fluorine content of from 10% to 50% by weight, preferably from 20% to 50% by weight, in particular from 30% to 50% by weight. The fluorine content is measured ionometrically or by weight change of the catalyst or by any other quantitative method known to those skilled in the art. The chromium oxyfluoride or chromium fluoride catalyst preferably has a specific surface area of from 15 to 100 $m^2/g$. The chromium oxide catalyst preferably has a specific surface area of from 100 to 300 $m^2/g$. The specific surface area is measured on a Micromeritics Gemini 2360 machine using the standard 5-point method (BET method). When the catalyst is a chromium oxide, chromium oxyfluoride or chromium fluoride, it may also contain from 0.5% to 10% by weight of a cocatalyst relative to the total weight of the catalyst. Said cocatalyst is chosen from Cr, Ni, Zn, Ti, V, Zr, Mo, Ge, Sn, Pb and Mg. The catalyst content is preferably from 0.01% to 20%, in particular from 0.1% to 10% by weight relative to said hydrofluoroalkane. These catalysts are preferred for performing step a) in the gas phase.

According to another particular embodiment, the catalyst may be a catalyst based on antimony, iron, titanium or tin, for instance a catalyst based on antimony, iron, titanium or tin halide. The catalyst may thus be $SbCl_5$, $SbF_5$, $FeCl_3$, $TiCl_4$ or $SnCl_4$. The catalyst content is preferably from 0.01% to 50%, in particular from 0.1% to 30% by weight relative to said hydrofluoroalkane. These catalysts may be used in the liquid or gas phase.

Thus, the preferred catalysts for performing step a) are chosen from the group consisting of $SbCl_5$, $SbF_5$, $FeCl_3$, $TiCl_4$, $SnCl_4$, NaI, KI, $Cr_2O_3$, $Al_2O_3$, chromium oxyfluoride, aluminum oxyfluoride, chromium fluoride and aluminum fluoride.

All of the catalysts mentioned above can be deposited on a porous support. The porous support may be chosen from activated charcoals, graphite, aluminas and alumina fluorides. When it is supported, the catalyst is present in a mass content of from 1% to 50% relative to the total weight of the catalyst and the support.

The catalyst may be activated prior to its use in step a) of the process. The activation preferably involves treating the catalyst with a stream of HF, $Cl_2$, $I_2$ or $O_2$ or a mixture thereof.

The catalyst may also deactivate over time. Thus, step a) may be performed in the presence of oxygen or air or an oxygen-nitrogen mixture. If oxygen is used in step a), it is present in a content of from 0.005 mol % to 10 mol % relative to the molar amount of hydrofluoroalkane.

The catalyst may also be regenerated after the present process has been performed. The regeneration step may comprise placing the catalyst in contact with a stream of oxygen or air at a temperature of from 200° C. to 700° C.

Step a) May be Performed in the Liquid Phase or in the Gas Phase.

When it is performed in the gas phase, step a) is also performed at a temperature of from 250° C. to 700° C., preferably from 300° C. to 600° C.

When it is performed in the liquid phase, step a) is also performed at a temperature of from 50° C. to 300° C., preferably from 50° C. to 280° C.

In addition, when it is performed in the liquid phase, step a) is also performed in the presence of a polar aprotic solvent S1. Preferably, the solvent S1 is anhydrous. The term "anhydrous" refers here to a solvent S1 containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said solvent S1 is free of water. The solvent S1 has a boiling point of from 0° C. to 250° C., preferably from 20° C. to 250° C., in particular from 20° C. to 200° C. Said solvent S1 is chosen from the group consisting of acetic acid, $CCl_4$, chloroform, dichloromethane, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof.

Step b) of the Process

Said stream A is then separated to form a first stream B1 comprising said iodofluoroalkane compound and a stream B2 comprising unreacted iodine. Both said stream B1 and said stream B2 may contain impurities, reaction by-products or even unreacted hydrofluoroalkane. Both said stream B1 and said stream B2 may optionally contain hydrogen iodide. Stream B1 is preferably subjected to an additional purification step to give a stream B1 comprising said purified iodofluoroalkane compound. Stream B2 may also be subjected to an additional purification step to separate any hydrogen iodide that may be present and the unreacted iodine. Preferably, after the separation and possible purification step, the content of said iodofluoroalkane compound in said stream B1 is greater than 90%, advantageously greater than 92%, preferably greater than 94%, more preferentially greater than 96%, in particular greater than 98%, more particularly greater than 99%.

Said stream A is preferably separated out and/or purified by distillation, azeotropic distillation, distillation under pressure, extractive distillation, cold separation, absorption in a solvent or a combination thereof.

Said stream A may also be separated out or purified by placing in contact with an adsorbent.

Said adsorbent may be a zeolite or a molecular sieve having a pore aperture with an average diameter of between 3 ångströms and 11 ångströms, advantageously between 4 ångströms and 10 ångströms, preferably between 5 ångströms and 10 ångströms.

Step c) of the Process

Step c) of the present process includes the recycling of stream B2 into step a). This recycling step improves the overall yield of the process (better conversion) and saves on expensive reagents (and catalysts), while at the same time minimizing the environmental impact. Without this recycling step, the unreacted iodine would have to be incinerated, thus increasing the carbon footprint of the process.

If stream B1 comprises unreacted hydrofluoroalkane, said reagent can be removed from stream B1 and can also be recycled into step a).

The present process can be performed continuously or in a batchwise or semi-batchwise manner.

Preferably, in order to avoid corrosion problems, the reactor, in which step a) is performed, is made of a material comprising a base layer made of a material M1 and an inner layer made of a material M2.

Advantageously, the material M2 comprises at least 40% by weight of nickel relative to the total weight of the material M2. Preferably, the material M2 comprises at least 45% by weight of nickel, more preferentially at least 50% by weight of nickel, in particular at least 55% by weight of nickel, more particularly at least 60% by weight of nickel, preferably at least 65% by weight of nickel, more preferably at least 70% by weight of nickel relative to the total weight of the material M2.

The material M2 may also comprise chromium in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

The material M2 may also comprise molybdenum in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

Preferably, the material M2 is Monel®, Hastelloy®, Inconel® or Incoloy®.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1. More particularly, the material M1 may comprise between 0.01% and 0.2% by weight of carbon on the basis of the total weight of the material M1.

Preferably, said base layer and said inner layer are placed against each other by hot or cold plating, hot or cold rolling or welding.

EXAMPLES

Example 1

The equipment used is composed of a Hastelloy C276 autoclave with a volume of 500 ml, equipped with a stirrer, a heating device and a temperature-regulating system. The autoclave is degassed and rendered inert with nitrogen, and the following anhydrous constituents are successively introduced: 250 mL of sulfolane, 15.0 g (0.1 mol) of sodium iodide, 67.0 g (0.5 mol) of $CF_3—CH_2—CHF_2$ (HFC-245fa) and 200.0 g (0.79 mol) of anhydrous $I_2$. The reaction medium is brought to 170-180° C. with stirring. After 6 hours of reaction with stirring, a sample is taken, washed and dried and then analyzed by gas chromatography (area percentage). The conversion of $CF_3—CH_2—CHF_2$ is 88% for a selectivity towards $CF_3—CH_2—CF_2I$ of 92%. Small amounts of $CF_3—CHI—CHF_2$, $CF_3—CI_2—CHF_2$ and $CF_3—CHI—CF_2I$ are observed.

Example 2

A reactor consisting of an Inconel 600 tube with an inside diameter of 28 mm and a length of 640 mm, placed vertically in a tubular furnace, is used. The catalytic bed consists of a lower 40 mm layer of corundum, followed by an 85 mm layer of chromium oxyfluoride catalyst containing between 15% and 25% by weight of fluorine. The catalyst was preactivated in the presence of a gaseous stream of $O_2$ at a temperature of 350° C. A gaseous stream of $CF_3—CHF—CH_2F$ (HFC-245eb) and a gaseous stream of anhydrous $I_2$ ($CF_3—CHF—CH_2F/I_2$ mole ratio=1/2) are passed over this catalyst at a temperature of 550° C. At the reactor outlet, the gases are washed and then dried and condensed in a cold trap. A sample is taken and analyzed by gas chromatography (area percentage). The conversion of $CF_3—CHF—CH_2F$ (HFC-245eb) is 94% for a selectivity towards $CF_3—CHF—CHFI$ of 98%. Small amounts of $CF_3—CFI—CH_2F$, $CF_3—CHF—CH_2$ and $CF_3—CFI—CHFI$ are observed. Equivalent conversion and selectivity values are obtained for the conversion of $CF_3—CHF—CH_3$ into $CF_3—CFI—CH_3$, of $CF_3—CH_2—CH_2F$ into $CF_3—CH_2—CHFI$ and of $CF_3—CHF—CHF_2$ into $CF_3—CHF—CF_2I$.

Invention IV

Summary of Invention IV

According to a first aspect, the invention relates to a process for producing an iodofluoroolefin compound, comprising the steps of:

a) placing a fluoroolefin of formula (I) $(R^1)(R^2)C=CH(R^3)$ in contact with iodine ($I_2$) in the liquid phase, to form a diiodofluoroalkane compound of formula (II) $(R^1)(R^2)C(I)—CH(I)(R^3)$;

b) dehydroiodination of said diiodofluoroalkane compound of formula (II) obtained in step a) to form a stream B comprising said iodofluoroolefin of formula (III) $(R^1)(R^2)C=C(I)(R^3)$; the substituents $R^1$, $R^2$ and $R^3$ being, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

According to a preferred embodiment, $R^1$, $R^2$ and $R^3$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; on condition that $R^1$, $R^2$ and $R^3$ are not simultaneously H.

According to a preferred embodiment, $R^1$, $R^2$ and $R^3$ are, independently of each other, chosen from the group consisting of H, F or $Y^1—[—C(Y^2)(Y^3)—]_n—$ in which $Y^1$, $Y^2$ and $Y^3$ are, independently of each other and independently for each unit n, chosen from the group consisting of H and F; and n is an integer from 1 to 10; provided that at least one of the substituents $R^1$, $R^2$, $R^3$, $Y^1$, $Y^2$ or $Y^3$ is F.

According to a preferred embodiment, said fluoroolefin is chosen from the group consisting of $CHF=CH_2$, $CF_2=CH_2$, $CHF=CHF$, $CF_2=CHF$, $CH_3—CF=CH_2$, $CH_3—CH=CHF$, $CH_2F—CH=CH_2$, $CH_3—CF=CHF$, $CH_2F—CF=CH_2$, $CH_3—CH=CF_2$, $CH_2F—CH=CHF$, $CHF_2—CH=CH_2$, $CH_3—CF=CF_2$, $CH_2F—CF=CHF$, $CHF_2—CF=CH_2$, $CH_2F—CH=CF_2$, $CHF_2—CH=CHF$, $CF_3—CH=CH_2$, $CH_2F—CF=CF_2$, $CHF_2CF=CHF$, $CF_3—CF=CH_2$, $CHF_2—CH=CF_2$, $CF_3—CH=CHF$, $CHF_2—CF=CF_2$, $CF_3CF=CHF$, $CF_3—CH=CF_2$; advantageously, said fluoroolefin is chosen from the group consisting of $CF_2=CH_2$, $CF_2=CHF$, $CF_3—CH=CH_2$, $CF_3CF=CH_2$, $CF_3—CH=CHF$, $CF_3—CF=CHF$;

and said diiodofluoroalkane compound is chosen from the group consisting of $CHFI—CH_2I$, $CF_2I—CH_2I$, $CHFI—CHFI$, $CF_2I—CHFI$, $CH_3—CFI—CH_2I$, $CH_3—CHI—CHFI$, $CH_2F—CHI—CH_2I$, $CH_3CFI—CHFI$, $CH_2F—CFI—CH_2I$, $CH_3—CHI—CF_2I$, $CH_2F—CHI—CHFI$, $CHF_2—CHI—CH_2I$, $CH_3—CFI—CF_2I$, $CH_2F—CFI—CHFI$, $CHF_2—CFI—CH_2I$, $CH_2F—CHI—CF_2I$, $CHF_2CHI—CHFI$, $CF_3CHI—CH_2I$, $CH_2F—CFI—CF_2I$, $CHF_2—CFI—CHFI$, $CF_3—CFI—CH_2I$, $CH\ F_2—CHI—CF_2I$, $CF_3—CHI—CHFI$, $CHF_2—CFI—CF_2I$, $CF_3CFI—CHFI$, $CF_3CHI—CF_2I$; advantageously, said diiodofluoroalkane compound is chosen from the group consisting of $CF_2I—CH_2I$, $CF_2I—CHFI$, $CF_3CHI—CH_2I$, $CF_3CFI—CH_2I$, $CF_3CHI—CHFI$, $CF_3CFI—CHFI$;

and said iodofluoroolefin is chosen from the group consisting of $CFI=CH_2$, $CHF=CHI$, $CF_2=CHI$, $CFI=CHF$, $CF_2=CFI$, $CH_2=CF—CH_2I$, $CH_3—CF=CHI$, $CH_2=CH—CHFI$, $CH_3CI=CHF$, $CH_3—CH=CFI$, $CHF=CH—CH_2I$, $CH_2F—CI=CH_2$, $CH_2F—CH=CHI$, $CH_2=CF—CHFI$, $CH_3—CF=CFI$, $CHF=CF—CH_2I$, $CH_2F—CF=CHI$, $CH_2=CH—CF_2I$, $CH_3CI=CF_2$, $CHF=CH—CHFI$, $CH_2F—CI=CHF$, $CH_2F—CH=CFI$, $CF_2=CH—CH_2I$, $CHF_2—CI=CH_2$, $CHF_2CH=CHI$, $CH_2=CF—CF_2I$, $CHF=CF—CHFI$, $CH_2F—CF=CFI$, $CF_2=CF—CH_2I$, $CHF_2—CF=CHI$, $CHF=CH—CF_2I$, $CH_2F—CI=CF_2$, $CF_2=CH—CHFI$, $CHF_2—CI=CHF$, $CHF_2—CH=CFI$, $CF_3—CI=CH_2$, $CF_3—CH=CHI$, $CHF=CF—CF_2I$, $CF_2=CF—CHFI$, $CHF_2—CF=CFI$, $CF_3—CF=CHI$, $CF_2=CH—CF_2I$, $CHF_2—CI=CF_2$, $CF_3—CI=CHF$, $CF_3—CH=CFI$, $CF_2=CF—CF_2I$, $CF_3—CF=CFI$, $CF_3—CI=CF_2$; preferably, said iodofluoroolefin is chosen from the group consisting of $CHI=CHF$, $CF_2=CHI$, $CFI=CHF$, $CF_2=CFI$, $CH_3—CF=CHI$, $CH_3—CI=CHF$, $CH_2F—CI=CH_2$, $CH_2=CF—CHFI$, $CH_2F—CF=CHI$, $CH_3—CI=CF_2$, $CH_2F—CI=CHF$, $CHF_2—CI=CH_2$, $CH_2=CF—CF_2I$, $CHF=CF—CHFI$, $CHF_2—CF=CHI$, $CH_2F—CI=CF_2$, $CHF_2—CI=CHF$, $CF_3—CI=CH_2$, $CHF=CF—CF_2I$, $CHF_2—CF=CFI$, $CF_3—CF=CHI$, $CHF_2CI{=}CF_2$, $CF_3{-}CI{=}CHF$, $CF_2{=}CF{-}CF_2I$, $CF_3{-}CF{=}CFI$, $CF_3{-}CI{=}CF_2$; in particular, said iodofluoroolefin is chosen from the group consisting of $CF_2{=}CHI$, $CF_2{=}CFI$, $CF_3{-}CI{=}CH_2$, $CF_3{-}CF{=}CHI$, $CF_3{-}CI{=}CHF$, $CF_3CF{=}CFI$.

According to a preferred embodiment, stream B also comprises HI, and the process comprises a step of separation between said iodofluoroolefin and HI.

According to a preferred embodiment, said diiodofluoroalkane compound is dried and optionally purified before being used in step b).

According to a preferred embodiment, step a) is performed in the liquid phase in the presence of a solvent chosen from the group consisting of aqueous potassium iodide solutions, ethers, fluorinated ethers, alcohols, fluorinated alcohols, esters, aromatic solvents, fluorinated aromatic solvents, halogenated solvents and mixtures thereof.

According to a preferred embodiment, step b) is performed using a basic aqueous mixture; advantageously, said mixture comprises a base chosen from an alkali metal or alkaline-earth metal hydroxide; preferably, said mixture has an alkali metal or alkaline-earth metal hydroxide content of from 20% to 80% by weight relative to the total weight of said mixture.

According to a preferred embodiment, step b) is performed in the gas phase and said dehydroiodination catalyst is chosen from the group consisting of an oxide, oxyhalide or halide of a metal or metalloid from columns 4 to 15 of the Periodic Table, preferably chosen from the group consisting of an aluminum, iron or chromium oxide, oxyhalide or halide.

According to a second aspect, the present invention provides a process for producing said diiodofluoroalkane compound, comprising step a) of placing a fluoroolefin of formula (I) $(R^1)(R^2)C{=}CH(R^3)$ in contact with iodine ($I_2$) in the liquid phase, to form a diiodofluoroalkane compound of formula (II) $(R^1)(R^2)C(I){-}CH(I)(R^3)$; in which $R^1$, $R^2$ and $R^3$ are as defined above According to a preferred embodiment, said diiodofluoroalkane compound is chosen from the group consisting of $CHFI{-}CH_2I$, $CF_2I{-}CH_2I$, $CHFI{-}CHFI$, $CF_2I{-}CHFI$, $CH_3{-}CFI{-}CH_2I$, $CH_3{-}CHI{-}CHFI$, $CH_2F{-}CHI{-}CH_2I$, $CH_3{-}CFI{-}CHFI$, $CH_2F{-}CFI{-}CH_2I$, $CH_3{-}CHI{-}CF_2I$, $CH_2F{-}CHI{-}CHFI$, $CHF_2{-}CHI{-}CH_2I$, $CH_3{-}CFI{-}CF_2I$, $CH_2F{-}CFI{-}CHFI$, $CHF_2{-}CFI{-}CH_2I$, $CH_2F{-}CHI{-}CF_2I$, $CHF_2{-}CHI{-}CHFI$, $CF_3{-}CHI{-}CH_2I$, $CH_2F{-}CFI{-}CF_2I$, $CHF_2{-}CFI{-}CHFI$, $CF_3{-}CFI{-}CH_2I$, $CHF_2{-}CHI{-}CF_2I$, $CF_3{-}CHI{-}CHFI$, $CHF_2{-}CFI{-}CF_2I$, $CF_3{-}CFI{-}CHFI$, $CF_3{-}CHI{-}CF_2I$; advantageously, said iodofluoroalkane compound is chosen from the group consisting of $CF_2I{-}CH_2I$, $CF_2I{-}CHFI$, $CF_3{-}CHI{-}CH_2I$, $CF_3{-}CFI{-}CH_2I$, $CF_3{-}CHI{-}CHFI$, $CF_3{-}CF_1{-}CHFI$.

According to a preferred embodiment, said diiodofluoroalkane compound is isolated and purified.

Detailed Description of the Present Invention

According to a first aspect, the invention relates to a process for producing an iodofluoroolefin compound. Preferably, said process comprises at least one step of placing a fluoroolefin of formula (I) $(R^1)(R^2)C{=}CH(R^3)$ in contact with iodine ($I_2$) in the liquid phase, to form a diiodofluoroalkane compound of formula (II) $(R^1)(R^2)C(I){-}CH(I)(R^3)$. Preferably, said process also comprises a step of dehydroiodination of said diiodofluoroalkane compound of formula (II) obtained in step a) to form a stream B comprising said iodofluoroolefin of formula (III) $(R^1)(R^2)C{=}C(I)(R^3)$. The substituents $R^1$, $R^2$ and $R^3$ are as defined below.

Thus, said process comprises the steps of:

a) placing a fluoroolefin of formula (I) $(R^1)(R^2)C{=}CH(R^3)$ in contact with iodine ($I_2$) in the liquid phase, to form a diiodofluoroalkane compound of formula (II) $(R^1)(R^2)C(I){-}CH(I)(R^3)$;

b) dehydroiodination of said diiodofluoroalkane compound of formula (II) obtained in step a) to form a stream B comprising said iodofluoroolefin of formula (III) $(R^1)(R^2)C{=}C(I)(R^3)$; the substituents $R^1$, $R^2$ and $R^3$ being, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

Step a) of the Process

Step a) of the present process requires a fluoroolefin to be placed in contact with iodine ($I_2$) in the liquid phase.

Said fluoroolefin is preferably of formula (I) $(R^1)(R^2)C{=}CH(R^3)$ in which $R^1$, $R^2$ and $R^3$ are, independently of each other, chosen from the group consisting of H, F, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

Said fluoroolefin is preferably of formula (I) $(R^1)(R^2)C{=}CH(R^3)$ in which $R^1$, $R^2$ and $R^3$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

The term "alkyl" denotes a monovalent radical resulting from a linear or branched alkane comprising the number of carbon atoms specified. The term "cycloalkyl" denotes a monovalent radical resulting from a cycloalkane comprising the number of carbon atoms specified. The term "alkenyl" denotes a monovalent radical comprising the number of carbon atoms specified and at least one carbon-carbon double bond. The term "cycloalkenyl" refers to a monovalent radical resulting from a cycloalkene comprising the number of carbon atoms specified and at least one carbon-carbon double bond in its cyclic part. The term "aryl" denotes a monovalent radical resulting from an arene comprising the number of carbon atoms specified.

Preferably, said alkyl, cycloalkyl, alkenyl, cycloalkenyl or aryl radical is not substituted with functional groups other than fluorine. Said radical may nevertheless comprise several fluorine atoms on its carbon chain, for example, said radical may contain from 1 to 10 fluorine atoms, preferably from 1 to 5 fluorine atoms.

Preferably, said fluoroolefin is of formula (I) $(R^1)(R^2)C{=}CH(R^3)$ in which $R^1$, $R^2$ and $R^3$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said fluoroolefin is of formula (I) $(R^1)(R^2)C{=}CH(R^3)$ in which $R^1$, $R^2$ and $R^3$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said fluoroolefin is of formula (I) $(R^1)(R^2)C{=}CH(R^3)$ in which $R^1$, $R^2$ and $R^3$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$—$C_{10}$ aryl radical optionally substituted with 1 to 5 fluorine atoms; provided that at least one of the substituents $R^1$, $R^2$ or $R^3$ is F or is a radical as defined above including from 1 to 5 fluorine atoms.

Preferably, said fluoroolefin is of formula (I) $(R^1)(R^2)C{=}CH(R^3)$ in which $R^1$, $R^2$ and $R^3$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; with the proviso that at least one of the substituents $R^1$, $R^2$ or $R^3$ is F or is a radical as defined above including from 1 to 5 fluorine atoms.

Preferably, said fluoroolefin is of formula (I) $(R^1)(R^2)C{=}CH(R^3)$ in which $R^1$, $R^2$ and $R^3$ are, independently of each other, chosen from the group consisting of H, F, I, a $C_1$-$C_{10}$ perfluoroalkyl radical, a $C_3$-$C_{30}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said fluoroolefin is of formula (I) $(R^1)(R^2)C{=}CH(R^3)$ in which $R^1$, $R^2$ and $R^3$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said fluoroolefin is of formula (I) $(R^1)(R^2)C{=}CH(R^3)$ in which $R^1$, $R^2$ and $R^3$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said fluoroolefin is of formula (I) $(R^1)(R^2)C{=}CH(R^3)$ in which $R^1$, $R^2$ and $R^3$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Alternatively, said fluoroolefin is of formula (I) $(R^1)(R^2)C{=}CH(R^3)$ in which $R^1$, $R^2$ and $R^3$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $Y^1$, $Y^2$ or $Y^3$ is F.

Preferably, said fluoroolefin is of formula (I) $(R^1)(R^2)C{=}CH(R^3)$ in which $R^1$, $R^2$ and $R^3$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $Y^1$, $Y^2$ or $Y^3$ is F.

Preferably, said fluoroolefin is of formula (I) $(R^1)(R^2)C{=}CH(R^3)$ in which $R^1$, $R^2$ and $R^3$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 10; provided that at least one of the substituents $R^1$, $R^2$, $R^3$, $Y^1$, $Y^2$ or $Y^3$ is F.

Preferably, said fluoroolefin is of formula (I) $(R^1)(R^2)C{=}CH(R^3)$ in which $R^1$, $R^2$ and $R^3$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $Y^1$, $Y^2$ or $Y^3$ is F.

According to a preferred embodiment, said fluoroolefin is chosen from the group consisting of $CHF{=}CH_2$, $CF_2{=}CH_2$, $CHF{=}CHF$, $CF_2{=}CHF$, $CH_3$—$CF{=}CH_2$, $CH_3$—$CH{=}CHF$, $CH_2F$—$CH{=}CH_2$, $CH_3$—$CF{=}CHF$, $CH_2F$—$CF{=}CH_2$, $CH_3$—$CH{=}CF_2$, $CH_2F$—$CH{=}CHF$, $CHF_2$—$CH{=}CH_2$, $CH_3$—$CF{=}CF_2$, $CH_2F$—$CF{=}CHF$, $CHF_2$—$CF{=}CH_2$, $CH_2F$—$CH{=}CF_2$, $CHF_2$—$CH{=}CHF$, $CF_3$—$CH{=}CH_2$, $CH_2F$—$CF{=}CF_2$, $CHF_2$—$CF{=}CHF$, $CF_3$—$CF{=}CH_2$, $CHF_2$—$CH{=}CF_2$, $CF_3$—$CH{=}CHF$, $CHF_2$—$CF{=}CF_2$, $CF_3$—$CF{=}CHF$, $CF_3$—$CH{=}CF_2$. Advantageously, said fluoroolefin is chosen from the group consisting of $CF_2{=}CH_2$, $CF_2{=}CHF$, $CF_3$—$CH{=}CH_2$, $CF_3$—$CF{=}CH_2$, $CF_3$—$CH{=}CHF$, $CF_3$—$CF{=}CHF$.

Said fluoroolefin may have a boiling point of less than 100° C. at atmospheric pressure. Advantageously, said fluoroolefin has a boiling point of less than 75° C. at atmospheric pressure. Preferably, said fluoroolefin has a boiling point of less than 50° C. at atmospheric pressure. More preferentially, said fluoroolefin has a boiling point of less than 25° C. at atmospheric pressure. In particular, said fluoroolefin has a boiling point of less than 10° C. at atmospheric pressure.

According to a preferred embodiment, step a) may be performed in the presence of a mixture of fluoroolefins to result in the coproduction of iodofluoroolefins via the corresponding diiodofluoroalkane compounds in accordance with the present process.

Step a) allows the formation of a diiodofluoroalkane compound of formula (II) $(R^1)(R^2)C(I)—CH(I)(R^3)$ in which $R^1$, $R^2$ and $R^3$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; with the proviso that at least one of the substituents $R^1$, $R^2$ or $R^3$ is F or is a radical as defined above including from 1 to 5 fluorine atoms.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; with the proviso that at least one of the substituents $R^1$, $R^2$ or $R^3$ is F or is a radical as defined above including from 1 to 5 fluorine atoms.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, I, a $C_1$-$C_{10}$ perfluoroalkyl radical, a $C_5$-$C_{10}$ perfluorocycloalkyl radical, a $C_2$-$C_{10}$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Alternatively, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $Y^1$, $Y^2$ or $Y^3$ is F.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $Y^1$, $Y^2$ or $Y^3$ is F.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F or $Y^1—[—C(Y^2)(Y^3)—]_n—$ in which $Y^1$, $Y^2$ and $Y^3$ are, independently of each other and independently for each unit n, chosen from the group consisting of H and F; and n is an integer from 1 to 10; provided that at least one of the substituents $R^1$, $R^2$, $R^3$, $Y^1$, $Y^2$ or $Y^3$ is F.

Preferably, said diiodofluoroalkane compound is of formula (II) $(R^1)(R^2)C(I)—CH(I)(R^3)$ in which $R^1$, $R^2$ and $R^3$ are, independently of each other, chosen from the group consisting of H, F or $Y^1—[—C(Y^2)(Y^3)—]_n—$ in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $Y^1$, $Y^2$ or $Y^3$ is F.

In particular, said diiodofluoroalkane compound is chosen from the group consisting of $CHFI—CH_2I$, $CF_2I—CH_2I$, $CHFI—CHFI$, $CF_2I—CHFI$, $CH_3—CFI—CH_2I$, $CH_3—CHI—CHFI$, $CH_2F—CHI—CH_2I$, $CH_3—CFI—CHFI$, $CH_2F—CFI—CH_2I$, $CH_3—CHI—CF_2I$, $CH_2F—CHI—CHFI$, $CHF_2—CHI—CH_2I$, $CH_3—CFI—CF_2I$, $CH_2F—CFI—CHFI$, $CHF_2—CFI—CH_2I$, $CH_2F—CHI—CF_2I$, $CHF_2—CHI—CHFI$, $CF_3—CHI—CH_2I$, $CH_2F—CFI—CF_2I$, $CHF_2—CFI—CHFI$, $CF_3—CFI—CH_2I$, $CHF_2—CHI—CF_2I$, $CF_3—CHI—CHFI$, $CHF_2—CFI—CF_2I$, $CF_3—CFI—CHFI$, $CF_3—CHI—CF_2I$. More particularly, said diiodofluoroalkane compound is chosen from the group consisting of $CF_2I—CH_2I$, $CF_2I—CHFI$, $CF_3—CHI—CH_2I$, $CF_3—CFI—CH_2I$, $CF_3—CHI—CHFI$, $CF_3—CFI—CHFI$.

Preferably, step a) allows at least one of the following reactions:

converting $CHF{=}CH_2$ into $CHFI—CH_2I$; or
converting $CF_2{=}CH_2$ into $CF_2I—CH_2I$; or
converting $CHF{=}CHF$ into $CHFI—CHFI$; or
converting $CF_2{=}CHF$ into $CF_2I—CHFI$; or
converting $CH_3—CF{=}CH_2$ into $CH_3—CFI—CH_2I$; or
converting $CH_3—CH{=}CHF$ into $CH_3—CHI—CHFI$; or
converting $CH_2F—CH{=}CH_2$ into $CH_2F—CHI—CH_2I$; or
converting $CH_3—CF{=}CHF$ into $CH_3—CFI—CHFI$; or
converting $CH_2F—CF{=}CH_2$ into $CH_2F—CFI—CH_2I$; or
converting $CH_3—CH{=}CF_2$ into $CH_3—CHI—CF_2I$; or
converting $CH_2F—CH{=}CHF$ into $CH_2F—CHI—CHFI$; or
converting $CHF_2—CH{=}CH_2$ into $CHF_2—CHI—CH_2I$; or
converting $CH_3—CF{=}CF_2$ into $CH_3—CFI—CF_2I$; or
converting $CH_2F—CF{=}CHF$ into $CH_2F—CFI—CHFI$; or
converting $CHF_2—CF{=}CH_2$ into $CHF_2—CFI—CH_2I$; or
converting $CH_2F—CH{=}CF_2$ into $CH_2F—CHI—CF_2I$; or
converting $CHF_2—CH{=}CHF$ into $CHF_2—CHI—CHFI$; or
converting $CF_3—CH{=}CH_2$ into $CF_3—CHI—CH_2I$; or
converting $CH_2F—CF{=}CF_2$ into $CH_2F—CFI—CF_2I$; or
converting $CHF_2—CF{=}CHF$ into $CHF_2—CFI—CHFI$; or
converting $CF_3—CF{=}CH_2$ into $CF_3—CFI—CH_2I$; or
converting $CHF_2—CH{=}CF_2$ into $CHF_2—CHI—CF_2I$; or
converting $CF_3—CH{=}CHF$ into $CF_2—CHI—CHFI$;
converting $CHF_2—CF{=}CF_2$ into $CHF_2—CFI—CF_2I$; or
converting $CF_3—CF{=}CHF$ into $CF_3—CFI—CHFI$; or
converting $CF_3—CH{=}CF_2$ into $CF_3—CHI—CF_2I$.

Preferably, step a) is performed in the absence of catalyst. Preferably, step a) is performed in the presence of a solvent S1. Preferably, the solvent S1 is chosen from the group consisting of aqueous potassium iodide solutions, ethers, fluorinated ethers, alcohols, fluorinated alcohols, esters, aromatic solvents, fluorinated aromatic solvents, halogenated solvents and mixtures thereof. Advantageously, the solvent S1 is chosen from the group consisting of aqueous potassium iodide solutions, ethyl and methyl ethers, hydrofluoroethers, ethyl and methyl alcohols, ethyl lactate, toluene, xylenes, para-chlorotrifluoromethylbenzene, hexafluorobenzene, tetrachloromethane, chloroform, dichloromethane, 1-bromopropane and mixtures thereof. The use of a solvent in the present process makes it possible to avoid the problems of clogging associated with the sublimation of iodine and also to limit the formation of impurities (reaction by-products, polymers derived from the fluoroolefin, etc.), which makes it possible to achieve selectivities that are particularly advantageous from an industrial viewpoint.

Preferably, the iodine is placed in contact with said fluoroolefin as defined above at the stoichiometry or in excess thereof. For example, the $I_2$/olefin mole ratio is from 0.1 to 50, preferably from 0.5 to 25, in particular from 1 to 20.

Preferably, the content of oxygen dissolved in the solvent S1 is less than 3000 ppm, advantageously less than 2000 ppm, preferably less than 1000 ppm, more preferentially less than 500 ppm, in particular less than 250 ppm, more particularly less than 100 ppm, preferably less than 50 ppm, preferentially preferably less than 10 ppm. This avoids the degradation of the starting materials and of the desired products. The solvent S1 preferably has a boiling point of from 0° C. to 250° C., preferably from 20° C. to 250° C., in particular from 20° C. to 200° C.

The temperature at which step a) is performed is from 20° C. to 280° C., preferably from 30° C. to 250° C. Step a) may be performed at a pressure of from 0.1 bar to 15 bar, preferably from 1 bara to 10 bara.

Said diiodofluoroalkane compound may be dried before being used in step b). This allows the removal of any traces of water that may be present. The drying may be performed by placing in contact with an adsorbent, an absorbent, a 3 to 5 ångström sieve or zeolites.

Said diiodofluoroalkane compound may be purified before being used in step b). The purification may be performed before or after the drying step. This allows the removal of certain impurities that may be difficult to separate from the iodofluoroolefin compound obtained in step b). This step also makes it possible to increase the selectivity of step b). The purification may be performed by distillation, azeotropic distillation, distillation under pressure, extractive distillation, cold separation, absorption in a solvent, or by placing in contact with an adsorbent or a combination thereof. Advantageously, the purification of the diiodofluoroalkane compound is directed toward producing a stream A in which the content of diiodofluoroalkane compound is greater than 90%, advantageously greater than 92%, preferably greater than 94%, more preferentially greater than 96%, in particular greater than 98%, more particularly greater than 99%. This stream A is then used in step b).

When step a) is performed using a mixture of fluoroolefins, the purification, if it is performed, affords a mixture of diiodofluoroalkane compounds or a particular diiodofluoroalkane compound depending on the conditions used for performing the purification.

Said dried diiodofluoroalkane compound may be purified as described above or used as such in step b). Said dried diiodofluoroalkane compound is used directly in step b) without being purified after the drying step, for example when step a) is performed with high conversion and selectivity, for example greater than 90%, preferably greater than 95%. The absence of purification between step a) and step b)

may be advantageous from the point of view of the overall productivity of the process, since a purification step may give rise to significant costs.

The diiodofluoroalkane compound used in step b) is preferably anhydrous, i.e. the stream containing the diiodofluoroalkane compound used in step b) is anhydrous. The term "anhydrous" refers here to a water content by mass in the stream containing said diiodofluoroalkane compound and used in step b) of less than 500 ppm of water, advantageously less than 250 ppm, preferably less than 100 ppm of water, more preferentially less than 50 ppm of water, in particular less than 25 ppm of water, more particularly less than 10 ppm, more preferably less than 5 ppm of water; preferentially preferably, said diiodofluoroalkane compound or the stream in which it is contained for performing step b) is free of water.

Step b) of the Process

Step b) of the present process is a step of dehydroiodination of said diiodofluoroalkane compound of formula (II) obtained in step a) to form a stream B comprising said iodofluoroolefin of formula (III) $(R^1)(R^2)C{=}C(I)(R^3)$.

Said iodofluoroolefin obtained in step b) is of formula (III) $(R^1)(R^2)C{=}C(I)(R^3)$ in which $R^1$, $R^2$ and $R^3$ are, independently of each other, chosen from the group consisting of H, F, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

Said iodofluoroolefin is preferably of formula (III) $(R^1)(R^2)C{=}C(I)(R^3)$ in which $R^1$, $R^2$ and $R^3$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$ or $R^3$ is F or is a radical as defined above including at least one fluorine atom.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$ or $R^3$ is F or is a radical as defined above including from 1 to 10 fluorine atoms.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; with the proviso that at least one of the substituents $R^1$, $R^2$ or $R^3$ is F or is a radical as defined above including from 1 to 5 fluorine atoms.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; with the proviso that at least one of the substituents $R^1$, $R^2$ or $R^3$ is F or is a radical as defined above including from 1 to 5 fluorine atoms.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_1$-$C_{10}$ perfluoroaryl radical; provided that at least one of the substituents $R^1$, $R^2$ or $R^3$ is F or is a perfluoro radical as defined above.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$ or $R^3$ is F or is a perfluoro radical as defined above.

Alternatively, said iodofluoroolefin is of formula (III) $(R^1)(R^2)C{=}C(I)(R^3)$ in which $R^1$, $R^2$ and $R^3$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $Y^1$, $Y^2$ or $Y^3$ is F.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, I, F or $Y^1$—[—$C(Y^2)(Y^3)$—]$_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $Y^1$, $Y^2$ or $Y^3$ is F.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 10; provided that at least one of the substituents $R^1$, $R^2$, $R^3$, $Y^1$, $Y^2$ or $Y^3$ is F.

Preferably, said iodofluoroolefin is of formula (III) $(R^1)(R^2)C{=}C(I)(R^3)$ in which $R^1$, $R^2$ and $R^3$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $Y^1$, $Y^2$ or $Y^3$ is F.

In particular, said iodofluoroolefin is chosen from the group consisting of $CFI{=}CH_2$, $CHF{=}CHI$, $CF_2{=}CHI$, $CFI{=}CHF$, $CF_2{=}CFI$, $CH_2{=}CF{-}CH_2I$, $CH_3{-}CF{=}CHI$, $CH_2{=}CH{-}CHFI$, $CH_3{-}CI{=}CHF$, $CH_3{-}CH{=}CFI$, $CHF{=}CH{-}CH_2I$, $CH_2F{-}CI{=}CH_2$, $CH_2F{-}CH{=}CHI$, $CH_2{=}CF{-}CHFI$, $CH_3{-}CF{=}CFI$, $CHF{=}CF{-}CH_2I$, $CH_2F{-}CF{=}CHI$, $CH_2{=}CH{-}CF_2I$, $CH_3{-}CI{=}CF_2$, $CHF{=}CH{-}CHFI$, $CH_2F{-}CI{=}CHF$, $CH_2F{-}CH{=}CFI$, $CF_2{=}CH{-}CH_2I$, $CHF_2{-}CI{=}CH_2$, $CHF_2{-}CH{=}CHI$, $CH_2{=}CF{-}CF_2I$, $CHF{=}CF{-}CHFI$, $CH_2F{-}CF{=}CFI$, $CF_2{=}CF{-}CH_2I$, $CHF_2{-}CF{=}CHI$, $CHF{=}CH{-}CF_2I$, $CH_2F{-}CI{=}CF_2$, $CF_2{=}CH{-}CHFI$, $CHF_2{-}CI{=}CHF$, $CHF_2{-}CH{=}CFI$, $CF_3{-}CI{=}CH_2$, $CF_3{-}CH{=}CHI$, $CHF{=}CF{-}CF_2I$, $CF_2{=}CF{-}CHFI$, $CHF_2{-}CF{=}CFI$, $CF_3{-}CF{=}CHI$, $CF_2{=}CH{-}CF_2I$, $CHF_2{-}CI{=}CF_2$, $CF_3{-}CI{=}CHF$, $CF_2{-}CH{=}CFI$, $CF_2{=}CF{-}CF_2I$, $CF_3{-}CF{=}CFI$, $CF_3{-}CI{=}CF_2$; preferably, said iodofluoroolefin is chosen from the group consisting of $CHI{=}CHF$, $CF_2{=}CHI$, $CFI{=}CHF$, $CF_2{=}CFI$, $CH_3{-}CF{=}CHI$, $CH_3{-}CI{=}CHF$, $CH_2F{-}CI{=}CH_2$, $CH_2{=}CF{-}CHFI$, $CH_2F{-}CF{=}CHI$, $CH_3{-}CI{=}CF_2$, $CH_2F{-}CI{=}CHF$, $CHF_2{-}CI{=}CH_2$, $CH_2{=}CF{-}CF_2I$, $CHF{=}CF{-}CHFI$, $CHF_2{-}CF{=}CHI$, $CH_2F{-}CI{=}CF_2$, $CHF_2{-}CI{=}CHF$, $CF_3{-}CI{=}CH_2$, $CHF{=}CF{-}CF_2I$, $CHF_2{-}CF{=}CFI$, $CF_3{-}CF{=}CHI$, $CHF_2{-}CI{=}CF_2$, $CF_3{-}CI{=}CHF$, $CF_2{=}CF{-}CF_2I$, $CF_3{-}CF{=}CFI$, $CF_3{-}CI{=}CF_2$; in particular, said iodofluoroolefin is chosen from the group consisting of $CF_2{=}CHI$, $CF_2{=}CFI$, $CF_3{-}CI{=}CH_2$, $CF_3{-}CF{=}CHI$, $CF_3{-}CI{=}CHF$, $CF_3{-}CF{=}CFI$.

Preferably, step b) allows at least one of the following reactions:

converting $CHFI{-}CH_2I$ into $CHI{=}CHF$;
converting $CF_2I{-}CH_2I$ into $CF_2{=}CHI$;
converting $CHFI{-}CHFI$ into $CFI{=}CHF$;
converting $CF_2I{-}CHFI$ into $CF_2{=}CFI$;
converting $CH_3{-}CFI{-}CH_2I$ into $CH_3{-}CF{=}CHI$;
converting $CH_3{-}CHI{-}CHFI$ into $CH_3{-}CI{=}CHF$;
converting $CH_2F{-}CHI{-}CH_2I$ into $CH_2F{-}CI{=}CH_2$;
converting $CH_3{-}CFI{-}CHFI$ into $CH_2{=}CF{-}CHFI$;
converting $CH_2F{-}CFI{-}CH_2I$ into $CH_2F{-}CF{=}CHI$;
converting $CH_3{-}CHI{-}CF_2I$ into $CH_3{-}CI{=}CF_2$;
converting $CH_2F{-}CHI{-}CHFI$ into $CH_2F{-}CI{=}CHF$;
converting $CHF_2{-}CHI{-}CH_2I$ into $CHF_2{-}CI{=}CH_2$;
converting $CH_3{-}CFI{-}CF_2I$ into $CH_2{=}CF{-}CF_2I$;
converting $CH_2F{-}CFI{-}CHFI$ into $CHF{=}CF{-}CHFI$;
converting $CHF_2{-}CFI{-}CH_2I$ into $CHF_2{-}CF{=}CHI$;
converting $CH_2F{-}CHI{-}CF_2I$ into $CH_2F{-}CI{=}CF_2$;
converting $CHF_2{-}CHI{-}CHFI$ into $CHF_2{-}CI{=}CHF$;
converting $CF_3{-}CHI{-}CH_2I$ into $CF_3{-}CI{=}CH_2$;
converting $CH_2F{-}CFI{-}CF_2I$ into $CHF{=}CF{-}CF_2I$;
converting $CHF_2{-}CFI{-}CHFI$ into $CHF_2{-}CF{=}CFI$;
converting $CF_3{-}CFI{-}CH_2I$ into $CF_3{-}CF{=}CHI$;
converting $CHF_2{-}CHI{-}CF_2I$ into $CHF_2{-}CI{=}CF_2$;
converting $CF_3{-}CHI{-}CHFI$ into $CF_3{-}CI{=}CHF$;
converting $CHF_2{-}CFI{-}CF_2I$ into $CF_2{=}CF{-}CF_2I$;
converting $CF_3{-}CFI{-}CHFI$ into $CF_3{-}CF{=}CFI$;
converting $CF_3{-}CHI{-}CF_2I$ into $CF_3{-}CI{=}CF_2$.

Gas Phase Step b)

Step b) May be Performed in the Gas Phase.

Step b) may be performed in the gas phase and in the presence or absence of a catalyst.

Preferably, the dehydroiodination catalyst is chosen from the group consisting of an oxide, oxyhalide or halide of a metal or metalloid from columns 4 to 15 of the Periodic Table or of a metal chosen from U, Na, K, Cs, Mg, Ca, Al and Sb.

In particular, the dehydroiodination catalyst is chosen from the group consisting of an aluminum, iron or chromium oxide, oxyhalide or halide. Preferably, the catalyst is a chromium oxide, chromium oxyfluoride or a chromium fluoride. The chromium oxyfluoride preferably has a fluorine content of from 10% to 50% by weight, preferably from 20% to 50% by weight, in particular from 30% to 50% by weight. The fluorine content is measured ionometrically or by weight change of the catalyst or by any other quantitative method known to those skilled in the art. The chromium oxyfluoride or chromium fluoride catalyst preferably has a specific surface area of from 15 to 100 $m^2/g$. The chromium oxide catalyst preferably has a specific surface area of from 100 to 300 $m^2/g$. The specific surface area is measured on a Micromeritics Gemini 2360 machine using the standard 5-point method (BET method). When the catalyst is a chromium oxide, chromium oxyfluoride or chromium fluoride, it may also contain from 0.5% to 10% by weight of a cocatalyst relative to the total weight of the catalyst. Said cocatalyst is chosen from Cr, Ni, Zn, Ti, V, Zr, Mo, Ge, Sn, Pb and Mg.

When the catalyst is chosen from the group consisting of an oxide, oxyhalide or halide of a metal or metalloid from columns 4 to 15 of the Periodic Table, it may be activated prior to its use in step b). For example, said catalyst may be activated in the presence of oxygen, air, hydrogen iodide or HF or a mixture thereof. The catalyst may also be regenerated after the present process has been performed. The regeneration step may comprise placing the catalyst in contact with a stream of oxygen or air at a temperature of from 200° C. to 700° C. The catalyst may also deactivate over time. Thus, step b) may be performed in the presence of oxygen or air or an oxygen-nitrogen mixture. If oxygen is used in step b), it is present in an amount of from 0.005 mol % to 10 mol % relative to the molar amount of fluoroolefin.

When the metal is chosen from U, Na, K, Cs, Mg, Ca, Al and Sb, the anion associated with the metal is $F^-$, $Cl^-$, $I^-$ or $CO_3^{2-}$. Preferably, the catalyst is NaI, KI, $SbF_5$, $AlF_3$ or $SbCl_5$. The catalyst preferably has a specific surface area of between 20 and 1000 $m^2/g$, in particular between 20 and 300 $m^2/g$. When the metal of the catalyst is chosen from U, Na, K, Cs, Mg, Ca, Al and Sb, the catalyst content is from 1% to 30% by weight relative to said fluoroolefin.

The catalyst may be deposited onto a porous support. The porous support may be chosen from activated charcoals, graphite, aluminas and alumina fluorides.

According to a preferred embodiment, in the gas phase, in the presence or absence of a catalyst, step b) is performed at a pressure of from 1 bar absolute to 20 bar absolute, preferably from 3 to 15 bar absolute.

According to a preferred embodiment, in the gas phase, in the presence or absence of a catalyst, step b) is performed at a temperature of from 150° C. to 700° C., preferably from 250° C. to 600° C.

According to a preferred embodiment, stream B also comprises HI. Said process thus comprises a step of separation between said iodofluoroolefin and HI.

Step b) in Nonaqueous Liquid Phase

Step b) may be performed in the nonaqueous liquid phase in the presence or absence of a catalyst. Preferably, step b) is performed in the nonaqueous liquid phase and in the presence of a solvent S2. Preferably, the solvent S2 is anhydrous. The term "anhydrous" refers here to a solvent S2 containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said solvent S2 is free of water. The solvent S2 has a boiling point of from 0° C. to 250° C., preferably from 20° C. to 250° C., in particular from 20° C. to 200° C. Said solvent S2 is chosen from the group consisting of acetic acid, $CCl_4$, chloroform, dichloromethane, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof.

Preferably, step b), in the nonaqueous liquid phase, is performed in the presence of a catalyst chosen from alkali metal or alkaline-earth metal salts. Preferably, the catalyst is an alkali metal salt. Any alkali metal iodide may be used, but sodium iodide or potassium iodide is preferably used. The ratio between the catalyst and said fluoroolefin is between 1 and 20, preferably between 1 and 10. The catalyst preferably has a specific surface area of between 20 and 1000 $m^2/g$, in particular between 20 and 300 $m^2/g$. The catalyst may be deposited onto a porous support. The porous support may be chosen from activated charcoals, graphite, aluminas and alumina fluorides.

The temperature at which step b) is performed in the nonaqueous liquid phase is from 50° C. to 280° C., preferably from 50° C. to 250° C.

According to a preferred embodiment, stream B also comprises HI. Said process thus comprises a step of separation between said iodofluoroolefin and HI.

Aqueous Phase Step b)

Step b) may be performed using a basic aqueous mixture. The basic aqueous mixture is a liquid (for example a solution, dispersion, emulsion or suspension) with a pH of at least 7, advantageously at least 8, preferably at least 10. A pH of at least 10 favors the dehydroiodination reaction. The basic aqueous mixture comprises a base chosen from the group consisting of alkali metal or alkaline-earth metal hydroxide, oxide, carbonate or phosphate salts. Preferably, the base is chosen from lithium hydroxide, sodium hydroxide, potassium hydroxide, calcium hydroxide, magnesium oxide, calcium oxide, sodium carbonate, potassium carbonate, sodium phosphate, potassium phosphate or a mixture thereof. In particular, the base is chosen from the group consisting of alkali metal or alkaline-earth metal hydroxides and a mixture thereof. More particularly, the base is chosen from the group consisting of sodium hydroxide, potassium hydroxide or calcium hydroxide and a mixture thereof.

Advantageously, said basic aqueous mixture has a content of said base of from 20% to 80% by weight relative to the total weight of said mixture, preferably a content of from 30% to 75% by weight relative to said mixture, irrespective of the base.

In this embodiment, step b) is performed at a temperature of from 25° C. to 250° C., advantageously from 25° C. to 150° C., preferably from 25° C. to 100° C.

In this particular embodiment, step b) may be performed in the presence of a nonaqueous, nonalcoholic solvent in addition to said basic aqueous mixture. A phase-transfer catalyst may also be used. Said nonaqueous and nonalcoholic solvent is chosen from the group consisting of acetonitrile, propionitrile, butyronitrile, methylglutaronitrile, adiponitrile, benzonitrile, ethylene carbonate, propylene carbonate, methyl ethyl ketone, methyl isoamyl ketone, diisobutyl ketone, anisole, 2-methyltetrahydrofuran, tetrahydrofuran, dioxane, diglyme, triglyme, tetraglyme, N,N-dimethylformamide, N,N-dimethylacetamide, N-methylpyrrolidinone, sulfolane, dimethyl sulfoxide, perfluoro-N-methylmorpholine, perfluorotetrahydrofuran, and mixtures thereof. Preferably, said nonaqueous and nonalcoholic solvent is chosen from acetonitrile, adiponitrile, 2-methyltetrahydrofuran, tetrahydrofuran, dioxane, diglyme and tetraglyme.

The phase-transfer catalyst is a substance which facilitates the transfer of ionic compounds from an aqueous phase to an organic phase. The phase-transfer catalyst is preferably chosen from the group consisting of crown ethers, onium salts, cryptands, polyalkylene glycol ethers and mixtures thereof. The amount of phase-transfer catalyst is from 0.001 to 10 mol % relative to the amount of base in the liquid phase, advantageously from 0.01 to 5 mol % relative to the amount of base in the liquid phase, preferably from 0.05 to 5 mol % relative to the amount of base in the liquid phase.

Crown ethers are cyclic molecules in which the ether groups are linked via a dimethylene group; the compounds form a molecular structure that is capable of trapping an alkali metal ion. The crown ethers include 18-crown-6 used in combination with a basic aqueous mixture containing KOH, 15-crown-5 used in combination with a basic aqueous mixture containing NaOH, 12-crown-4 used in combination with a basic aqueous mixture containing LiOH. The onium salts include quaternary phosphonium salts and quaternary ammonium salts of the formula $R^aR^bR^cR^dP^{(+)}X^-$ or $R^aR^bR^cR^dN^{(+)}X^-$ in which $R^a$, $R^b$, $R^c$ and $R^d$ are independently chosen from a $C_1$-$C_{40}$ alkyl, $C_6$-$C_{40}$ aryl or $C_6$-$C_{40}$ aralkyl group and X is chosen from the group consisting of F, Cl, Br, I, OH, $CO_3$, $HCO_3$, $SO_4$, $HSO_4$, $H_2PO_4$, $HPO_4$ and $PO_4$. For example, the onium salts include tetramethylammonium chloride, tetramethylammonium bromide, benzyltriethylammonium chloride, methyltrioctylammonium chloride, tetra-n-butylammonium chloride, tetra-n-butylammonium bromide, tetra-n-butylphosphonium chloride, tetraphenylphosphonium bromide, tetraphenylphosphonium chloride, triphenylmethylphosphonium bromide and triphenylmethylphosphonium chloride. The polyalkylene glycol ethers include the compounds of formula $R^fO(R^eO)_tR^g$ in which $R^e$ is an alkylene group containing two or more carbon atoms and each $R^f$ and $R^g$ is, independently, H, alkyl, aryl or aralkyl and t is an integer greater than 2. The polyalkylene glycol ethers include, for example, diethylene glycol, triethylene glycol, tetraethylene glycol, pentaethylene glycol, hexaethylene glycol, diisopropylene glycol, dipropylene glycol, dipropylene glycol, tripropylene glycol, tetrapropylene glycol, tetramethylene glycol, and monoalkyl ethers thereof, dialkyl ethers thereof, and polyalkylene glycols such as polyethylene glycol dimethyl ether and polyethylene glycol dibutyl ether. Among the cryptands, mention may be made of 4,7,13,16,21,24-hexaoxa-1,10-diazabicyclo-(8.8.8)hexacosane (Cryptand™ 222 and Kryptofix™ 222).

According to a preferred embodiment, depending on the base used, an iodide salt is formed.

This salt may be KI, $CaI_2$ or NaI, for example.

According to a preferred embodiment, step b) is performed at a pressure of from 1 bar absolute to 20 bar absolute, preferably from 3 to 15 bar absolute.

Step c) of the Process

Preferably, the present process comprises a step c) of purifying stream B obtained in step b) to form a stream B1 comprising said iodofluoroolefin and a stream B2 comprising impurities, by-products or unreacted starting materials. Preferably, after the purification step, the content of said iodofluoroolefin in said stream B1 is greater than 90%, advantageously greater than 92%, preferably greater than 94%, more preferentially greater than 96%, in particular greater than 98%, more particularly greater than 99%. Said stream B is preferably purified by distillation, azeotropic distillation, distillation under pressure, extractive distillation, cold separation, absorption in a solvent or a combination thereof. Said stream B may also be separated or purified by placing in contact with an adsorbent. Said adsorbent may be a zeolite or a molecular sieve having a pore aperture with an average diameter of between 3 ångströms and 11 ångströms, advantageously between 4 ångströms and 10 ångströms, preferably between 5 ångströms and 10 ångströms.

The present process can be performed continuously or in a batchwise or semi-batchwise manner. Steps a) and b) may be performed in two different reactors or in a single reactor. When several reactors are used, they are arranged in series.

Preferably, in order to avoid corrosion problems, the reactor(s) in which steps a) and b) are performed are made of a material comprising a base layer made of a material M1 and an inner layer made of a material M2.

Advantageously, the material M2 comprises at least 40% by weight of nickel relative to the total weight of the material M2. Preferably, the material M2 comprises at least 45% by weight of nickel, more preferentially at least 50% by weight of nickel, in particular at least 55% by weight of nickel, more particularly at least 60% by weight of nickel, preferably at least 65% by weight of nickel, more preferably at least 70% by weight of nickel relative to the total weight of the material M2.

The material M2 may also comprise chromium in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

The material M2 may also comprise molybdenum in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

Preferably, the material M2 is Monel®, Hastelloy®, Inconel® or Incoloy®.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1. More particularly, the material M1 may comprise between 0.01% and 0.2% by weight of carbon on the basis of the total weight of the material M1.

Preferably, said base layer and said inner layer are placed against each other by hot or cold plating, hot or cold rolling or welding.

EXAMPLE

Example 1

Step a): The equipment used consists of a 2.0 L Hastelloy C276 autoclave, equipped with a pressure indicator, a thermometric probe, a bursting disc and a magnetic bar stirring system. The following are successively introduced into the autoclave: 140.0 g (0.55 mol) of iodine, 750.0 g of anhydrous ethanol and 60.0 g (0.52 mol) of $CF_3$—CF═$CH_2$ (HFO-1234yf). The reactor is heated at 85° C. for 11 hours and then cooled to room temperature. After degassing and then flushing with helium, the reaction mixture is collected after opening the autoclave. The organic phase is washed, dried and then analyzed by gas chromatography (area percentage). The analysis confirms the formation of the diiodofluoroalkane compound $CF_3$—CFI—$CH_2$I (95.3% conversion with 96.1% selectivity).

Step b): A reactor consisting of an Inconel 600 tube with an inside diameter of 28 mm and a length of 640 mm, placed vertically in a tubular furnace, is used. The catalytic bed consists of a lower 40 mm layer of corundum, followed by an 85 mm layer of chromium oxyfluoride catalyst containing between 15% and 20% by weight of preactivated fluorine. A gas stream composed of the washed and dried organic phase obtained from step a) and a nitrogen gas stream (volume ratio 1/2) is passed over this catalyst at a temperature of 300° C. At the reactor outlet, the gases are washed and then dried and condensed in a cold trap. A sample is taken and analyzed by gas chromatography (area percentage). The yield of $CF_3$—CF═CHI, expressed by the ratio of the number of moles of $CF_3$—CF═CHI detected to the number of moles of HFO-1234yf initially introduced, is 83.8%.

Example 2

Example 1 was repeated with intermediate purification of the diiodofluoroalkane compound by distillation to totally remove the excess iodine and the impurities. The yield of $CF_3$—CF=CHI after the two reaction steps was about 78.7%.

Invention V

Summary of Invention V

According to a first aspect, the invention relates to a process for producing an iodofluoralkane compound, comprising the steps of:

a) placing an olefin in contact with iodine ($I_2$) in the liquid phase, to form a diiodoalkane compound;

b) fluorinating said diiodoalkane compound with hydrogen fluoride to form a stream B comprising an iodofluoroalkane compound.

According to a preferred embodiment, said diiodoalkane compound is dried before being used in step b).

According to a preferred embodiment, said diiodoalkane compound is purified before being used in step b).

According to a preferred embodiment, said stream B also comprises unreacted hydrogen fluoride, and said stream B is separated to form a stream B1 comprising said iodofluoroalkane compound and a stream B2 comprising unreacted hydrogen fluoride.

According to a preferred embodiment, the stream B2 is recycled into step b).

According to a preferred embodiment, said olefin is a fluoroolefin.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, CI, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

According to a preferred embodiment, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said diiodoalkane compound obtained in step a) is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

According to a preferred embodiment, said diiodoalkane compound obtained in step a) is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_1$-$C_{10}$ perfluoroaryl radical; provided that at least one of the substituents $R^1$, $R^2$, $R^3$ or $R^4$ is F or is a perfluoro radical as defined above.

According to a preferred embodiment, said diiodoalkane compound is of formula (II) $(R^1)(R^2)C(I)$—$C(I)(R^3)(R^4)$ obtained in step a) in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said iodofluoroalkane compound obtained in step b) is of formula (II) $(R^1)(R^2)CF$—$C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

According to a preferred embodiment, said iodofluoroalkane compound obtained in step b) is of formula (II) $(R^1)(R^2)CF$—$C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

According to a preferred embodiment, said iodofluoroalkane compound obtained in step b) is of formula (II) $(R^1)(R^2)CF$—$C(I)(R^3)(R^4)$ in which $R^1$, $R^2$, $R^3$ and $R^4$ are, independently of each other, chosen from the group consisting of H, F or $Y^1$—[—$C(Y^2)(Y^3)$—]$_n$— in which $Y^1$, $Y^2$ and $Y^3$ are, independently of each other and independently for each unit n, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

According to a preferred embodiment, said fluoroolefin is chosen from the group consisting of CHF=$CH_2$, $CF_2$=$CH_2$, CHF=CHF, $CF_2$=CHF, $CF_2$=$CF_2$, $CH_3$—CF=$CH_2$, $CH_3$—CH=CHF, $CH_2F$—CH=$CH_2$, $CH_3$—CF=CHF, $CH_2F$—CF=$CH_2$, $CH_3$—CH=$CF_2$, $CH_2F$—CH=CHF, $CHF_2$—CH=$CH_2$, $CH_3$—CF=$CF_2$, $CH_2F$—CF=CHF, $CHF_2$—CF=$CH_2$, $CH_2F$—CH=$CF_2$, $CHF_2$—CH=CHF, $CF_3$—CH=$CH_2$, $CH_2F$—CF=$CF_2$, $CHF_2$—CF=CHF, $CF_3$—CF=$CH_2$, $CHF_2$—CH=$CF_2$, $CF_3$—

$CH{=}CHF$, $CHF_2$—$CF{=}CF_2$, $CF_3$—$CF{=}CHF$, $CF_2$—$CH{=}CF_2$, $CF_3$—$CF{=}CF_2$; preferably from the group consisting of $CF_2{=}CH_2$, $CF_2{=}CHF$, $CF_2{=}CF_2$, $CF_3$—$CH{=}CH_2$, $CF_3$—$CF{=}CH_2$, $CF_3$—$CH{=}CHF$, $CF_3$—$CF{=}CHF$, $CF_3$—$CF{=}CF_2$.

According to a preferred embodiment, said diiodoalkane compound is chosen from the group consisting of CHFI—$CH_2I$, $CF_2I$—$CH_2I$, CHFI—CHFI, $CF_2I$—CHFI, $CF_2I$—$CF_2I$, $CH_3$—CFI—$CH_2I$, $CH_3$—CHI—CHFI, $CH_2F$—CHI—$CH_2I$, $CH_3$—CFI—CHFI, $CH_2F$—CFI—$CH_2I$, $CH_3$—CHI—$CF_2I$, $CH_2F$—CHI—CHFI, $CHF_2$—CHI—$CH_2I$, $CH_3$—CFI—$CF_2I$, $CH_2F$—CFI—CHFI, $CHF_2$—CFI—$CH_2I$, $CH_2F$—CHI—$CF_2I$, $CHF_2$—CHI—CHFI, $CF_3$—CHI—$CH_2I$, $CH_2F$—CFI—$CF_2I$, $CHF_2$—CFI—CHFI, $CF_3$—CFI—$CH_2I$, $CHF_2$—CHI—$CF_2I$, $CF_3$—CHI—CHFI, $CHF_2$—CFI—$CF_2I$, $CF_3$—CFI—CHFI, $CF_3$—CHI—$CF_2I$, $CF_3$—CFI—$CF_2I$; preferably from the group consisting of $CF_2I$—$CH_2I$, $CF_2I$—CHFI, $CF_2I$—$CF_2I$, $CF_3$—CHI—$CH_2I$, $CF_3$—CFI—$CH_2I$, $CF_3$—CHI—CHFI, $CF_3$—CFI—CHFI, $CF_3$—CFI—$CF_2I$.

According to a preferred embodiment, said iodofluoroalkane compound is chosen from the group consisting of $CHF_2$—$CH_2I$, CHFI—$CH_2F$, $CF_2$—$CH_2I$, $CF_2I$—$CH_2F$, $CHF_2$—CHFI, $CF_3$—CHFI, $CF_2I$—$CHF_2$, $CF_3$—$CF_2I$, $CH_3$—$CF_2$—$CH_2I$, $CH_3$—CFI—$CH_2F$, $CH_3$—CHF—CHFI, $CH_3$—CHI—$CHF_2$, $CH_2F$—CHF—$CH_2I$, $CH_2F$—CHI—$CH_2F$, $CH_3$—$CF_2$—CHFI, $CH_3$—CFI—$CHF_2$, $CH_2F$—$CF_2$—$CH_2I$, $CH_2F$—CFI—$CH_2F$, $CH_3$—CHF—$CF_2I$, $CH_3$—CHI—$CF_3$, $CH_2F$—CHF—CHFI, $CH_2F$—CHI—$CHF_2$, $CHF_2$—CHF—$CH_2I$, $CH_3$—$CF_2$—$CF_2I$, $CH_3$—CFI—$CF_3$, $CH_2F$—$CF_2$—CHFI, $CH_2F$—CFI—$CHF_2$, $CHF_2$—$CF_2$—$CH_2I$, $CH_2F$—CHF—$CF_2I$, $CHF_2$—CHF—CHFI, $CHF_2$—CHI—$CHF_2$, $CF_3$—CHF—$CH_2I$, $CF_3$—CHI—$CH_2F$, $CH_2F$—$CF_3$—$CF_2I$, $CHF_2$—$CF_2$—CHFI, $CHF_2$—CFI—$CHF_2$, $CF_3$—$CF_2$—$CH_2I$, $CF_3$—CFI—$CH_2F$, $CHF_2$—CHF—$CF_2I$, $CF_2$—CHF—CHFI, $CF_2$—CHI—$CHF_2$, $CHF_2$—$CF_2$—$CF_2I$, $CF_3$—$CF_2$—CHFI, $CF_3$—CFI—$CHF_2$, $CF_3$—CHF—$CF_2I$, $CF_3$—CHI—$CF_3$, $CF_3$—$CF_2$—$CF_2I$, $CF_3$—CFI—$CF_3$; advantageously, said iodofluoroalkane compound is chosen from the group consisting of $CHF_2$—$CH_2I$, $CF_2I$—$CH_2F$, $CF_3$—$CH_2I$, $CHF_2$—CHFI, $CF_2I$—$CHF_2$, $CF_3$—CHFI, $CF_3$—$CF_2I$, $CH_3$—$CF_2$—$CH_2I$, $CH_3$—CHI—$CHF_2$, $CH_2F$—CHI—$CH_2F$, $CH_3$—$CF_2$—CHFI, $CH_2F$—$CF_2$—$CH_2I$, $CH_3$—CHI—$CF_3$, $CH_2F$—CHI—$CHF_2$, $CHF_2$—CHI—$CH_2F$, $CH_3$—CFI—$CF_3$, $CH_2F$—$CF_2$—CHFI, $CHF_2$—$CF_2$—$CH_2I$, $CH_2F$—CHI—$CF_3$, $CHF_2$—CHI—$CHF_2$, $CF_3$—CHI—$CH_2F$, $CH_2F$—CFI—$CF_3$, $CHF_2$—$CF_2$—CHFI, $CF_3$—CFI—$CH_2F$, $CF_3$—$CF_2$—$CH_2I$, $CHF_2$—CHI—$CF_3$, $CF_2$—CHI—$CHF_2$, $CHF_2$—CFI—$CF_3$, $CF_3$—CFI—$CHF_2$, $CF_3$—$CF_2$—CHFI, $CF_3$—CHI—$CF_3$, $CF_3$—CFI—$CF_3$; preferably, said iodofluoroalkane compound is chosen from the group consisting of $CF_3$—$CH_2I$, $CF_3$—CHFI, $CF_3$—$CF_2I$, $CF_3$—CHI—$CH_2F$, $CF_3$—$CF_2$—$CH_2I$, $CF_3$—CHI—$CHF_2$, $CF_3$—$CF_2$—CHFI, $CF_3$—CFI—$CF_3$.

According to a preferred embodiment, said process comprises:

- converting $CF_2{=}CH_2$ into $CF_2I$—$CH_2I$ in step a) and fluorinating $CF_2I$—$CH_2I$ to $CF_3$—$CH_2I$ in step b); or
- converting $CF_2{=}CHF$ into $CF_2I$—CHFI in step a) and fluorinating $CF_2I$—CHFI to $CF_3$—CHFI in step b); or
- converting $CF_2{=}CF_2$ into $CF_2I$—$CF_2I$ in step a) and fluorinating $CF_2I$—$CF_2I$ to $CF_3$—$CF_2I$ in step b); or
- converting $CF_3$—$CH{=}CH_2$ into $CF_3$—CHI—$CH_2I$ in step a) and fluorinating $CF_3$—CHI—$CH_2I$ to $CF_3$—CHI—$CH_2F$ in step b); or
- converting $CF_3$—$CF{=}CH_2$ into $CF_3$—CFI—$CH_2I$ in step a) and fluorinating $CF_3$—CFI—$CH_2I$ to $CF_3$—$CF_2$—$CH_2I$ in step b); or
- converting $CF_3$—$CH{=}CHF$ into $CF_3$—CHI—CHFI in step a) and fluorinating $CF_3$—CHI—CHFI to $CF_3$—CHI—$CHF_2$ in step b); or
- converting $CF_3$—$CF{=}CHF$ into $CF_3$—CFI—CHFI in step a) and fluorinating $CF_3$—CFI—CHFI to $CF_3$—$CF_2$—CHFI in step b); or
- converting $CF_3$—$CF{=}CF_2$ into $CF_3$—CFI—$CF_2I$ in step a) and fluorinating $CF_3$—CFI—$CF_2I$ to $CF_3$—CFI—$CF_3$ in step b).

According to a preferred embodiment, step b) is performed in the gas phase at a temperature of from 150° C. to 700° C., preferably from 250° C. to 600° C.

According to a preferred embodiment, step b) is performed in the presence of a catalyst chosen from the group consisting of an oxide, oxyhalide or halide of a metal or metalloid from columns 4 to 15 of the Periodic Table.

According to a preferred embodiment, step b) is performed in the presence of a catalyst in the liquid phase at a temperature of from −50° C. to 250° C.

According to a preferred embodiment, step b) is performed in the absence of a catalyst in the liquid phase at a temperature of from 20° C. to 300° C.

According to a preferred embodiment, step a) is performed in the liquid phase in the presence of a solvent S1 chosen from the group consisting of aqueous potassium iodide solutions, ethers, fluorinated ethers, alcohols, fluorinated alcohols, esters, aromatic solvents, fluorinated aromatic solvents, halogenated solvents and mixtures thereof.

Detailed Description of Invention V

According to a first aspect, the invention relates to a process for producing an iodofluoroalkane compound. Preferably, said process comprises a step of placing an olefin in contact with iodine ($I_2$) in the liquid phase, to form a diiodoalkane compound. Preferably, said process also comprises a step of fluorinating said diiodoalkane compound obtained in step a) with hydrogen fluoride to form a stream B comprising an iodofluoroalkane compound.

Step a) of the Process

Step a) of the present process requires an olefin to be placed in contact with iodine in the liquid phase.

For example, said olefin is of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical, a $C_3$-$C_{10}$ cycloalkyl radical, a $C_2$-$C_{10}$ alkenyl radical, a $C_3$-$C_{10}$ cycloalkenyl radical and a $C_6$-$C_{10}$ aryl radical.

Preferably, said olefin is a fluoroolefin.

In particular, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

Said olefin is a fluoroolefin, preferably of formula (I) $(R^1)(R^2)C{=}C(R^3)(R^4)$ in which $R^1$, $R^2$, $R^3$ and $R^4$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

The term "alkyl" denotes a monovalent radical resulting from a linear or branched alkane comprising the number of carbon atoms specified. The term "cycloalkyl" denotes a monovalent radical resulting from a cycloalkane comprising the number of carbon atoms specified. The term "alkenyl" denotes a monovalent radical comprising the number of carbon atoms specified and at least one carbon-carbon double bond. The term "cycloalkenyl" refers to a monovalent radical resulting from a cycloalkene comprising the number of carbon atoms specified and at least one carbon-carbon double bond in its cyclic part. The term "aryl" denotes a monovalent radical resulting from an arene comprising the number of carbon atoms specified.

Preferably, said alkyl, cycloalkyl, alkenyl, cycloalkenyl or aryl radical is not substituted with functional groups other than fluorine. Said radical may nevertheless comprise several fluorine atoms on its carbon chain, for example, said radical may contain from 1 to 10 fluorine atoms, preferably from 1 to 5 fluorine atoms.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_6$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_1$-$C_{10}$ perfluoroaryl radical; provided that at least one of the substituents $R^1$, $R^2$, $R^3$ or $R^4$ is F or is a perfluoro radical as defined above.

Alternatively, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$—]$_n$- in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, I, F or $Y^1$—[—$C(Y^2)(Y^3)$-]$_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $R^4$, $Y^1$, $Y^2$ or $Y^3$ is F.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—$]_n$— in which $Y^1$, $Y^2$ and $Y^3$ are, independently of each other and independently for each unit n, chosen from the group consisting of H and F, and n is an integer from 1 to 10; provided that at least one of the substituents $R^1$, $R^2$, $R^3$, $R^4$, $Y^1$, $Y^2$ or $Y^3$ is F.

Preferably, said olefin is a fluoroolefin of formula (I) $(R^1)(R^2)C{=}C(R^3)(R^4)$ in which $R^1$, $R^2$, $R^3$ and $R^4$ are, independently of each other, chosen from the group consisting of H, F or $Y^1$—[—$C(Y^2)(Y^3)$—$]_n$— in which $Y^1$, $Y^2$ and $Y^3$ are, independently of each other and independently for each unit n, chosen from the group consisting of H and F, and n is an integer from 1 to 5; provided that at least one of the substituents $R^1$, $R^2$, $R^3$, $R^4$, $Y^1$, $Y^2$ or $Y^3$ is F.

Preferably, said olefin is a fluoroolefin chosen from the group consisting of $CHF{=}CH_2$, $CF_2{=}CH_2$, $CHF{=}CHF$, $CF_2{=}CHF$, $CF_2{=}CF_2$, $CH_3$—$CF{=}CH_2$, $CH_3$—$CH{=}CHF$, $CH_2F$—$CH{=}CH_2$, $CH_3$—$CF{=}CHF$, $CH_2F$—$CF{=}CH_2$, $CH_3$—$CH{=}CF_2$, $CH_2F$—$CH{=}CHF$, $CHF_2$—$CH{=}CH_2$, $CH_3$—$CF{=}CF_2$, $CH_2F$—$CF{=}CHF$, $CHF_2$—$CF{=}CH_2$, $CH_2F$—$CH{=}CF_2$, $CHF_2$—$CH{=}CHF$, $CF_3$—$CH{=}CH_2$, $CH_2F$—$CF{=}CF_2$, $CHF_2$—$CF{=}CHF$, $CF_3$—$CF{=}CH_2$, $CHF_2$—$CH{=}CF_2$, $CF_3$—$CH{=}CHF$, $CHF_2$—$CF{=}CF_2$, $CF_3$—$CF{=}CHF$, $CF_3$—$CH{=}CF_2$, $CF_3$—$CF{=}CF_2$; in particular from the group consisting of $CF_2{=}CH_2$, $CF_2{=}CHF$, $CF_2{=}CF_2$, $CF_3$—$CH{=}CH_2$, $CF_3$—$CF{=}CH_2$, $CF_3$—$CH{=}CHF$, $CF_3$—$CF{=}CHF$, $CF_3$—$CF{=}CF_2$.

Said olefin, in particular said fluoroolefin as defined above, may have a boiling point below 100° C. at atmospheric pressure. Advantageously, said olefin, in particular said fluoroolefin as defined above, has a boiling point below 75° C. at atmospheric pressure. Preferably, said olefin, in particular said fluoroolefin as defined above, has a boiling point below 50° C. at atmospheric pressure. More preferentially, said olefin, in particular said fluoroolefin as defined above, has a boiling point below 25° C. at atmospheric pressure. In particular, said olefin, in particular said fluoroolefin as defined above, has a boiling point below 10° C. at atmospheric pressure.

According to a preferred embodiment, step a) may be performed in the presence of a mixture of olefins, or of fluoroolefins as defined above, to result in the coproduction of iodofluoroalkane compounds via corresponding diiodoalkane compounds, in accordance with the present process.

Step a) allows the formation of a diiodoalkane compound. Preferably, said diiodoalkane compound obtained in step a) is of formula (II) $(R^1)(R^2)C(I)$—$C(I)(R^3)(R^4)$.

Said diiodoalkane compound obtained in step a) may be of formula (II) $(R^1)(R^2)C(I)$—$C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical, a $C_3$-$C_{10}$ cycloalkyl radical, a $C_2$-$C_{10}$ alkenyl radical, a $C_2$-$C_{10}$ cycloalkenyl radical and a $C_6$-$C_{10}$ aryl radical.

Advantageously, said diiodoalkane compound obtained in step a) is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_2$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said diiodoalkane compound is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said diiodoalkane compound is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said diiodoalkane compound is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said diiodoalkane compound is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said diiodoalkane compound is of formula (II) $(R^1)(R^2)C(I)$—$C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$—$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Alternatively, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, I, F or $Y^1$—[—$C(Y^2)(Y^3)$—$]_n$— in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, I, F or $Y^1$—[—$C(Y^2)(Y^3)$—$]_n$— in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $R^4$, $Y^1$, $Y^2$ or $Y^3$ is F.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F or $Y^1$—[—$C(Y^2)(Y^3)$—$]_n$— in which $Y^1$, $Y^2$ and $Y^3$ are, independently of each other and independently for each n unit, chosen from the group consisting of H and F; and n is an integer from 1 to 10; provided that at least one of the substituents $R^1$, $R^2$, $R^3$, $R^4$, $Y^1$, $Y^2$ or $Y^3$ is F.

Preferably, said diiodoalkane compound is of formula (II) $(R^1)(R^2)C(I)—C(I)(R^3)(R^4)$ in which $R^1$, $R^2$, $R^3$ and $R^4$ are, independently of each other, chosen from the group consisting of H, F or $Y^1$—[—$C(Y^2)(Y^3)$—$]_n$— in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

In particular, said diiodoalkane compound is chosen from the group consisting of CHFI—$CH_2I$, $CF_2I$—$CH_2I$, CHFI—CHFI, $CF_2I$—CHFI, $CF_2I$—$CF_2I$, $CH_3$—CFI—$CH_2I$, $CH_3$—CHI—CHFI, $CH_2F$—CHI—$CH_2I$, $CH_3$—CFI—CHFI, $CH_2F$—CFI—$CH_2I$, $CH_3$—CHI—$CF_2I$, $CH_2F$—CHI—CHFI, $CHF_2$—CHI—$CH_2I$, $CH_3$—CFI—$CF_2I$, $CH_2F$—CFI—CHFI, $CHF_2$—CFI—$CH_2I$, $CH_2F$—CHI—$CF_2I$, $CHF_2$—CHI—CHFI, $CF_3$—CHI—$CH_2I$, $CH_2F$—CFI—$CF_2I$, $CHF_2$—CFI—CHFI, $CF_3$—CFI—$CH_2I$, $CHF_2$—CHI—$CF_2I$, $CF_3$—CHI—CHFI, $CHF_2$—CFI—$CF_2I$, $CF_3$—CFI—CHFI, $CF_3$—CHI—$CF_2I$, $CF_3$—CFI—$CF_2I$; more particularly from the group consisting of $CF_2I$—$CH_2I$, $CF_2I$—CHFI, $CF_2I$—$CF_2I$, $CF_3$—CHI—$CH_2I$, $CF_3$—CFI—$CH_2I$, $CF_3$—CHI—CHFI, $CF_3$—CFI—CHFI, $CF_3$—CFI—$CF_2I$.

More particularly, step a) of the present process involves:

converting $CF_2$═$CH_2$ into $CF_2I$—$CH_2I$; or
converting $CF_2$═CHF into $CF_2I$—CHFI; or
converting $CF_2$═$CF_2$ into $CF_2I$—$CF_2I$; or
converting $CF_3$—CH═$CH_2$ into $CF_3$—CHI—$CH_2I$; or
converting $CF_3$—CF═$CH_2$ into $CF_3$—CFI—$CH_2I$; or
converting $CF_3$—CH═CHF into $CF_3$—CHI—CHFI; or
converting $CF_3$—CF═CHF into $CF_3$—CFI—CHFI; or
converting $CF_3$—CF═$CF_2$ into $CF_3$—CFI—$CF_2I$.

As mentioned above, step a) may be performed using a mixture of olefins chosen, for example, from the group consisting of $CF_2$═$CH_2$, $CF_2$═CHF, $CF_2$═$CF_2$, $CF_3$—CH═$CH_2$, $CF_3$—CF═$CH_2$, $CF_3$—CH═CHF, $CF_3$—CF═CHF, $CF_3$—CF═$CF_2$, to obtain a stream A comprising a mixture of diiodoalkane compounds chosen, for example, from the group consisting of $CF_2I$—$CH_2I$, $CF_2I$—CHFI, $CF_2I$—$CF_2I$, $CF_3$—CHI—$CH_2I$, $CF_3$—CFI—$CH_2I$, $CF_3$—CHI—CHFI, $CF_3$—CFI—CHFI, $CF_3$—CFI—$CF_2I$.

Preferably, step a) may be performed in the liquid phase. Preferably, step a) is performed in the absence of catalyst. Preferably, step a) is performed in the presence of a solvent S1. Preferably, the solvent S1 is chosen from the group consisting of aqueous potassium iodide solutions, ethers, fluorinated ethers, alcohols, fluorinated alcohols, esters, aromatic solvents, fluorinated aromatic solvents, halogenated solvents and mixtures thereof. Advantageously, the solvent S1 is chosen from the group consisting of aqueous potassium iodide solutions, ethyl and methyl ethers, hydrofluoroethers, ethyl and methyl alcohols, ethyl lactate, toluene, xylenes, para-chlorotrifluoromethylbenzene, hexafluorobenzene, tetrachloromethane, chloroform, dichloromethane, 1-bromopropane and mixtures thereof. The use of a solvent in the present process makes it possible to avoid the problems of clogging associated with the sublimation of iodine and also to limit the formation of impurities (reaction by-products, polymers derived from the olefin, etc.), which makes it possible to achieve selectivities that are particularly advantageous from an industrial viewpoint.

Preferably, the iodine is placed in contact with the olefin, in particular with said fluoroolefin as defined above, at the stoichiometry or in excess thereof. For example, the $I_2$/olefin mole ratio is from 0.1 to 50, preferably from 0.5 to 25, in particular from 1 to 20.

Preferably, the content of oxygen dissolved in the solvent S1 is less than 3000 ppm, advantageously less than 2000 ppm, preferably less than 1000 ppm, more preferentially less than 500 ppm, in particular less than 250 ppm, more particularly less than 100 ppm, preferably less than 50 ppm, preferentially preferably less than 10 ppm. This avoids the degradation of the starting materials and of the desired products. The solvent S1 preferably has a boiling point of from 0° C. to 250° C., preferably from 20° C. to 250° C., in particular from 20° C. to 200° C.

The temperature at which step a) is performed is from 20° C. to 280° C., preferably from 30° C. to 250° C. Step a) may be performed at a pressure of from 0.1 bar to 15 bar, preferably from 1 bara to 10 bara.

Said diiodoalkane compound may be dried before being used in step b). This allows the removal of any traces of water that may be present. The drying may be performed by placing in contact with an adsorbent, an absorbent, a 3 to 5 ångström sieve or zeolites. Said dried diiodoalkane compound may be purified or used as such in step b).

Said diiodoalkane compound may be purified before being used in step b). The purification may be performed before or after the drying step. This allows the removal of certain impurities that may be difficult to separate from the iodofluoroalkane compound. This step also makes it possible to increase the selectivity of step b). The purification may be performed by distillation, azeotropic distillation, distillation under pressure, extractive distillation, cold separation, absorption in a solvent, or by placing in contact with an adsorbent or a combination thereof.

Advantageously, the purification of the diiodoalkane compound is directed toward producing a stream A in which the content of diiodoalkane compound is greater than 90%, advantageously greater than 92%, preferably greater than 94%, more preferentially greater than 96%, in particular greater than 98%, more particularly greater than 99%. This stream A is then used in step b).

When step a) is performed using a mixture of olefins, the purification, if it is performed, affords a mixture of diiodoalkane compounds or a particular diiodoalkane compound depending on the conditions used for performing the purification.

Alternatively, said dried diiodoalkane compound may be used directly in step b) without being purified after the drying step. This can be done when step a) is performed with high conversion and selectivity, for example greater than 90%, preferably greater than 95%. The absence of purification between step a) and step b) is advantageous from the point of view of the overall productivity of the process, since a purification step may give rise to significant costs.

The diiodoalkane compound used in step b) is preferably anhydrous, i.e. the stream containing the diiodoalkane compound used in step b) is anhydrous. The term "anhydrous" refers here to a water content by mass in the stream containing said diiodoalkane compound and used in step b) of less than 500 ppm of water, advantageously less than 250 ppm, preferably less than 100 ppm of water, more preferentially less than 50 ppm of water, in particular less than 25 ppm of water, more particularly less than 10 ppm, more preferably less than 5 ppm of water; preferentially preferably, said diiodoalkane compound or the stream in which it is contained for performing step b) is free of water.

Step b) of the Process

Step b) of the present process is a step of fluorinating said diiodoalkane compound with hydrogen fluoride to form a stream B comprising an iodofluoroalkane compound. Said diiodoalkane compound is as defined above in step a) of the process. Advantageously, said iodofluoroalkane compound obtained in step b) is of formula (III) $(R^1)(R^2)CF—C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical, a $C_3$-$C_{10}$ cycloalkyl radical, a $C_2$-$C_{10}$ alkenyl radical, a $C_3$-$C_{10}$ cycloalkenyl radical and a $C_6$-$C_{10}$ aryl radical.

Thus, said iodofluoroalkane compound is preferably of formula (III) $(R^1)(R^2)CF—C(I)(R^3)(R^4)$ in which $R^1$, $R^2$, $R^3$ and $R^4$ are, independently of each other, chosen from the group consisting of H, F, Cl, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; provided that at least one of the substituents $R^1$, $R^2$, $R^3$ or $R^4$ is F or is a radical as defined above including at least one fluorine atom.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 10 fluorine atoms, a $C_3$-$C_{10}$ cycloalkyl radical optionally substituted with 1 to 10 fluorine atoms, a $C_2$-$C_{10}$ alkenyl radical optionally substituted with 1 to 10 fluorine atoms, a $C_3$-$C_{10}$ cycloalkenyl radical optionally substituted with 1 to 10 fluorine atoms, and a $C_6$-$C_{10}$ aryl radical optionally substituted with 1 to 10 fluorine atoms; with the proviso that at least one of the substituents $R^1$, $R^2$, $R^3$ or $R^4$ is F or is a radical as defined above including from 1 to 10 fluorine atoms.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, I, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms;

provided that at least one of the substituents $R^1$, $R^2$, $R^3$ or $R^4$ is F or is a radical as defined above including from 1 to 5 fluorine atoms.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, a $C_1$-$C_{10}$ alkyl radical optionally substituted with 1 to 5 fluorine atoms, a $C_3$-$C_{10}$ cycloalkyl radical optionally substituted with 1 to 5 fluorine atoms, a $C_2$-$C_{10}$ alkenyl radical optionally substituted with 1 to 5 fluorine atoms, a $C_3$-$C_{10}$ cycloalkenyl radical optionally substituted with 1 to 5 fluorine atoms, and a $C_6$-$C_{10}$ aryl radical optionally substituted with 1 to 5 fluorine atoms; provided that at least one of the substituents $R^1$, $R^2$, $R^3$ or $R^4$ is F or is a radical as defined above including from 1 to 5 fluorine atoms.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, I, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, a $C_1$-$C_{10}$ perfluoroalkyl radical, a $C_3$-$C_{10}$ perfluorocycloalkyl radical, a $C_2$-$C_{10}$ perfluoroalkenyl radical, a $C_3$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

Alternatively, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each unit n, chosen from the group consisting of H, I and F; and n is an integer from 1 to 10; provided that at least one of the substituents $R^1$, $R^2$, $R^3$, $R^4$, $Y^1$, $Y^2$ or $Y^3$ is F.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, I, F or $Y^1—[—C(Y^2)(Y^3)—]_n—$ in which $Y^1$, $Y^2$ and $Y^3$ are, independently of each other and independently for each unit n, chosen from the group consisting of H, I and F; and n is an integer from 1 to 5; provided that at least one of the substituents $R^1$, $R^2$, $R^3$, $R^4$, $Y^1$, $Y^2$ or $Y^3$ is F.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F or $Y^1—[—C(Y^2)(Y^3)—]_n—$ in which $Y^1$, $Y^2$ and $Y^3$ are, independently of each other and independently for each n unit, chosen from the group consisting of H and F; and n is an integer from 1 to 10; provided that at least one of the substituents $R^1$, $R^2$, $R^3$, $R^4$, $Y^1$, $Y^2$ or $Y^3$ is F.

Preferably, said iodofluoroalkane compound is of formula (III) $(R^1)(R^2)CF—C(I)(R^3)(R^4)$ in which $R^1$, $R^2$, $R^3$ and $R^4$ are, independently of each other, chosen from the group consisting of H, F or $Y^1—[—C(Y^2)(Y^3)—]_n—$ in which $Y^1$, $Y^2$ and $Y^3$ are, independently of each other and independently for each n unit, chosen from the group consisting of H and F; and n is an integer from 1 to 5; provided that at least one of the substituents $R^1$, $R^2$, $R^3$, $R^4$, $Y^1$, $Y^2$ or $Y^3$ is F.

Preferably, said iodofluoroalkane compound is chosen from the group consisting of $CHF_2—CH_2I$, $CHFI—CH_2F$, $CF_3—CH_2I$, $CF_2I—CH_2F$, $CHF_2—CHFI$, $CF_3—CHFI$, $CF_2I—CHF_2$, $CF_3—CF_2I$, $CH_3—CF_2—CH_2I$, $CH_3—CFI—CH_2F$, $CH_3—CHF—CHFI$, $CH_3—CHI—CHF_2$, $CH_2F—CHF—CH_2I$, $CH_2F—CHI—CH_2F$, $CH_3—CF_2—CHFI$, $CH_3—CFI—CHF_2$, $CH_2F—CF_2—CH_2I$, $CH_2F—CFI—CH_2F$, $CH_3—CHF—CF_2I$, $CH_3—CHI—CF_3$, $CH_2F—CHF—CHFI$, $CH_2F—CHI—CHF_2$, $CHF_2—CHF—CH_2I$, $CH_3—CF_2—CF_2I$, $CH_3—CFI—CF_3$, $CH_2F—CF_2—CHFI$, $CH_2F—CFI—CHF_2$, $CHF_2—CF_2—CH_2I$, $CH_2F—CHF—CF_2I$, $CHF_2—CHF—CHFI$, $CHF_2—CHI—CHF_2$, $CF_3—CHF—CH_2I$, $CF_3—CHI—CH_2F$, $CH_2F—CF_2—CF_2I$, $CHF_2—CF_2—CHFI$, $CHF_2—CFI—CHF_2$, $CF_3—CF_2—CH_2I$, $CF_3—CFI—CH_2F$, $CHF_2—CHF—CF_2I$, $CF_2—CHF—CHFI$, $CF_3—CHI—CHF_2$, $CHF_2—CF_2—CF_2I$, $CF_3—CF_2—CHFI$, $CF_3—CFI—CHF_2$, $CF_3—CHF—CF_2I$, $CF_3—CHI—CF_3$, $CF_3—CF_3—CF_2I$, $CF_3—CFI—CF_3$; advantageously, said iodofluoroalkane compound is chosen from the group consisting of $CHF_2—CH_2I$, $CF_2I—CH_2F$, $CF_3—CH_2I$, $CHF_2—CHFI$, $CF_2I—CHF_2$, $CF_2—CHFI$, $CF_3—CF_2I$, $CH_3—CF_2—CH_2I$, $CH_3—CHI—CHF_2$, $CH_2F—CHI—CH_2F$, $CH_3—CF_2—CHFI$, $CH_2F—CF_2—CH_2I$, $CH_3—CHI—CF_3$, $CH_2F—CHI—CHF_2$, $CHF_2—CHI—CH_2F$, $CH_3—CFI—CF_3$, $CH_2F—CF_2—CHFI$, $CHF_2—CF_2—CH_2I$, $CH_2F—CHI—CF_3$, $CHF_2—CHI—CHF_2$, $CF_3—CHI—CH_2F$, $CH_2F—CFI—CF_3$, $CHF_2—CF_2—CHFI$, $CF_3—CFI—CH_2F$, $CF_3—CF_2—CH_2I$, $CHF_2—CHI—CF_3$, $CF_3—CHI—CHF_2$, $CHF_2—CFI—CF_3$, $CF_3—CFI—CHF_2$, $CF_3—CF_2—CHFI$, $CF_2—CHI—CF_3$, $CF_3—CFI—CF_3$; preferably, said iodofluoroalkane compound is chosen from the group consisting of $CF_3—CH_2I$, $CF_3—CHFI$, $CF_3—CF_2I$, $CF_3—CHI—CH_2F$, $CF_3—CF_2—CH_2I$, $CF_3—CHI—CHF_2$, $CF_3—CF_2—CHFI$, $CF_3—CFI—CF_3$.

Thus, step b) of the present process involves:

fluorinating $CF_2I—CH_2I$ to $CF_3—CH_2I$; or
fluorinating $CF_2I—CHFI$ to $CF_3—CHFI$; or
fluorinating $CF_2I—CF_2I$ to $CF_3—CF_2I$; or
fluorinating $CF_3—CHI—CH_2I$ to $CF_3—CHI—CH_2F$; or
fluorinating $CF_3—CFI—CH_2I$ to $CF_3—CF_2—CH_2I$; or
fluorinating $CF_3—CHI—CHFI$ to $CF_3—CHI—CHF_2$; or
fluorinating $CF_3—CFI—CHFI$ to $CF_3—CF_2—CHFI$; or
fluorinating $CF_3—CFI—CF_2I$ to $CF_3—CFI—CF_3$.

When step a) has been performed using a mixture of olefins, step b) is preferably performed using a mixture of diiodoalkane compounds to form a mixture of iodofluoroalkane compounds.

The fluorination in step b) involves the reaction between said diiodoalkane compound and hydrofluoric acid. This makes it possible to replace an iodine atom with a fluorine atom.

Preferably, the hydrofluoric acid (HF) is anhydrous. The term "anhydrous" refers here to hydrofluoric acid containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, the hydrofluoric acid is free of water. The use of anhydrous hydrofluoric acid in the present process avoids the formation of impurities. The use of anhydrous hydrofluoric acid makes it possible to achieve selectivities that are particularly advantageous from an industrial viewpoint. Preferably, the hydrofluoric acid is anhydrous and in gaseous form.

Preferably, the hydrofluoric acid is placed in contact with the diiodoalkane compound at the stoichiometry or in slight excess thereof. For example, the HF/diiodoalkane compound mole ratio is from 1 to 10, preferably from 1 to 5. An excessive amount of hydrofluoric acid promotes excessive fluorination of the diiodoalkane compound. Thus, in the presence of a mole ratio of greater than 15, a compound of formula (IV) $(R^1)(R^2)CF—C(F)(R^3)(R^4)$ is formed in large or even predominant amount. The substituents $R^1$, $R^2$, $R^3$ and $R^4$ in the compound of formula (IV) are as defined above for the iodofluoroalkane compound of formula (III).

Step b) may be performed in the liquid or gas phase. Step b) may be performed in the presence or absence of a catalyst.

Gas Phase Step b)

In the gas phase, step b) is performed at a temperature of from 150° C. to 700° C., preferably from 250° C. to 600° C.

Irrespective of whether step b) is performed in the gas phase in the presence or absence of a catalyst, the pressure in this step is from 0.1 bar to 30 bar, preferably from 1 bar to 20 bar, in particular from 1 bar to 15 bar.

When step b) is performed in the gas phase, step b) may be performed in the presence of a catalyst. Preferably, the catalyst is chosen from the group consisting of an oxide, oxyhalide or halide of a metal or metalloid from columns 4 to 15 of the Periodic Table. Preferably, the catalyst is a chromium oxide, chromium oxyfluoride or a chromium fluoride. The chromium oxyfluoride preferably has a fluorine content of from 10% to 50% by weight, preferably from 20% to 50% by weight, in particular from 30% to 50% by weight. The fluorine content is measured ionometrically or by weight change of the catalyst or by any other quantitative method known to those skilled in the art. The chromium oxyfluoride or chromium fluoride catalyst preferably has a specific surface area of from 15 to 100 $m^2/g$. The chromium oxide catalyst preferably has a specific surface area of from 100 to 300 $m^2/g$. The specific surface area is measured on a Micromeritics Gemini 2360 machine using the standard 5-point method (BET method). When the catalyst is a chromium oxide, chromium oxyfluoride or chromium fluoride, it may also contain from 0.5% to 10% by weight of a cocatalyst relative to the total weight of the catalyst. Said cocatalyst is chosen from Cr, Ni, Zn, Ti, V, Zr, Mo, Ge, Sn, Pb and Mg. Mention may also be made of $AlF_3$, $SbCl_5$ and $SbF_5$ as catalysts. The catalyst may be deposited onto a porous support. The porous support may be chosen from activated charcoals, graphite, aluminas and alumina fluorides.

The catalyst may be activated prior to its use in step b). For example, said catalyst may be activated in the presence of oxygen, air, HF or a mixture thereof.

The catalyst may also deactivate over time. Thus, step b) may be performed in the presence of oxygen or air or an oxygen-nitrogen mixture. If oxygen is used in step b), it is present in an amount of from 0.005 mol % to 10 mol % relative to the molar amount of diiodoalkane.

The catalyst may also be regenerated after the present process has been performed. The regeneration step may comprise placing the catalyst in contact with a stream of oxygen or air at a temperature of from 200° C. to 700° C.

Alternatively, step b) may be performed in the gas phase in the absence of a catalyst.

Liquid Phase Step b)

In the liquid phase, step b) may be performed in the presence or absence of a solvent.

Step b) may be performed in the liquid phase in the presence of a solvent S2. Preferably, the solvent S2 is anhydrous. The term "anhydrous" refers here to a solvent S2 containing less than 500 ppm of water, advantageously less than 250 ppm, preferably less than 100 ppm of water, more preferentially less than 50 ppm of water, in particular less than 25 ppm of water, more particularly less than 10 ppm, preferably less than 5 ppm of water; preferentially preferably, said solvent S2 is free of water. The solvent S2 has a boiling point of from 0° C. to 250° C., preferably from 20° C. to 250° C., in particular from 20° C. to 200° C. Said solvent S2 is chosen from the group consisting of 1,1,1,2,2,3,4,5,5,5-decafluoropentane, 1,1,1,3,3-pentafluorobutane, 1,1,2-trichloro-2,2-difluoroethane, 1,1,2-trichloro-2-fluoroethane, 1,1,2-trichloro-1,2,2-trifluoroethane, nitromethane, nitrobenzene, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof.

Step b) may be performed in the liquid phase in the absence of a solvent. In this case, the temperature and pressure conditions are such that said diiodoalkane compound and/or hydrofluoric acid are in liquid form. In addition, if a catalyst is present, the temperature and pressure conditions may be adapted so as to keep the catalyst in liquid form.

Preferably, in the liquid phase, step b) is performed in the presence of a catalyst (independently of the presence or absence of a solvent). Said catalyst may be based on a metal or metals chosen from the metals of columns 1 to 15 of the Periodic Table of Elements and mixtures thereof. Use may be made of a Lewis acid, a catalyst based on a metal halide, notably based on an antimony, tin, tantalum or titanium halide, transition metal halides such as iron, niobium, molybdenum or cesium halides, transition metal oxides, halides of metals from group IVb, halides of metals from group Vb, a fluorinated chromium halide, a fluorinated chromium oxide or a mixture of the two. Metal chlorides and fluorides may advantageously be used. Examples of such catalysts include: $SbCl_5$, $SbCl_3$, $TiCl_4$, $SnCl_4$, $TaCl_5$, $NbCl_5$, $TiCl_4$, $FeCl_3$, $MoCl_6$, CsCl, KCl, $MgCl_2$ and the corresponding fluorinated derivatives thereof. Pentavalent metal halides are suitable for use.

Preferably, stream B formed in step b) is recovered in gaseous form. This is particularly advantageous when step b) is performed in the liquid phase. The reaction product is thus withdrawn from the reactor in gaseous form while at the same time maintaining all or part of the reaction mixture (solvent, starting materials) in liquid form.

Step c) of the Process

As mentioned above, stream B comprises the iodofluoroalkane compound. Preferably, said stream B also comprises unreacted hydrogen fluoride. Said stream B also comprises hydrogen iodide, resulting from the replacement of an iodine atom with a fluorine atom. In particular, said stream B is separated to form a stream B1 comprising said iodofluoroalkane compound and a stream B2 comprising unreacted hydrogen fluoride and hydrogen iodide (process step c)).

Stream B may also comprise a compound of formula (IV) as described above and/or an unreacted diiodoalkane compound. The compound of formula (IV) may be contained, after separation, in stream B1 or in stream B2 or in both. In this case, streams B1 and B2 can be purified to remove the compound of formula (IV). The unreacted diiodoalkane compound is preferably contained in stream B2.

Said streams B, B1 and B2 are preferably separated and/or purified by distillation, azeotropic distillation, distillation under pressure, extractive distillation, cold separation, absorption in a solvent or a combination thereof. Said streams B, B1 and B2 may also be separated or purified by placing in contact with an adsorbent. Said adsorbent may be a zeolite or a molecular sieve having a pore aperture with an average diameter of between 3 ångströms and 11 ångströms, advantageously between 4 ångströms and 10 ångströms, preferably between 5 ångströms and 10 ångströms.

Preferably stream B2 is recycled into step b); preferably, stream B2 free of compound (IV) is recycled into step b). This recycling step improves the overall yield of the process (better conversion) and saves on expensive reagents (and catalysts), while at the same time minimizing the environmental impact. Without this recycling step, the unreacted hydrofluoric acid would have to be incinerated, thus increasing the carbon footprint of the process.

The present process can be performed continuously or in a batchwise or semi-batchwise manner. The present process may be performed in at least two reactors in series or in a single reactor comprising at least two reaction zones.

Thus, as described above in the present patent application, the present process involves:

- converting $CF_2{=}CH_2$ into $CF_2I{-}CH_2I$ in step a) and fluorinating $CF_2I{-}CH_2I$ to $CF_3{-}CH_2I$ in step b); or
- converting $CF_2{=}CHF$ into $CF_2I{-}CHFI$ in step a) and fluorinating $CF_2I{-}CHFI$ to $CF_3{-}CHFI$ in step b); or
- converting $CF_2{=}CF_2$ into $CF_2I{-}CF_2I$ in step a) and fluorinating $CF_2I{-}CF_2I$ to $CF_3{-}CF_2I$ in step b); or
- converting $CF_3{-}CH{=}CH_2$ into $CF_3{-}CHI{-}CH_2I$ in step a) and fluorinating $CF_3{-}CHI{-}CH_2I$ to $CF_3{-}CHI{-}CH_2F$ in step b); or
- converting $CF_3{-}CF{=}CH_2$ into $CF_3{-}CFI{-}CH_2I$ in step a) and fluorinating $CF_3{-}CFI{-}CH_2I$ to $CF_3{-}CF_3{-}CH_2I$ in step b); or
- converting $CF_3{-}CH{=}CHF$ into $CF_3{-}CHI{-}CHFI$ in step a) and fluorinating $CF_3{-}CHI{-}CHFI$ to $CF_3{-}CHI{-}CHF_2$ in step b); or
- converting $CF_3{-}CF{=}CHF$ into $CF_3{-}CFI{-}CHFI$ in step a) and fluorinating $CF_3{-}CFI{-}CHFI$ to $CF_3{-}CF_3{-}CHFI$ in step b); or
- converting $CF_3{-}CF{=}CF_2$ into $CF_3{-}CFI{-}CF_2I$ in step a) and fluorinating $CF_3{-}CFI{-}CF_2I$ to $CF_3{-}CFI{-}CF_3$ in step b).

Preferably, in order to avoid corrosion problems, the reactor(s) in which step a) and step b) are performed are made of a material comprising a base layer made of a material M1 and an inner layer made of a material M2.

Advantageously, the material M2 comprises at least 40% by weight of nickel relative to the total weight of the material M2. Preferably, the material M2 comprises at least 45% by weight of nickel, more preferentially at least 50% by weight of nickel, in particular at least 55% by weight of nickel, more particularly at least 60% by weight of nickel, preferably at least 65% by weight of nickel, more preferably at least 70% by weight of nickel relative to the total weight of the material M2.

The material M2 may also comprise chromium in a content of less than 35% by weight relative to the total weight of the material M2, advantageously less than 30% by weight, preferably less than 20% by weight, more preferentially less than 15% by weight, in particular less than 10% by weight, more particularly less than 5% by weight relative to the total weight of the material M2.

The material M2 may also comprise molybdenum in a content of less than 35% by weight on the basis of the total weight of the material M2, advantageously less than 30% by weight, preferably less than 20% by weight, more preferentially less than 15% by weight, in particular less than 10% by weight, more particularly less than 5% by weight on the basis of the total weight of the material M2.

Preferably, the material M2 is Monel®, Hastelloy®, Inconel® or Incoloy®.

According to a preferred embodiment, the material M1 comprises at least 70% by weight of iron, advantageously at least 75% by weight, preferably at least 80% by weight, more preferentially at least 85% by weight, in particular at least 90% by weight, more particularly at least 95% by weight of iron on the basis of the total weight of the material M1.

The material M1 may also comprise less than 2% by weight of carbon, advantageously less than 1.5% by weight, preferably less than 1% by weight, more preferentially less than 0.75% by weight, in particular less than 0.5% by weight, more particularly less than 0.2% by weight, favorably less than 0.1% by weight on the basis of the total weight of the material M1. More particularly, the material M1 may comprise between 0.01% and 0.2% by weight of carbon on the basis of the total weight of the material M1.

Preferably, said base layer and said inner layer are placed against each other by hot or cold plating, hot or cold rolling or welding.

EXAMPLES

Example 1—Synthesis of $CF_3{-}CFI{-}CF_3$

Step a): The equipment used consisted of a 1.0 L Hastelloy C276 autoclave, equipped with a pressure indicator, a thermometric probe, a bursting disc and a magnetic bar stirring system.

The following were successively introduced into the autoclave: 127.0 g (0.5 mol) of iodine, 83.0 g (0.5 mol) of potassium iodide, 180.0 g of water and 60.0 g (0.4 mol) of hexafluoropropene ($C_3F_6$). The reactor was heated to 100° C.: the pressure gradually increased and then decreased to stabilize after 8 hours of reaction. The reaction system was then cooled to room temperature.

After degassing and then flushing with helium, the reaction mixture was collected after opening the autoclave. The organic phase was separated out using a separating funnel, washed and dried and then analyzed by gas chromatography (area percentage).

The yield of $CF_3$—CFI—$CF_2$I, expressed as the ratio of the number of moles of $CF_3$—CFI—$CF_2$I detected to the number of moles of hexafluoropropene initially introduced, was 81.3%. The test was repeated twice, varying the temperature between 80° C. and 100° C. Equivalent yield values were obtained.

Step b): The equipment used was composed of a Hastelloy C276 autoclave with a volume of 0.8 L, on which was mounted a condenser and a pressure-regulating valve.

The autoclave was immersed in liquid nitrogen and the following constituents were successively introduced: 60 g (3.0 mol) of hydrofluoric acid, all three washed and dried reaction mixtures from step a) and 13.3 g (0.07 mol) of titanium tetrachloride ($TiCl_4$). The temperature of the autoclave was then raised to room temperature (25° C.). The autoclave was then immersed in an oil bath and the temperature was raised to 80° C. while the temperature of the condenser was maintained at about 17° C.

During the reaction, the volatile products were removed continuously, washed in a water washer and collected. After 4 hours of reaction, the autoclave was cooled to room temperature.

It was then degassed and the reaction products were washed, dried and analyzed by gas chromatography.

The yield of $CF_3$—CFI—$CF_3$, expressed by the ratio of the number of moles of $CF_3$—CFI—$CF_3$ detected to the number of moles of hexafluoropropene initially introduced, was 76.8%.

Example 2—Synthesis of $CF_3$—$CF_2$—CHFI

Step a): The equipment used consisted of a 2.0 L Hastelloy C276 autoclave, equipped with a pressure indicator, a thermometric probe, a bursting disc and a magnetic bar stirring system.

The following were successively introduced into the autoclave: 102.0 g (0.4 mol) of iodine, 600.0 g of anhydrous ethanol and 53.0 g (0.4 mol) of (Z)—$CF_3$—CF═CHF (HFO-1225ye(Z)). The reactor was heated at 70° C. for 8 hours and then cooled to room temperature.

After degassing and then flushing with helium, the reaction mixture was collected after opening the autoclave. The organic phase was washed, dried and then analyzed by gas chromatography (area percentage).

The yield of $CF_3$—CFI—CHFI, expressed by the ratio of the number of moles of $CF_3$—CFI—CHFI detected to the number of moles of HFO-1225ye(Z) initially introduced, was 67.4%.

Step b): The equipment used consisted of a 0.5 L Hastelloy C276 autoclave, equipped with a pressure indicator, a thermometric probe, a bursting disc and a magnetic bar stirring system.

The autoclave was immersed in liquid nitrogen and the following constituents were successively introduced: 20 g (1.0 mol) of hydrofluoric acid, 96.2 g (0.25 mol) of $CF_3$—CFI—CHFI and 100.0 g of tetramethylene sulfone (sulfolane). The temperature of the autoclave was then raised to room temperature (25° C.) and then gradually heated to 100° C.

After 4 hours of reaction, the autoclave was cooled to room temperature. It was then degassed and the reaction products were washed, dried and analyzed by gas chromatography.

The yield of $CF_3$—$CF_2$—CHFI, expressed by the ratio of the number of moles of $CF_3$—$CF_2$—CHFI detected to the number of moles of $CF_3$—CFI—CHFI initially introduced, was 98.6%.

The invention claimed is:

1. A process for producing an iodofluoroalkane compound, comprising the steps of:

a) placing a fluoroolefin in contact with hydrogen iodide to form a stream A comprising said iodofluoroalkane compound and unreacted hydrogen iodide, b) separating said stream A into a first stream B1 comprising said iodofluoroalkane compound and a stream B2 comprising unreacted hydrogen iodide, and c) recycling stream B2 into step a), wherein step a) is performed in the gas phase and optionally performed with a catalyst, and if step a) is performed in the presence of a catalyst, the catalyst is selected from the group consisting of an oxide, oxyhalide or halide of an element chosen from Li, Na, K, Cs, Mg, Cr and Ca.

2. The process as claimed in claim 1, characterized in that the hydrogen iodide is anhydrous.

3. The process as claimed in claim 1, characterized in that said fluoroolefin is anhydrous.

4. The process as claimed in claim 1, characterized in that said fluoroolefin is of formula (I) $(R^1)(R^2)C{=}C(R^3)(R^4)$ in which $R^1$, $R^2$, $R^3$ and $R^4$ are, independently of each other, selected from the group consisting of H, F, CI, I, a $C_1$-$C_{10}$ alkyl radical optionally substituted with at least one fluorine atom, a $C_3$-$C_{10}$ cycloalkyl radical optionally substituted with at least one fluorine atom, a $C_2$-$C_{10}$ alkenyl radical optionally substituted with at least one fluorine atom, a $C_3$-$C_{10}$ cycloalkenyl radical optionally substituted with at least one fluorine atom, and a $C_6$-$C_{10}$ aryl radical optionally substituted with at least one fluorine atom; with the proviso that at least one of the substituents $R^1$, $R^2$, $R^3$ or $R^4$ is F or is a radical as defined above including at least one fluorine atom.

5. The process as claimed in claim 4, characterized in that said iodofluoroalkane compound is of formula (II) $(R^1)(R^2)$CH—$C(I)(R^3)(R^4)$ in which $R^1$, $R^2$, $R^3$ and $R^4$ are as defined in claim 4.

6. The process as claimed in claim 1, characterized in that said fluoroolefin is of formula (I) $(R^1)(R^2)C{=}C(R^3)(R^4)$ in which $R^1$, $R^2$, $R^3$ and $R^4$ are, independently of each other, selected from the group consisting of H, F, I, a $C_1$-$C_5$ perfluoroalkyl radical, a $C_5$-$C_{10}$ perfluorocycloalkyl radical, a $C_2$-$C_5$ perfluoroalkenyl radical, a $C_5$-$C_{10}$ perfluorocycloalkenyl radical, a $C_6$-$C_{10}$ perfluoroaryl radical; provided that at least one of the substituents $R^1$, $R^2$, $R^3$ or $R^4$ is F or is a perfluoro radical as defined above.

7. The process as claimed in claim 6, characterized in that said iodofluoroalkane compound is of formula (II) $(R^1)(R^2)$CH—$C(I)(R^3)(R^4)$ in which $R^1$, $R^2$, $R^3$ and $R^4$ are as defined in claim 6.

8. The process as claimed in claim 1, characterized in that said fluoroolefin is of formula (I) $(R^1)(R^2)C{=}C(R^3)(R^4)$ in which $R^1$, $R^2$, $R^3$ and $R^4$ are, independently of each other, selected from the group consisting of H, F or $Y^1$—[—$C(Y^2)(Y^3)$—$]_n$— in which $Y^1$, $Y^2$ and $Y^3$ are, independently of each other and independently for each unit n, selected from the group consisting of H and F; and n is an integer from 1 to 5; provided that at least one of the substituents $R^1$, $R^2$, $R^3$, $R^4$, $Y^1$, $Y^2$ or $Y^3$ is F.

9. The process as claimed in claim 8, characterized in that said iodofluoroalkane compound is of formula (II) $(R^1)(R^2)$CH—$C(I)(R^3)(R^4)$ in which $R^1$, $R^2$, $R^3$ and $R^4$ are as defined in claim 8.

10. The process as claimed in claim 1, characterized in that said fluoroolefin is selected from the group consisting of $CHF{=}CH_2$, $CF_2{=}CH_2$, $CHF{=}CHF$, $CF_2{=}CHF$, $CF_2{=}CF_2$, $CH_3{-}CF{=}CH_2$, $CH_3{-}CH{=}CHF$, $CH_2F{-}CH{=}CH_2$, $CH_3{-}CF{=}CHF$, $CH_2F{-}CF{=}CH_2$, $CH_3{-}CH{=}CF_2$, $CH_2F{-}CH{=}CHF$, $CHF_2{-}CH{=}CH_2$, $CH_3{-}CF{=}CF_2$, $CH_2F{-}CF{=}CHF$, $CHF_2{-}CF{=}CH_2$, $CH_2F{-}CH{=}CF_2$, $CHF_2{-}CH{=}CHF$, $CF_3{-}CH{=}CH_2$, $CH_2F{-}CF{=}CF_2$, $CHF_2{-}CF{=}CHF$, $CF_3{-}CF{=}CH_2$, $CHF_2{-}CH{=}CF_2$, $CF_3{-}CH{=}CHF$, $CHF_2{-}CF{=}CF_2$, $CF_3{-}CF{=}CHF$, $CF_3{-}CH{=}CF_2$, and $CF_3{-}CF{=}CF_2$.

11. The process as claimed in claim 1, characterized in that said iodofluoroalkane compound is selected from the group consisting of $CH_2F{-}CH_2I$, $CHFI{-}CH_3$, $CHF_2{-}CH_2I$, $CF_2I{-}CH_3$, $CH_2F{-}CHFI$, $CHF_2{-}CHFI$, $CF_2I{-}CH_2F$, $CHF_2{-}CF_2I$, $CH_3{-}CHF{-}CH_2I$, $CH_3{-}CFI{-}CH_3$, $CH_3{-}CH_2{-}CHFI$, $CH_3{-}CHI{-}CH_2F$, $CH_2F{-}CH_2{-}CH_2I$, $CH_3{-}CHF{-}CHFI$, $CH_3{-}CFI{-}CH_2F$, $CH_2F{-}CHF{-}CH_2I$, $CH_3{-}CH_2{-}CF_2I$, $CH_3{-}CHI{-}CHF_2$, $CH_2F{-}CH_2{-}CHFI$, $CH_2F{-}CHI{-}CH_2F$, $CHF_2{-}CH_2{-}CH_2I$, $CH_3{-}CHF{-}CF_2I$, $CH_3{-}CFI{-}CHF_2$, $CH_2F{-}CHF{-}CHFI$, $CH_2F{-}CFI{-}CH_2F$, $CHF_2{-}CHF{-}CH_2I$, $CH_2F{-}CH_2{-}CF_2I$, $CH_2F{-}CHI{-}CHF_2$, $CHF_2{-}CH_2{-}CHFI$, $CF_3{-}CH_2{-}CH_2I$, $CF_3{-}CHI{-}CH_3$, $CH_2F{-}CHF{-}CF_2I$, $CH_2F{-}CFI{-}CHF_2$, $CHF_2{-}CHF{-}CHFI$, $CF_3{-}CHF{-}CH_2I$, $CF_3{-}CFI{-}CH_3$, $CHF_2{-}CH_2{-}CF_2I$, $CHF_2{-}CHI{-}CHF_2$, $CF_3{-}CH_2{-}CHFI$, $CF_3{-}CHI{-}CH_2F$, $CHF_2{-}CHF{-}CF_2I$, $CHF_2{-}CFI{-}CHF_2$, $CF_3{-}CHF{-}CHFI$, $CF_3{-}CFI{-}CH_2F$, $CF_3{-}CH_2{-}CF_2I$, $CF_3{-}CHI{-}CHF_2$, $CF_3{-}CHF{-}CF_2I$, and $CF_3{-}CFI{-}CHF_2$.

12. The process as claimed in claim 1, characterized in that step a) also involves:

converting $CF_2{=}CH_2$ into $CF_2I{-}CH_3$; or
converting $CF_2{=}CHF$ into $CF_2I{-}CH_2F$; or
converting $CF_2{=}CF_2$ into $CHF_2{-}CF_2I$; or
converting $CF_3{-}CH{=}CH_2$ into $CF_3{-}CH_2{-}CH_2I$; or
converting $CF_3{-}CF{=}CH_2$ into $CF_3{-}CFI{-}CH_3$; or
converting $CF_3{-}CH{=}CHF$ into $CF_3{-}CH_2{-}CHFI$; or
converting $CF_3{-}CF{=}CHF$ into $CF_3{-}CHF{-}CHFI$; or
converting $CF_3{-}CF{=}CF_2$ into $CF_3{-}CHF{-}CF_2I$.

13. The process as claimed in claim 1, characterized in that said fluoroolefin has a boiling point below 100° C. at atmospheric pressure.

14. The process as claimed in claim 1, characterized in that step a) is performed at a temperature of from 150° C. to 700° C.

15. A process for producing an iodofluoroalkane compound, comprising:

placing a fluoroolefin in contact with hydrogen iodide in the liquid phase in the presence of a solvent S1, wherein said fluoroolefin is of formula (I) (R1)(R2)C=C(R3)(R4) in which R1, R2, R3 and R4 are, independently of each other, chosen from the group consisting of H, F, I, a C1-C5 perfluoroalkyl radical, a C5-C10 perfluorocycloalkyl radical, a C2-C5 perfluoroalkenyl radical, a C5-C10 perfluorocycloalkenyl radical, and a C6-C10 perfluoroaryl radical; provided that at least one of the substituents R1, R2, R3 or R4 is F or is a perfluoro radical as defined above;

wherein said fluoroolefin has a boiling point below 100° C. at atmospheric pressure;

wherein the solvent S1 has a boiling point of from 0° C. to 250° C. and is chosen from the group consisting of acetic acid, CC14, chloroform, dichloromethane, sulfolane, tetramethylene sulfone, N,N-dimethylformamide, dimethyl sulfoxide, N,N-dimethylacetamide, N-methylpyrrolidone, 1,3-dimethyl-2-imidazolidinone, 1,3-dimethyl-3,4,5,6-tetrahydro-2-pyrimidinone, and mixtures thereof;

wherein the process is performed in the presence of a catalyst chosen from alkali metal or alkaline-earth metal salts; and wherein the process is performed at a temperature of from 50° C. to 280° C.

16. The process as claimed in claim 15, characterized in that the hydrogen iodide is anhydrous.

17. The process as claimed in claim 15, characterized in that said fluoroolefin is anhydrous.

18. The process as claimed in claim 15, characterized in that said fluoroolefin is of formula (I)$(R^1)(R^2)C{=}C(R^3)(R^4)$ in which $R^1$, $R^2$, $R^3$ and $R^4$ are, independently of each other, selected from the group consisting of H, F or $Y^1{-}[{-}C(Y^2)(Y^3){-}]_n{-}$ in which $Y^1$, $Y^2$ and $Y^3$ are, independently of each other and independently for each unit n, selected from the group consisting of H and F; and n is an integer from 1 to 5; provided that at least one of the substituents $R^1$, $R^2$, $R^3$, $R^4$, $Y^1$, $Y^2$ or $Y^3$ is F.

19. The process of claim 15, wherein the catalyst is an alkali metal salt.

20. The process of claim 19, wherein the catalyst is chosen from NaI, KI, and mixtures thereof.

* * * * *